(12) United States Patent
Mohammed et al.

(10) Patent No.: US 7,335,470 B2
(45) Date of Patent: Feb. 26, 2008

(54) COMPILATIONS OF NUCLEIC ACIDS AND ARRAYS AND METHODS OF USING THEM

(75) Inventors: Mansoor Mohammed, Houston, TX (US); Jason Kang, Houston, TX (US); Shishir Shah, Houston, TX (US); Wei-Wen Cai, Pearland, TX (US)

(73) Assignee: PerkinElmer, LAS, Inc., Waltham, MA (US)

( * ) Notice: Subject to any disclaimer, the term of this patent is extended or adjusted under 35 U.S.C. 154(b) by 555 days.

(21) Appl. No.: 10/273,399

(22) Filed: Oct. 15, 2002

(65) Prior Publication Data

US 2004/0009493 A1    Jan. 15, 2004

(51) Int. Cl.
*C12Q 1/68* (2006.01)
*C12N 15/00* (2006.01)
*C12N 15/11* (2006.01)

(52) U.S. Cl. ............... 435/6; 435/320.1; 536/23.1
(58) Field of Classification Search ............... None
See application file for complete search history.

(56) References Cited

U.S. PATENT DOCUMENTS

| | | | |
|---|---|---|---|
| 4,337,063 A | 6/1982 | Mihara et al. | 436/536 |
| 4,355,153 A | 10/1982 | Radici et al. | 528/191 |
| 4,404,289 A | 9/1983 | Masuda et al. | 436/538 |
| 4,458,066 A | 7/1984 | Caruthers et al. | 536/25.34 |
| 4,652,613 A | 3/1987 | Collins et al. | 525/69 |
| 4,683,195 A | 7/1987 | Mullis et al. | 435/6 |
| 4,683,202 A | 7/1987 | Mullis et al. | 435/91.2 |
| 4,774,339 A | 9/1988 | Haugland et al. | 548/405 |
| 4,806,631 A | 2/1989 | Carrico et al. | 536/25.3 |
| 4,818,681 A | 4/1989 | Dattagupta | 435/6 |
| 4,826,789 A | 5/1989 | Jones et al. | 501/80 |
| 4,826,790 A | 5/1989 | Jones et al. | 501/90 |
| 4,937,188 A | 6/1990 | Giese et al. | 435/41 |
| 4,957,858 A | 9/1990 | Chu et al. | 435/6 |
| 4,963,436 A | 10/1990 | Jones et al. | 428/403 |
| 5,008,220 A | 4/1991 | Brown et al. | 501/81 |
| 5,024,933 A | 6/1991 | Yang et al. | 435/6 |
| 5,047,519 A | 9/1991 | Hobbs et al. | 536/27.14 |
| 5,055,429 A | 10/1991 | James et al. | 501/80 |
| 5,068,269 A | 11/1991 | Diamantoglou | 524/35 |
| 5,135,717 A | 8/1992 | Renzoni et al. | 422/61 |
| 5,143,854 A | 9/1992 | Pirrung et al. | 436/518 |
| 5,151,507 A | 9/1992 | Hobbs et al. | 536/26.7 |
| 5,187,288 A | 2/1993 | Kang et al. | 548/110 |
| 5,188,934 A | 2/1993 | Menchen et al. | 435/6 |
| 5,190,864 A | 3/1993 | Giese et al. | 435/41 |
| 5,215,882 A | 6/1993 | Bahl et al. | 435/6 |
| 5,227,487 A | 7/1993 | Haugland et al. | 546/15 |
| 5,248,782 A | 9/1993 | Haugland et al. | 548/110 |
| 5,266,489 A | 11/1993 | Rey-Senelgonge et al. | 435/320.1 |
| 5,268,486 A | 12/1993 | Waggoner et al. | 548/427 |
| 5,274,113 A | 12/1993 | Kang et al. | 548/405 |
| 5,288,625 A | 2/1994 | Hudlaczky | 435/449 |
| 5,288,641 A | 2/1994 | Roszman | 435/320.1 |
| 5,324,633 A | 6/1994 | Fodor et al. | 435/6 |
| 5,433,896 A | 7/1995 | Kang et al. | 252/700 |
| 5,434,049 A | 7/1995 | Okano et al. | 435/6 |
| 5,472,842 A | 12/1995 | Stokke et al. | 435/6 |
| 5,501,979 A | 3/1996 | Geller et al. | 435/320.1 |
| 5,514,785 A | 5/1996 | Van Ness et al. | 536/22.1 |
| 5,532,226 A | 7/1996 | Demarest et al. | 514/134 |
| 5,539,517 A | 7/1996 | Cabib et al. | 356/456 |
| 5,554,744 A | 9/1996 | Bhongle et al. | 536/25.3 |
| 5,556,752 A | 9/1996 | Lockhart et al. | 435/6 |
| 5,578,832 A | 11/1996 | Trulson et al. | 250/458.1 |
| 5,601,982 A | 2/1997 | Sargent et al. | 435/6 |
| 5,610,287 A | 3/1997 | Nikiforov et al. | 536/24.3 |
| 5,614,386 A | 3/1997 | Metzker et al. | 435/91.1 |
| 5,630,932 A | 5/1997 | Lindsay et al. | 205/645 |
| 5,632,957 A | 5/1997 | Heller et al. | 422/68.1 |
| 5,635,351 A | 6/1997 | Feuerstein et al. | 435/6 |
| 5,637,687 A | 6/1997 | Wiggins | 536/25.4 |
| 5,641,630 A | 6/1997 | Snitman et al. | 435/6 |
| 5,652,099 A | 7/1997 | Conrad et al. | 435/6 |
| 5,665,549 A | 9/1997 | Pinkel et al. | 435/6 |
| 5,684,148 A | 11/1997 | Caruthers et al. | 536/26.1 |
| 5,700,637 A | 12/1997 | Southern | 435/6 |
| 5,714,386 A | 2/1998 | Roederer | 436/546 |
| 5,721,098 A | 2/1998 | Pinkel et al. | 435/6 |

(Continued)

FOREIGN PATENT DOCUMENTS

WO    WO 96/17958 A1    6/1996

(Continued)

OTHER PUBLICATIONS

Eisen et al, Methods Enzymol. 303: 179 (1999).*

(Continued)

*Primary Examiner*—James Martinell
(74) *Attorney, Agent, or Firm*—Lowrie, Lando & Anastasi, LLP

(57) ABSTRACT

In one aspect the invention provides compilations of nucleic acids, articles of manufacture, e.g., arrays, and methods for the detection of chromosomal abnormalities, such as a chromosomal aneuploidies, deletions, amplifications, and the like, and the diagnosis or prognosis of syndromes associated with a contiguous gene abnormality. Kits are also provided.

98 Claims, No Drawings

U.S. PATENT DOCUMENTS

| | | | |
|---|---|---|---|
| 5,721,118 A | 2/1998 | Scheffler | 435/69.1 |
| 5,744,305 A | 4/1998 | Fodor et al. | 435/6 |
| 5,770,456 A | 6/1998 | Holmes | 436/518 |
| 5,776,745 A | 7/1998 | Ketner et al. | 435/477 |
| 5,790,727 A | 8/1998 | Dhadwal et al. | 385/38 |
| 5,795,557 A | 8/1998 | Pajonk et al. | 423/338 |
| 5,800,992 A | 9/1998 | Fodor et al. | 435/6 |
| 5,807,522 A | 9/1998 | Brown et al. | 422/50 |
| 5,830,645 A | 11/1998 | Pinkel et al. | 435/6 |
| 5,843,767 A | 12/1998 | Beattie et al. | 435/287.1 |
| 5,846,708 A | 12/1998 | Hollis et al. | 435/6 |
| 5,856,097 A | 1/1999 | Pinkel et al. | 435/6 |
| 5,856,174 A | 1/1999 | Lipshutz et al. | 435/286.5 |
| 5,863,504 A | 1/1999 | Heffelfinger et al. | 422/82.08 |
| 5,874,259 A | 2/1999 | Szybalski | 435/91.1 |
| 5,880,473 A | 3/1999 | Ginestet | 250/458.1 |
| 5,922,617 A | 7/1999 | Wang et al. | 436/518 |
| 5,925,525 A | 7/1999 | Fodor et al. | 435/6 |
| 5,939,261 A | 8/1999 | Loewy et al. | 435/6 |
| 5,943,129 A | 8/1999 | Hoyt et al. | 356/318 |
| 5,959,098 A | 9/1999 | Goldberg et al. | 536/25.3 |
| 5,962,674 A | 10/1999 | Iyer et al. | 536/25.34 |
| 5,965,362 A | 10/1999 | Pinkel et al. | 435/6 |
| 5,965,452 A | 10/1999 | Kovacs | 436/149 |
| 5,976,790 A | 11/1999 | Pinkel et al. | 435/6 |
| 5,981,175 A | 11/1999 | Loring et al. | 435/6 |
| 6,001,982 A | 12/1999 | Ravikumar et al. | 536/22.1 |
| 6,013,440 A | 1/2000 | Lipschutz et al. | 435/6 |
| 6,022,963 A | 2/2000 | McGall et al. | 536/25.3 |
| 6,024,872 A | 2/2000 | Mahendran et al. | 210/500.25 |
| 6,025,155 A | 2/2000 | Hadlaczky et al. | 435/69.1 |
| 6,027,709 A | 2/2000 | Little et al. | 424/1.65 |
| 6,028,190 A | 2/2000 | Mathies et al. | 536/26.6 |
| 6,031,092 A | 2/2000 | Just et al. | 536/25.34 |
| 6,040,138 A | 3/2000 | Lockhart et al. | 435/6 |
| 6,045,996 A | 4/2000 | Cronin et al. | 435/6 |
| 6,048,457 A | 4/2000 | Kopaciewicz et al. | 210/321.6 |
| 6,048,695 A | 4/2000 | Bradley et al. | 435/6 |
| 6,048,982 A | 4/2000 | Waggoner | 548/148 |
| 6,049,380 A | 4/2000 | Goodwin et al. | 356/317 |
| 6,051,719 A | 4/2000 | Benson et al. | 548/416 |
| 6,054,270 A | 4/2000 | Southern | 435/6 |
| 6,054,279 A | 4/2000 | Nadeau et al. | 435/6 |
| 6,055,325 A | 4/2000 | Garini et al. | 382/129 |
| 6,060,324 A | 5/2000 | Naguib | 436/71 |
| 6,063,338 A | 5/2000 | Pham et al. | 422/61 |
| 6,066,459 A | 5/2000 | Garini et al. | 435/6 |
| 6,077,673 A | 6/2000 | Chenchik et al. | 435/6 |
| 6,096,817 A | 8/2000 | McNamara | 524/406 |
| 6,140,044 A | 10/2000 | Besemer et al. | 435/6 |
| 6,143,495 A | 11/2000 | Lizardi et al. | 435/6 |
| 6,159,685 A | 12/2000 | Pinkel et al. | 435/6 |
| 6,183,957 B1 | 2/2001 | Cole et al. | 435/6 |
| 6,191,425 B1 | 2/2001 | Imai | 250/458.1 |
| 6,197,501 B1 | 3/2001 | Cremer et al. | 435/6 |
| 6,197,506 B1 | 3/2001 | Fodor et al. | 435/6 |
| 6,235,504 B1 | 5/2001 | Zhang et al. | 435/91.2 |
| 6,251,601 B1 | 6/2001 | Bao et al. | 435/6 |
| 6,252,664 B1 | 6/2001 | Barbera-Guillem | 356/417 |
| 6,258,606 B1 | 7/2001 | Kovacs | 436/149 |
| 6,261,776 B1 | 7/2001 | Pirrung et al. | 435/6 |
| 6,268,132 B1 | 7/2001 | Conrad | 435/6 |
| 6,277,489 B1 | 8/2001 | Abbott et al. | 428/403 |
| 6,277,581 B1 | 8/2001 | O'Brien et al. | 435/6 |
| 6,277,621 B1 | 8/2001 | Horsburgh et al. | 435/235.1 |
| 6,277,628 B1 | 8/2001 | Johann et al. | 435/287.2 |
| 6,294,331 B1 | 9/2001 | Ried et al. | 435/6 |
| 6,294,338 B1 | 9/2001 | Nunomura | 435/6 |
| 6,309,822 B1 | 10/2001 | Fodor et al. | 435/6 |
| 6,344,316 B1 | 2/2002 | Lockhart et al. | 435/6 |
| 6,403,320 B1 | 6/2002 | Read et al. | 435/6 |
| 2001/0007747 A1 | 7/2001 | Bochkariav et al. | 435/6 |
| 2001/0008765 A1 | 7/2001 | Shinoki et al. | 435/7.1 |
| 2001/0012537 A1 | 8/2001 | Anderson et al. | 427/2.1 |
| 2001/0014448 A1 | 8/2001 | Chappa et al. | 435/6 |
| 2001/0014449 A1 | 8/2001 | Nerenberg et al. | 435/6 |
| 2001/0016322 A1 | 8/2001 | Caren et al. | 435/6 |
| 2001/0018514 A1 | 8/2001 | McGall et al. | 536/26.6 |
| 2001/0018642 A1 | 8/2001 | Balaban et al. | 702/19 |
| 2001/0019827 A1 | 9/2001 | Dawson et al. | 435/6 |

FOREIGN PATENT DOCUMENTS

| | | |
|---|---|---|
| WO | WO 96/39154 A1 | 12/1996 |
| WO | WO 97/03211 A1 | 1/1997 |
| WO | WO 97/46313 A1 | 12/1997 |
| WO | 99/09218 | 2/1999 |
| WO | WO 99/09217 A1 | 2/1999 |
| WO | 99/13319 | 3/1999 |
| WO | WO 99/51773 A1 | 10/1999 |
| WO | WO 99/60663 A1 | 11/1999 |
| WO | WO 00/09650 A1 | 2/2000 |
| WO | WO 00/26412 A1 | 5/2000 |
| WO | WO 00/42222 A2 | 7/2000 |
| WO | WO 00/42222 A3 | 7/2000 |
| WO | WO 00/47600 A1 | 8/2000 |
| WO | WO 01/01144 A3 | 1/2001 |
| WO | WO 02/33044 A2 | 4/2002 |
| WO | WO 03/091426 A1 | 11/2003 |

OTHER PUBLICATIONS

Molecular Biology Reagents/Protocols 1992, United States Biochemical Corporation, 1991, Cleveland, Ohio, pp. 218-219.*

Kern, et al., "Direct Hybridization of Large-Insert Genomic Clones on HIgh-Density Gridded cDNA Filter Arrays", BioTechniques 23:120-124, Jul. 1997.

Rice, et al., "Comparative Genomic Hybridization in Pediatric Acute Lymphoblastic Leukemia", Pediatric Hematology and Oncology, 17:141-147, 2000.

Kim, et al., "Putative Chromosomal Deletions on 9P, 9Q and 22Q Occur Preferentially in Malignant Gastorintestinal Stromal Tumors", Int. J. Cancer; 85, 633-638; 2000.

Houldsworth, et al., "Comparative Genomic Hybridization: An Overview", American Journal of Pathology, vol. 145, No. 6, Dec. 1994.

Wa'el Fi-Rital, et al., "High-Resolution Deletion Mapping of Chromosome 14 in Stromal Tumors of the Gastrointestinal 14 in Stromal Tumors of the Gastrointestinal Tract Suggests Two Distinct Tumor Suppressor Loci", Genes, Chromosomes & Cancer 27:387-391; 2000.

David J. Stewart, "Making and Using DNA Microarrays: A Short Course at Cold Spring Harbor Laboratory", Genome Research, www.genome.org, vol. 10 (1), 1-3.

Suzuki, et al., "Construction and evaluation of a porcine bacterial artificial chromosome library", Anim Genet; 31(1): Feb. 2000, abstract only.

Bertucci, et al., "Sensitivity issues in DNA array-based expression measurements and performance of nylon microarrays for small samples", Hum Mol Genet; 8(9):1715; Sep. 1999, abstract only.

Zhao, et al., "High-density cDMA filter analysis: a novel approach for large-scale, quantitative analysis of gene expression", Gene 156(2):207; Apr. 24, 1995, abstract only.

Kern, et al., "Direct hybridization of large-insert genomic clones on high-density gridded cDNA filter arrays", Biotechniques; 23(1):120; Jul. 1997, abstract only.

DeRisi, et al., "Genomics and array technology", Current Opinion Oncology; 11(1):76; Jan. 1999, abstract only.

Yan, et al., "CpG Island Arrays: An Application toward Deciphering Epigenetic Signatures of Breast Cancer", Clinical Cancer Research; vol. 6, No. 4, 1433-1438, Apr. 2000.

Huang, et al., "Methylation profiling of CpG islands in human breast cancer cells", Human Molecular Genetics, vol. 8, No. 3m 459-470; 1999.

J. P. Issa, "CpG-Island Methylation in Aging and Cancer", Curr. Top. Microbiol. Immunol. 249, pp. 101-118; 2000.

Pfeifer, et al., "Mutation Hotspots and DNA Methylation", Curr. Top. Microbiol. Immunol. 249, pp. 1-19; 2000.

Cross, et al., "CpG island libraries from human Chromosomes 18 and 22: landmarks for novel genes", Mammalian Genome, vol. 11, No. 5, May 2000.

Eads, et al., "MethyLight: a high-throughput assay to measure DNA methylation", Nucleic Acids Research, vol. 28, No. 8 E32-00; 2000.

Pogribny, et al., "A Sensitive New Method for Rapid Detection of Abnormal Methylation Patterns in Global DNA and within CpG Islands", Biochemical and Biophysical Research Communications 262, 624-628; 1999.

Edward J. Oakeley, "DNA methylation analysis: a review of current methodologies", Pharmacology & Therapeutics, vol. 84, No. 3, pp. 389-400; Dec. 1999.

Robertson, et al., "DNA methylation: past, present and future directions", Carcinogenesis, vol. 21, No. 3, pp. 461-467; Mar. 2000.

Fan, et al., "Parallel Genotyping of Human SNPs Using Generic High-density Oligonucleotide Tag Arrays", Research, vol. 10, No. 6, pp. 853-860; Jun. 2000.

Spolsky, et al., "High-throughput polymorphism screening and genotyping with high-density oligonucleotide arrays", Genetic Analysis Biomolecular Engineering, vol. 14, Nos. 5-6, 187-192; Feb. 1999.

Emerson, et al., LXIII Cold Spring Harbor Symposium on Quantitative Biology: Mechanisms of Transcription, Biochimica et Biophysica Acta 1423 R45-R51; 1998.

DeRisi, J., et al., "Use of a cDNA microarray to analyze gene expression patterns in human cancer," Nature Genetics, 14:457-460; 1996.

Schena, et al., "Parallel human genome analysis: Microarray-based expression monitoring of 1000 genes", Proc. Natl. Acad. Sci. vol. 93, pp. 10614-10619, Oct. 1996.

Schena, et al., "Quantitative Monitoring of Gene Expression Patterns with a Complementary DNA Microarray", Science, vol. 270, pp. 467-470; Oct. 20, 1995.

Shalon, et al., "A DNA Microarray System for Analyzing Complex DNA Samples Using Two-color fluorescent Probe Hybridization", Genome Research, 6:639-645; 1996.

Maskos, et al., "Oligonucleotide hybridisations on glass supports: a novel linker for oligonucleotide synthesis and hybridisation properties of oligonucleotides synthesised in situ", Nucleic Acids Research, vol. 20, No. 7; pp. 1679-1684; Mar. 1992.

Hacia, et al., "Detection of heterozygous mutations in BGRCA1 using high density oligonucleotide arrays and two-colour fluorescence analysis", nature genetics, vol. 14; pp. 441-447; Dec. 1996.

Lockhart, et al., "Expression monitoring by hybridization to high-density oligonucleotide arrays", Nature Biotechnology, vol. 14, pp. 1675-1680; Dec. 1996.

Guo, et al., "Direct fluorescence analysis of genetic polymorphisms by hybridization with oligonucleotide arrays on glass supports", Nucleic Acids Research, vol. 22, No. 24, pp. 5456-5465; 1994.

Ramsay, Graham, "DNA chips: State-of-the-Art", Nature Biotechnology, vol. 16, pp. 40-44; Jan. 1998.

Marshall, et al., "DNA chips: An array of possibilities", Nature Biotechnology, Vo. 16, pp. 27-31; Jan. 1998.

Castellino, Alexander M., "When the Chips are Down", Genome Research, vol. 7, pp. 943-946; 1997.

Schena, Mark, "Genome analysis with gene expression microarrays", BioEssays, vol. 18 No. 5; pp. 427-431; Jan. 1996.

Beattie, et al., "Hybridization of DNA Targets to Glass-Tethered Oligonucleotide Probes", Molecular Biotechnology, vol. 4, pp. 213-225; 1995.

Anderson, et al., "Quantitative Fiber Hybridisation", *Nucleic acid hybridisation, a practical approach*, IRL Press, 1985, pp. 98-99.

Suzuki et al., "Construction and evaluation of a porcine bacterial artificial chromosome library," *Anim. Genet.*, 31(1) Feb. 2000.

Zhao et al., "High-density cDMA filter analysis: a novel approach for large-scale, quantitative analysis of gene expression," *Gene*, 156(2): 207, Apr. 24, 1995.

DeRisi et al., "Genomics and array technology," *Current Opinion Oncology*, 11(1) Jan. 1999, pp. 76-81.

Kuroiwa, *Nat. Biotechnol.* 18:1086-1090, 2000.
Mejia, *Am. J. Hum. Genet.*, 69:315-326, 2001.
Csonka, *J. Cell Sci.*, 113 (Pt. 18):3207-3216, 2000.
Feingold, *Proc. Nat'l. Acad.Sci. USA*, 87:8637-8641, 1990.
Tucker, *Gene*, 199:25-30, 1997.
Adam, *Plant J.*, 11:1349-1358, 1997.
Zeschnigk, *Nucleic Acids Res.*, 27(21), c 30 (1999).
Asakawa; *Gene*, 69-79, 1997.
Cao, *Genome Res.* 9:763-774, 1999.
Mejia, *Genome Res.*, 7:179-186, 1997.
Ashworth, *Analytical Biuochem.* 224:564-571, 1995.
Birch, *Lett. Appl. Microbiol.* 33:296-301, 2001.
Greijer, *J. Virol. Methods*, 96:133-147, 2001.
Kimmel et al , Methods Enzymol. 152:307-316, 1987.
Thorstenson, *Genome Res.*, 8::848-855, 1998.
Ichikawa, *Asian J. Androl.* 2(3): 167-171, 2000.
Cui et al., *Cancer Genet. Cytolgenet*, 107:51, 1998.
Matsuyama et al., *Aktuel Urol.* 34:247, 2003.
Matsuyama et al., Prostate 54 : 103 (2003).
Eugster, *Amer. J. Med. Genet.*, 40(4):409-412, 1997.
Reish, *Amer. J. Med. Genet.*, 59(4):467-475, 1995.
Smeets, *Genet. Couns.* 12(1):85-89, 2001.
Battaglia, *Adv. Pediatr.*, 48:75-113, 2001.
Marcelis, *Genet. Couns,*. 12:35-48, 2001.
Kant, *J. Med. Genet.*, 34(7):569-572, 1997.
Pollin, *Amer. J. Med. Genet.*, 85(4):369-375, 1999.
Donnai, *Amer. J. Med. Genet.*, 97(2):164-171, 2000.
Hilton, *Genomics*, 71(2):192-199, 2001.
Nardmann, *Hum. Genet.*, 99(5):638-643, 1997.
George, *J. Eur. Acad. Dermatol. Venereol.* 11(1):66-68, 1998.
Naselli, *Pediatr. Radio.* 28(11):851-855, 1998.
Chilosi, *Amer. J. Med. Genet.*, 100(2):138-144, 2001.
Kobayashi, *J. Craniomaxillofac. Sugy.*, 28(3):165-170, 2000.
Dasouki, *Amer. J. Med. Genet.*, 73(1):72-75, 1997.
Lichtner, *J. Med. Genet.*, 37(1):33-37, 2000.
Epstein, *Trends Genet.* 17(10):S13-17, 2001.
Crolla, *J. Med. Genet.* 34(3):207-212, 1997.
Ariel, *Pediatr. Pathol. Lab. Med.* 16(6):1013-1021, 1996.
Li, *Genomics*, 74(3):370-376, 2001.
Torrisi, *Am. J. Med. Genet.*, 106(2):125-128, 2001.
Baumer, *Hum. Genet*, 105(6):598-602, 1999.
Greger, *Am. J. Hum. Genet*, 60(3):574-580, 1997.
Manini, *Clin. Neurophysiol.*, 112(5):800-805, 2001.
Vilella, *Arch. Dis. Child.* 83(4):360-361, 2000.
Badano, *Clin. Chem.* 47(5):838-843, 2001.
Mersiyanova, *Hum. Mutat.* 15(4):340-347, 2000.
Chance, *Phys. Med. Rehabil. Clin N. Am.* 12(2):277-291, 2001.
Lane, *J. Hand Surg.* [Am] 26(4):670-674, 2001.
King, *Acta Neuropathol* (Berl) 99(4):425-427, 2000.
Honda *Brain Dev.* 20(3):190-192, 1998.
Juyal, *Am. J. Hum. Genet.* 58(5):998-1007, 1996.
Thomas, *Fetal Diagn. Ther.* 15(6):335-337, 2000.
DeLeersnyder, *J. Pediatr.* 139(1):111-116, 2001.
Yuan, *Acta Paediatr.* Jpn 39(6):647-652, 1997.
Hol, *Hum. Genet.* 95(6):687-690, 1995.
Smith, *Am. J. Med. Genet.* 81(2):186-191, 1998.
Eliez, *Am. J. Psychiatry* 158(3):447-453, 2001.
Fokstuen, *Eur. J. Pediatr.* 160(1):54-57, 2001.
Peter, *J. Clin. Endocrinol. Metab.* 83(8):2666-2674, 1998.
Grain, *Neuromuscul. Disord.* 11(2):186-191, 2001.
Crilley, *J. Am. Coll. Cardio.* 36(6):1953-1958, 2000.
Sjarif, *J. Inherit. Metab. Dis.* 23(6):529-547, 2000.
Scheuerle, *J. Pediatr.* 126(5 Pt 1):764-767, 1995.
Weissortel, *Clin. Genet.* 54(1):45-51, 1998.
Santolaya-Forgas, *Fetal Diagn. Ther.* 12(1):36-39, 1997.
Damiani, *J. Pediatr Endocrinol. Metab.* 12(6):827-831, 1999.
Kadandale, *Microb. Comp. Genomics* 5(2):71-74, 2000.
Yu, *Nat. Genet.* 20(4):353-357, 1998.
Vasquez, *Genet. Couns.* 10(3):301-304, 1999.
Maya-Nunez, *Clin. Endocrinol.* (Oxf) 50(2):157-162, 1999.
Zappia, *J. Otolaryngol.* 21(1):16-19, 1992.
Guerrini, *Epilepsia* 42 Suppl 3:36-41, 2001.
Shanske, *Am. J. Med. Genet.* 102(3):231-236, 2001.

Rickard, *Hum. Genet.* 108(5):398-403, 2001.
DiCicco, *Int. J. Pediatr. Otohinolaryngol* 59(2):147-150, 2001.
Moore, *Eur. J. Hum. Genet.* 8:223-228, 2000.
Djalali, *Prenat. Diagn.* 20:934-935, 2000.
Harrison, *Hum. Genet.* 92:353-358, 1993.

Fung, *J. Histochem. Cytochem.* 49:797-798, 2001.
Sanz, *Fetal Diagn. Ther.* 16:95-97, 2001.
Ibanez, *Mol. Reprod. Dev.* 58:166-172, 2001.

\* cited by examiner

COMPILATIONS OF NUCLEIC ACIDS AND ARRAYS AND METHODS OF USING THEM

TECHNICAL FIELD

This invention relates to molecular biology, genetic diagnostics and array, or "biochip," technology. In one aspect the invention provides compilations of nucleic acids, articles of manufacture, e.g., arrays, and methods for the detection of chromosomal abnormalities, such as a chromosomal aneuploidies, amplifications, deletions, and the like, and the diagnosis or prognosis of syndromes associated with a contiguous gene abnormality.

BACKGROUND

Genomic DNA microarray based comparative genomic hybridization (CGH) has the potential to perform faster, more efficiently and cheaper than traditional CGH methods, which rely on comparative hybridization on individual metaphase chromosomes. Array-based CGH uses immobilized nucleic acids arranged as an array on a biochip or a microarray platform. The so-called array or chip CGH approach can provide DNA sequence copy number information across the entire genome in a single, timely, cost-effective and sensitive procedure. The resolution of chip CGH is primarily dependent upon the number, size and map positions of the DNA elements within the array. Typically, bacterial artificial chromosomes, or BACs, which can each accommodate on average about 150 kilobases (kb) of cloned genomic DNA, are used in the production of the array.

The principle of the array CGH approach is simple. Equitable amounts of total genomic DNA from cells of a test sample and a reference sample (e.g., a sample from cells known to be free of chromosomal aberrations) are differentially labeled with fluorescent dyes and co-hybridized to the array of BACs, which contain the cloned genomic DNA fragments that collectively cover the cell's genome. The resulting co-hybridization produces a fluorescently labeled array, the coloration of which reflects the competitive hybridization of sequences in the test and reference genomic DNAs to the homologous sequences within the arrayed BACs. Theoretically, the copy number ratio of homologous sequences in the test and reference genomic DNA samples should be directly proportional to the ratio of their respective fluorescent signal intensities at discrete BACs within the array. The versatility of the approach allows the detection of constitutional variations in DNA copy number in clinical cytogenetic samples such as amniotic samples, chorionic villus samples (CVS), blood samples and tissue biopsies. It also allows detection of somatically acquired genomic changes in tumorigenically altered cells, for example, from bone marrow, blood or solid tumor samples.

SUMMARY

The invention provides novel compilations, or sets, libraries or collections, of nucleic acids and articles of manufacture, e.g., articles of manufacture, e.g., arrays, and methods of making and using them. These compilations, or sets, libraries or collections, of nucleic acids and arrays can be used in the detection of a chromosomal abnormality, such as a chromosomal aneuploidy, or in the diagnosis or prognosis of a syndrome associated with a contiguous gene abnormality.

The invention provides an articles of manufacture, e.g., an array, for the detection of a chromosomal abnormality or a diagnosis of a syndrome associated with a contiguous gene abnormality, comprising: a plurality of nucleic acids segments, wherein each nucleic acid segment is immobilized to a discrete and known spot on a substrate surface to form an array of nucleic acids, and each spot comprises a segment of genomic nucleic acid associated with a chromosomal abnormality, a contiguous gene abnormality, a genetically linked disease or a syndrome. In alternative aspects, the segment of genomic nucleic acid comprises: chromosome 1, locus 1p;36, and the syndrome detected is 1p Deletion Syndrome; chromosome 1, locus 7p11.2, and the syndrome detected is Smith-Magenis syndrome (SMS); chromosome 3, locus 3p25-pter, and the syndrome detected is 3p Deletion Syndrome; chromosome 3, locus 3p21-pter, and the syndrome detected is 3p Duplication Syndrome; chromosome 4, locus 4p16.3, and the syndrome detected is Wolf-Hirschhorn Syndrome; chromosome 4, locus 4p15.2-16.1, and the syndrome detected is 4p Duplication Syndrome; chromosome 5, locus 5p15.2-pter, and the syndrome detected is Cri du Chat Syndrome; chromosome 7, locus 7p13.3, and the syndrome detected is Miller-Dieker Syndrome; chromosome 7, locus 7q11.23, and the syndrome detected is Williams Syndrome; chromosome 8, locus 8q24.1, and the syndrome detected is Langer-Giedion Syndrome (LGS); chromosome 8, locus 8q24.1, and the syndrome detected is Trichorhinophalangeal Syndrome (TRPS); chromosome 8, locus 8q13.3, and the syndrome detected is branchio-oto-renal (BOR) syndrome; chromosome 9, locus 9p, e.g., locus 9p22-pter, and the syndrome detected is 9p Deletion Syndrome; chromosome 10, locus 10p13-p14, and the syndrome detected is DiGeorge Syndrome II; chromosome 11, locus 11p13, and the syndrome detected is WAGR Syndrome; chromosome 11, locus 11p15.5, and the syndrome detected is Beckwith-Wiedemann Syndrome; chromosome 11, locus 11p11.2, and the syndrome detected is Potocki-Shaffer Syndrome (Multiple Exostoses II Locus); chromosome 13, locus 13q22, and the syndrome detected is Hirschsprung disease and Waardenburg syndrome; chromosome 15, locus 15q12, and the syndrome detected is Angelman Syndrome; chromosome 15, locus 15q12, and the syndrome detected is Prader-Willi Syndrome; chromosome 16, locus distal 16p13.3, and the syndrome detected is Rubinstein-Taybi Syndrome; chromosome 16, pericentromeric region, and the syndrome detected is idiopathic epilepsy and paroxysmal dyskinesia; chromosome 17, locus 17p12, and the syndrome detected is Charcot-Marie-Tooth Disease Type 1A(CMT-1A); chromosome 17, locus 17p12, and the syndrome detected is Hereditary Neuropathy with Liability to Pressure Palsies; chromosome 17, locus 17p13.3, and the syndrome detected is Miller-Dieker Syndrome/Isolated Lissencephaly; chromosome 17, locus 17p11.2, and the syndrome detected is Smith-Magenis Syndrome; chromosome 20, locus 20p11.2-p12, and the syndrome detected is Alagille Syndrome; chromosome 22, locus 22q11.2, and the syndrome detected is DiGeorge/Velocardiofacial Syndrome; chromosome X, locus Xp21, and the syndrome detected is Adrenal Hypoplasia Congenita (AHC); chromosome X, locus Xp21, and the syndrome detected is Duchenne/Becker Muscular Dystrophy; chromosome X, locus Xp21, and the syndrome detected is Glycerol Kinase Deficiency; chromosome X, locus Xp22, and the syndrome detected is Pelizaeus-Merzbacher Disease; chromosome X, locus Xp22.3, and the syndrome detected comprises steroid sulfatase deficiency; chromosome X, locus Xp22.3, and the syndrome detected is Leri-Weill syndrome; chromosome Y, locus SRY locus/Yp, and the syndrome detected comprises abnormalities of the SRY locus; chromosome X, locus Xp22.3, and the syndrome detected is Kallman Disease; chromosome X, locus Xp21, and the syndrome detected is Sex Reversal (DSS); chromosome 17, locus 17p11.2, and the syndrome detected is 17p11.2 Duplication Syndrome; and, chromosome 17, locus 17p11.2, and the syndrome detected is Smith-Magenis syndrome (SMS).

In alternative aspects, the array further comprises at least one spot comprising a nucleic acid segment acting as a positive control, at least one spot comprising a nucleic acid segment acting as a negative control, or a combination thereof.

In alternative aspects of the array, about 25%, 30%, 35%, 40%, 45%, 50%, 55%, 60%, 65%, 70%, 75%, 80%, 85%, 90%, 95%, 98%, 99%, or more, or 100% of the spots comprise a segment of genomic nucleic acid associated with a chromosomal abnormality, a contiguous gene abnormality, a genetically linked disease or a syndrome.

In one aspect, the array-immobilized genomic nucleic acid segments in a first spot are substantially or completely non-overlapping in sequence compared to the array-immobilized genomic nucleic acid segments in a second spot. The array-immobilized genomic nucleic acid segments in a spot can be non-overlapping in sequence compared to the array-immobilized genomic nucleic acid segments in about 25%, 30%, 35%, 40%, 45%, 50%, 55%, 60%, 65%, 70%, 75%, 80%, 85%, 90%, 95%, 98%, 99%, or more or all of other genomic nucleic acid-comprising spots on the array.

In one aspect, at least one cloned genomic nucleic acid segment is spotted in duplicate or triplicate on the array. All the duplicate spot(s) or triplicate spot(s) can have a different amount of nucleic acids segments immobilized. In alternative aspects, about 25%, 30%, 35%, 40%, 45%, 50%, 55%, 60%, 65%, 70%, 75%, 80%, 85%, 90%, 95%, 98%, 99%, or more or all the cloned genomic nucleic acid segments are spotted in duplicate or triplicate on the array.

In alternative aspects, about 25%, 30%, 35%, 40%, 45%, 50%, 55%, 60%, 65%, 70%, 75%, 80%, 85%, 90%, 95%, 98%, 99%, or more or all of the array-immobilized genomic nucleic acid comprise a detectable label.

In one aspect, the array-immobilized genomic nucleic acids are covalently bound to the substrate surface. The array-immobilized genomic nucleic acid can be covalently bound to a compound having the general formula: R1-X—R2, wherein R1 is a cyclic ether, an aldehyde, or a chloromethylphenyl moiety; X is a moiety chemically suitable for linking the R1 moiety to the R2 moiety, and the R2 moiety has the general formula

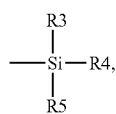

wherein R3, R4 and R5 comprise identical or different alkoxy group or chloro groups.

The array-immobilized genomic nucleic acid can be covalently bound to a compound having the general formula: R1-X—R2, wherein R1 is an amino group, R2 is an alkoxysilane group or a chlorohalide group; and X is a moiety chemically suitable for linking the R1 group and the R2 group. The array-immobilized genomic nucleic acid can be covalently bound to a compound having the general formula

wherein m+k is the integer 3, and n can be 0 if m is greater than 0, or n+k is the integer 3 and m can be 0 if n is greater than 0; X is an inert linker; R1 comprises a group reactive toward the biological molecule; R is an alkyl group; and, R2 is an alkyl group.

In one aspect, the cloned nucleic acid segment is cloned in a construct comprising an artificial chromosome, wherein the artificial chromosome can comprise a bacterial artificial chromosome (BAC), a human artificial chromosome (HAC) a yeast artificial chromosome (YAC), a transformation-competent artificial chromosome (TAC) or a bacteriophage P1-derived artificial chromosome (PAC). In one aspect, the cloned nucleic acid segment is cloned in a construct comprising a vector selected from the group consisting of a cosmid vector, a plasmid vector and a viral vector.

In alternative aspects, the cloned nucleic acid segment is between about 50 kilobases (0.5 megabase) to about 500 kilobases (5 megabases) in length, between about 100 kilobases (1 megabase) to about 400 kilobases (4 megabases) in length, and is about 0.5, about 1, about 2, about 5, about 10, about 15, about 25, about 50, about 100, about 200, about 300, about 400, about 500 or about 600 kilobases in length.

The invention provides an articles of manufacture (e.g., arrays) for the detection of a chromosomal abnormality or the diagnosis of a syndrome associated with a contiguous gene abnormality, comprising: a plurality of nucleic acids segments, wherein each nucleic acid is immobilized to a discrete and known spot on a substrate surface to form an array of nucleic acids, and each spot comprises a segment of genomic nucleic acid associated with a chromosomal abnormality, a contiguous gene abnormality, a genetically linked disease or a syndrome, and the plurality of nucleic acids segments comprise: chromosome 1, locus 1p36, wherein the syndrome detected is 1p Deletion Syndrome; chromosome 3, locus 3p25-pter, wherein the syndrome detected is 3p Deletion Syndrome; chromosome 3, locus 3p21-pter, wherein the syndrome detected is 3p Duplication Syndrome; chromosome 4, locus 4p16.3, wherein the syndrome detected is Wolf-Hirschhorn Syndrome; chromosome 4, locus 4p15.2-16.1, wherein the syndrome detected is 4p Duplication Syndrome; chromosome 5, locus 5p15.2-pter, wherein the syndrome detected is Cri du Chat Syndrome; chromosome 7, locus 7p13.3, wherein the syndrome detected is Miller-Dieker Syndrome; chromosome 7, locus 7q11.23, wherein the syndrome detected is William's Syndrome; chromosome 8, locus 8q24.1, wherein the syndrome detected is Langer-Giedion Syndrome (LGS); chromosome 8, locus 8q24.1, wherein the syndrome detected is Trichorhinophalangeal Syndrome (TRPS); chromosome 9, locus 9p, wherein the syndrome detected is 9p Deletion Syndrome; chromosome 10, locus 10p13-p14, wherein the syndrome detected is DiGeorge Syndrome II; chromosome 11, locus 11p13, wherein the syndrome detected is WAGR Syndrome; chromosome 11, locus 11p15.5, wherein the syndrome detected is Beckwith-Wiedemann Syndrome; chromosome 11, locus 11p11.2, wherein the syndrome detected is Potocki-Shaffer Syndrome (Multiple Exostoses II Locus); chromosome 15, locus 15q12, wherein the syndrome detected is Angelman Syndrome; chromosome 15, locus 15q12, wherein the syndrome detected is Prader-Willi Syndrome; chromosome 16, locus distal 16p13.3, wherein the syndrome detected is Rubinstein-Taybi Syndrome; chromosome 17, locus 17p12, wherein the syndrome detected is Charcot-Marie-Tooth Disease Type 1A(CMT-1A); chromosome 17, locus 17p12, wherein the syndrome detected is Hereditary Neuropathy with Liability to Pressure Palsies; chromosome 17, locus 17p13.3, wherein the syndrome detected is Miller-Dieker Syndrome/Isolated Lissencephaly; chromosome 17, locus 17p11.2, wherein the syndrome detected is Smith-Magenis Syndrome; chromosome 20, locus 20p11.2-p12, wherein the syndrome detected is Alagille Syndrome; chromosome 22, locus 22q11.2, wherein the syndrome detected is Digeorge/Velocardiofacial Syndrome; chromosome X, locus Xp21, wherein the syndrome detected is Adrenal Hypoplasia Congenita (AHC); chromosome X, locus Xp21, wherein the syndrome detected is Duchenne/Becker Muscular Dystrophy; chromosome X, locus Xp21, wherein the syndrome detected is Glycerol Kinase Deficiency; chromosome X, locus Xp22, wherein the syndrome detected is Pelizaeus-Merzbacher Disease; chromosome X, locus Xp22.3, wherein the syndrome detected comprises steroid sulfatase deficiency; chromosome Y, locus SRY locus/Yp, wherein the syndrome detected comprises abnormalities of the SRY locus; chromosome X, locus Xp22.3, and the syndrome detected is Kallman Disease; chromosome X, locus Xp21, and the syndrome detected is Sex Reversal (DSS); and, chromosome 17, locus 17p11.2, and the syndrome detected is 17p11.2 Duplication Syndrome.

The invention provides an articles of manufacture (e.g., arrays) for the detection of a chromosomal abnormality or the diagnosis of a syndrome associated with a contiguous gene abnormality comprising a plurality of nucleic acids segments, wherein each nucleic acid segment is immobilized to a discrete and known spot on a substrate surface to form an array of nucleic acids, and the nucleic acid segments are selected from the group consisting of chromosome 1, locus 1p36; chromosome 3, locus 3p25-pter; chromosome 3, locus 3p21-pter; chromosome 4, locus 4p16.3; chromosome 4, locus 4p15.2-16.1; chromosome 5, locus 5p15.2-pter; chromosome 7, locus 7p13.3; chromosome 7, locus 7q11.23; chromosome 8, locus 8q24.1; chromosome 8, locus 8q24.1; chromosome 9, locus 9p; chromosome 10, locus 10p13-p14; chromosome 11, locus 11p13; chromosome 11, locus 11p15.5; chromosome 11, locus 11p11.2; chromosome 15, locus 15q12; chromosome 16, locus distal 16p13.3; chromosome 17, locus 17p12; chromosome 17, locus 17p13.3; chromosome 17, locus 17p11.2; chromosome 20, locus 20p11.2-p12; chromosome 22, locus 22q11.2; chromosome X, locus Xp21; chromosome X, locus Xp22; chromosome X, locus Xp22.3; and, chromosome Y, locus SRY locus/Yp. In alternative aspects, an array of the invention comprises at least 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39 and 40 members of this group of nucleic acid segments.

In alternative aspects, the articles of manufacture (arrays) of the invention further comprising at least one spot comprising a nucleic acid segment acting as a positive control, at least one spot comprising a nucleic acid segment acting as a negative control, or, the array includes positive control and negative control spots.

The invention provides a method of detecting a chromosomal abnormality or for diagnosis of a syndrome associated with a contiguous gene abnormality in an individual comprising the following steps: (a) providing an article of manufacture (array) of the invention; (b) providing a sample comprising a substantially full complement of genomic DNA from the individual; (c) contacting the genomic DNA of step (b) or a nucleic acid comprising a sequence equivalent to the genomic DNA of step (b) with the article of manufacture under conditions wherein the nucleic acid in the sample can specifically hybridize to the genomic nucleic acid segments immobilized on the article of manufacture; (g) measuring the location and amount of genomic DNA specifically hybridized to the genomic nucleic acid segments immobilized on the article of manufacture, thereby detecting a chromosomal abnormality or making a diagnosis of a syndrome associated with a contiguous gene abnormality in an individual. In one aspect, detecting the chromosomal abnormality in the individual can detect a disease or a condition or a syndrome in the individual. In alternative aspects, individual can be a human, an embryo, a fetus.

In one aspect, the individual is suspected of having a chromosomal abnormality. The individual can be suspected of having a disease or condition associated with a karyotype abnormality. The disease can comprise a cancer. The sample can comprise a body fluid sample, a cell sample or a tissue sample. The sample can comprise a cancer cell or a tumor cell sample. The sample can be a biopsy sample, a blood sample, a urine sample, a cerebral spinal fluid (CSF) sample, an amniotic fluid sample, a chorionic villus sample, or an embryonic cell or embryo tissue sample.

The method can further comprise associating the sample nucleic acid or the nucleic acid immobilized to the article of manufacture with a detectable label. The detectable label can be covalently associated with the nucleic acid. The detectable label can comprise a fluorescent label, e.g., a Cy5™ or equivalent, a Cy3™ or equivalent, a rhodamine, a fluorescein or an aryl-substituted 4,4-difluoro-4-bora-3a, 4a-diazas-indacene dye or equivalents.

In alternative aspects of the method, the labeling of the nucleic acid segments comprises random prime labeling and nick translation labeling.

In alternative aspects of the method, about 25%, 30%, 35%, 40%, 45%, 50%, 55%, 60%, 65%, 70%, 75%, 80%, 85%, 90%, 95%, 98%, 99%, or all of the array-immobilized genomic nucleic acid comprises a detectable label.

The methods can comprise use of a device that can detect a detectable label. The device can measure which spots on the substrate surface are associated with a detectable label. The device can measure how much detectable label is on which spot on the substrate surface. The device can comprise a charge-coupled device (CCD). The device can be capable of multicolor fluorescence imaging.

The methods of the invention, or, the articles of manufacture (arrays) of the invention, can further comprise a computer processor to analyze multicolor fluorescence imaging data. The method, or, the arrays of the invention, also can further comprise use of a computer and a computer program algorithm to interpret data imaged from the array and display results.

The methods of the invention can further comprising a washing step, wherein nucleic acid in the sample not specifically hybridized to the genomic nucleic acid segments immobilized on the array are removed. In alternative aspects, the washing step comprises use of a solution comprising a salt concentration of about 0.02 molar at pH 7 at a temperature of at least about 50° C.; the washing step comprises use of a solution comprising a salt concentration of about 0.15 M at a temperature of at least about 72° C. for about 15 minutes; and, the washing step comprises use of a solution comprising a salt concentration of about 0.2×SSC at a temperature of at least about 50° C. for at least about 15 minutes. Further exemplary methods are set forth below.

The method of the invention can further comprise steps for a comparative genomic hybridization (CGH), the method further comprising: associating the nucleic acid in the first sample of step (b) with a detectable label; providing a second sample comprising nucleic acid complementary to a substantially complete genome, wherein the nucleic acid comprises a detectable label distinguishable from the detectable label associated with the first sample genomic nucleic acid, and the karyotype of the genome of the second sample is known; contacting the array with the nucleic acid of the first sample and the nucleic acid of the second sample under conditions wherein the nucleic acid of the samples can specifically hybridize to the array-immobilized nucleic acid; measuring the location and amount of nucleic acid from the first and second sample specifically hybridized to the genomic nucleic acid segments immobilized on the array, thereby performing a comparative genomic hybridization. The nucleic acid from the first and the second sample can be from the same individual (e.g., wherein the samples are taken at different times, or from different tissues or fluids), from related individuals, from the same species, related species or different or unrelated species. The nucleic acid from the first and the second sample can be from a human sample. The substantially complete genome of the second sample can comprise a wild type genome, e.g., a genome substantially or completely lacking a known contiguous gene abnormality.

The invention provides a kit comprising the following components: (a) an article of manufacture (e.g., an array) for the detection of a chromosomal abnormality or a diagnosis of a syndrome associated with a contiguous gene abnormality, comprising a plurality of nucleic acids segments, wherein each nucleic acid is immobilized to a discrete and known spot on a substrate surface to form an array of nucleic acids, and each spot comprises a segment of genomic nucleic acid associated with a chromosomal abnormality, a contiguous gene abnormality, a genetically linked disease or a syndrome; and, (b) instructions for using the array to detect a chromosomal abnormality.

In alternative aspects, the kit further comprises materials to prepare a sample comprising a genomic nucleic acid for application to the array; materials to label the sample genomic nucleic acid; a sample of wild type genomic nucleic acid, or any genomic nucleic acid of known karyotype, or any combination or all of these.

In one aspect of the kit, the wild type genomic nucleic acid is labeled. The wild type genomic nucleic acid can comprise a label different (e.g., distinguishable) from that used to label the sample genomic nucleic acid. The wild type genomic nucleic acid can comprise a human wild type genomic nucleic acid.

The invention provides compilations (i.e., a libraries, sets (such as a clone set) or collections) of nucleic acids for the detection of a chromosomal abnormality or for the diagnosis or prognosis of a syndrome associated with a contiguous gene abnormality, comprising a plurality of nucleic acids segments, wherein each nucleic acid segment comprises a segment of genomic nucleic acid associated with a chromosomal abnormality, a contiguous gene abnormality, a genetically linked disease or a syndrome. The segment of genomic nucleic acid can be derived from a cloned copy of a genome, an amplified copy of a genome, an isolated copy of a genome, a completely artificial copy of a sequence of a genome and the like.

In alternative aspects of the compilations (sets, libraries, collections) of nucleic acids of the invention, a segment of genomic nucleic acid comprises chromosome 1, locus 1p;36, and the syndrome detected can be 1p Deletion Syndrome, chromosome 1, locus 1p;36, and the syndrome detected can be 1p Deletion Syndrome; chromosome 1, locus 7p11.2, and the syndrome detected can be Smith-Magenis syndrome (SMS); chromosome 3, locus 3p25-pter, and the syndrome detected can be 3p Deletion Syndrome; chromosome 3, locus 3p21-pter, and the syndrome detected can be 3p Duplication Syndrome; chromosome 4, locus 4p16.3, and the syndrome detected can be Wolf-Hirschhorn Syndrome; chromosome 4, locus 4p15.2-16.1, and the syndrome detected can be 4p Duplication Syndrome; chromosome 5, locus 5p15.2-pter, and the syndrome detected can be Cri du Chat Syndrome; chromosome 7, locus 7p13.3, and the syndrome detected can be Miller-Dieker Syndrome; chromosome 7, locus 7q11.23, and the syndrome detected can be Williams Syndrome; chromosome 8, locus 8q24.1, and the syndrome detected can be Langer-Giedion Syndrome (LGS); chromosome 8, locus 8q24.1, and the syndrome detected can be Trichorhinophalangeal Syndrome (TRPS); chromosome 8, locus 8q13.3, and the syndrome detected can be branchio-oto-renal (BOR) syndrome; chromosome 9, locus 9p, e.g., locus 9p22-pter, and the syndrome detected can be 9p Deletion Syndrome; chromosome 10, locus 10p13-p14, and the syndrome detected can be DiGeorge Syndrome II; chromosome 11, locus 1p13, and the syndrome detected can be WAGR Syndrome; chromosome 11, locus 11p15.5, and the syndrome detected is Beckwith-Wiedemann Syndrome; chromosome 11, locus 11p11.2, and the syndrome detected can be Potocki-Shaffer Syndrome (Multiple Exostoses II Locus); chromosome 13, locus 13q22, and the syndrome detected can be Hirschsprung disease and Waardenburg syndrome; chromosome 15, locus 15q12, and the syndrome detected can be Angelman Syndrome; chromosome 15, locus 15q12, and the syndrome detected can be Prader-Willi Syndrome; chromosome 16, locus distal 16p13.3, and the syndrome detected can be Rubinstein-Taybi Syndrome; chromosome 16, pericentromeric region, and the syndrome detected can be idiopathic epilepsy and paroxysmal dyskinesia; chromosome 17, locus 17p12, and the syndrome detected can be Charcot-Marie-Tooth Disease Type 1A(CMT-1A); chromosome 17, locus 17p12, and the syndrome detected can be Hereditary Neuropathy with Liability to Pressure Palsies; chromosome 17, locus 17p13.3, and the syndrome detected can be Miller-Dieker Syndrome/Isolated Lissencephaly; chromosome 17, locus 17p11.2, and the syndrome detected can be Smith-Magenis Syndrome; chromosome 20, locus 20p11.2-p12, and the syndrome detected can be Alagille Syndrome; chromosome 22, locus 22q11.2, and the syndrome detected can be Digeorge/Velocardiofacial Syndrome; chromosome X, locus Xp21, and the syndrome detected can be Adrenal Hypoplasia Congenita (AHC); chromosome X, locus Xp21, and the syndrome detected can be Duchenne/Becker Muscular Dystrophy; chromosome X, locus Xp21, and the syndrome detected can be Glycerol Kinase Deficiency; chromosome X, locus Xp22, and the syndrome detected can be Pelizaeus-Merzbacher Disease; chromosome X, locus Xp22.3, and the syndrome detected can comprise steroid sulfatase deficiency; chromosome X, locus Xp22.3, and the syndrome detected can be Leri-Weill syndrome; chromosome Y, locus SRY locus/Yp, and the syndrome detected can comprise abnormalities of the SRY locus; chromosome X, locus Xp22.3, and the syndrome detected can be Kallman Disease; chromosome X, locus Xp21, and the syndrome detected can be Sex Reversal (DSS); chromosome 17, locus 17p11.2, and the syndrome detected is 17p11.2 Duplication Syndrome; and, chromosome 17, locus 17p11.2, and the syndrome detected can be Smith-Magenis syndrome (SMS) or any combination or all of these syndromes or conditions. The compilations (libraries, sets, collections) of nucleic acids of the invention can comprise members comprising all or any subset of nucleic acids from these chromosomal segments.

In one aspect, each chromosomal segment is on a different member (nucleic acid segment) of the compilation of the invention. In another aspect, at least one member (nucleic acid segment) of the compilation has two or more of the above-listed chromosomal segments.

In alternative aspects, about 40%, 45%, 50%, 55%, 60%, 65%, 70%, 75%, 80%, 85%, 90%, 95%, 96%, 97%, 98%, or 99% or more of the nucleic acid segments associated with a chromosomal abnormality, a contiguous gene abnormality, a genetically linked disease or a syndrome. In one aspect, the nucleic acid segments are derived from genomic nucleic acid. In one aspect, 100% of the nucleic acid segments are associated with a chromosomal abnormality, a contiguous gene abnormality, a genetically linked disease or a syndrome or comprise a segment of genomic nucleic acid associated with a chromosomal abnormality, a contiguous gene abnormality, a genetically linked disease or a syndrome.

In one aspect, the nucleic acids segments are immobilized onto a substrate surface (a substrate means). Any substrate surface can be used, e.g., a solid surface such as nitrocellulose, glass, quartz, fused silica, plastics and the like, or a semi-solid surface. The substrate surfaces can be flat or planar, be shaped as wells, capillary tubes, raised regions, etched trenches, pores, beads, filaments, or the like. The nucleic acid segments can be immobilized on a surface as an array.

In alternative aspects, about 40%, 45%, 50%, 55%, 60%, 65%, 70%, 75%, 80%, 85%, 90%, 95%, 96%, 97%, 98%, or 99% or more or all of the nucleic acid segments comprise a detectable label.

In one aspect, the nucleic acid segments further comprise a compound having the general formula: $R_1$—X—$R_2$, wherein $R_1$ is a cyclic ether, an aldehyde, or a chloromethylphenyl moiety; X is a moiety chemically suitable for linking the $R_1$ moiety to the $R_2$ moiety, and the $R_2$ moiety has the general formula

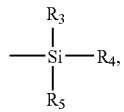

wherein $R_3$, $R_4$ and $R_5$ comprise identical or different alkoxy group or chloro groups.

In one aspect, the nucleic acid segments further comprise a compound having the general formula: $R_1$—X—$R_2$, wherein $R_1$ is an amino group, $R_2$ is an alkoxysilane group or a chlorohalide group; and X is a moiety chemically suitable for linking the $R_1$ group and the $R_2$ group.

In one aspect, the nucleic acid segments further comprise a compound having the general formula $$R_1\text{—}X\text{—}Si(OR_2)_m(Cl)_n(R)_k,$$

wherein m+k is the integer 3, and n can be 0 if m is greater than 0, or n+k is the integer 3 and m can be 0 if n is greater than 0; X is an inert linker; R1 comprises a group reactive toward the biological molecule; R is an alkyl group; and, $R_2$ is an alkyl group.

In one aspect, at least one nucleic acid segment is cloned in a cloning vehicle, e.g., a construct comprising an artificial chromosome. The artificial chromosome comprises a bacterial artificial chromosome (BAC), a human artificial chromosome (HAC) a yeast artificial chromosome (YAC), a transformation-competent artificial chromosome (TAC) and a bacteriophage P1-derived artificial chromosome (PAC) and the like. In one aspect, at least one nucleic acid segment is cloned in a construct comprising a vector selected from the group consisting of a cosmid vector, a plasmid vector and a viral vector.

In alternative aspects, the nucleic acid segments are between about 15 kilobases (0.15 megabase) to about 1000 kilobases (10 megabases) in length, 25 kilobases (0.25 megabase) to about 750 kilobases (7.5 megabases) in length, 50 kilobases (0.5 megabase) to about 500 kilobases (5 megabases) in length, between about 100 kilobases (1 megabase) to about 400 kilobases (4 megabases) in length, between about 150 kilobases (1.5 megabase) or about 300 kilobases (3 megabases) in length.

In one aspect, the compilation (or libraries, or sets, or collections) of nucleic acids can be used for the detection of a chromosomal abnormality or the diagnosis or prognosis of a syndrome associated with a contiguous gene abnormality. The compilation (or libraries, or sets, or collections can comprise a plurality of nucleic acid segments associated with a chromosomal abnormality, a contiguous gene abnormality, a genetically linked disease or a syndrome. In one aspect, the plurality of nucleic acids segments comprise chromosome 1, locus 1p36, wherein the syndrome detected can be 1p Deletion Syndrome; chromosome 3, locus 3p25-pter, wherein the syndrome detected can be 3p Deletion Syndrome; chromosome 3, locus 3p21-pter, wherein the syndrome detected can be 3p Duplication Syndrome; chromosome 4, locus 4p16.3, wherein the syndrome detected can be Wolf-Hirschhorn Syndrome; chromosome 4, locus 4p15.2-16.1, wherein the syndrome detected can be 4p Duplication Syndrome; chromosome 5, locus 5p15.2-pter, wherein the syndrome detected can be Cri du Chat Syndrome; chromosome 7, locus 7p13.3, wherein the syndrome detected can be Miller-Dieker Syndrome; chromosome 7, locus 7q11.23, wherein the syndrome detected can be William's Syndrome; chromosome 8, locus 8q24.1, wherein the syndrome detected can be Langer-Giedion Syndrome (LGS); chromosome 8, locus 8q24.1, wherein the syndrome detected can be Trichorhinophalangeal Syndrome (TRPS); chromosome 9, locus 9p, wherein the syndrome detected can be 9p Deletion Syndrome; chromosome 10, locus 10p13-p14, wherein the syndrome detected can be DiGeorge Syndrome II; chromosome 11, locus 11p13, wherein the syndrome detected can be WAGR Syndrome; chromosome 11, locus 11p15.5, wherein the syndrome detected can be Beckwith-Wiedemann Syndrome; chromosome 11, locus 11p11.2, wherein the syndrome detected can be Potocki-Shaffer Syndrome (Multiple Exostoses II Locus); chromosome 15, locus 15q12, wherein the syndrome detected can be Angelman Syndrome; chromosome 15, locus 15q12, wherein the syndrome detected can be Prader-Willi Syndrome; chromosome 16, locus distal 16p13.3, wherein the syndrome detected can be Rubinstein-Taybi Syndrome; chromosome 17, locus 17p12, wherein the syndrome detected can be Charcot-Marie-Tooth Disease Type 1A(CMT-1A); chromosome 17, locus 17p12, wherein the syndrome detected can be Hereditary Neuropathy with Liability to Pressure Palsies; chromosome 17, locus 17p13.3, wherein the syndrome detected can be Miller-Dieker Syndrome/Isolated Lissencephaly; chromosome 17, locus 17p11.2, wherein the syndrome detected can be Smith-Magenis Syndrome; chromosome 20, locus 20p11.2-p12, wherein the syndrome detected can be Alagille Syndrome; chromosome 22, locus 22q11.2, wherein the syndrome detected can be Digeorge/Velocardiofacial Syndrome; chromosome X, locus Xp21, wherein the syndrome detected can be Adrenal Hypoplasia Congenita (AHC); chromosome X, locus Xp21, wherein the syndrome detected can be Duchenne/Becker Muscular Dystrophy; chromosome X, locus Xp21, wherein the syndrome detected can be Glycerol Kinase Deficiency; chromosome X, locus Xp22, wherein the syndrome detected can be Pelizaeus-Merzbacher Disease; chromosome X, locus Xp22.3, wherein the syndrome detected comprises steroid sulfatase deficiency; chromosome Y, locus SRY locus/Yp, wherein the syndrome detected comprises abnormalities of the SRY locus; chromosome X, locus Xp22.3, and the syndrome detected can be Kallman Disease; chromosome X, locus Xp21, and the syndrome detected can be Sex Reversal (DSS); and, chromosome 17, locus 17p11.2, and the syndrome detected can be 17p11.2 Duplication Syndrome.

A compilation of nucleic acids, wherein each nucleic acid segment is associated with a chromosomal abnormality, a contiguous gene abnormality, a genetically linked disease or a syndrome, and the nucleic acid segments are selected from the group consisting of chromosome 1, locus 1p36; chromosome 3, locus 3p25-pter; chromosome 3, locus 3p21-pter; chromosome 4, locus 4p16.3; chromosome 4, locus 4p15.2-16.1; chromosome 5, locus 5p15.2-pter; chromosome 7, locus 7p13.3; chromosome 7, locus 7q11.23; chromosome 8, locus 8q24.1; chromosome 8, locus 8q24.1; chromosome 9, locus 9p; chromosome 10, locus 10p13-p14; chromosome 11, locus 11p13; chromosome 11, locus 11p15.5; chromosome 11, locus 11p11.2; chromosome 15, locus 15q12; chromosome 16, locus distal 16p13.3; chromosome 17, locus 17p12; chromosome 17, locus 17p13.3; chromosome 17, locus 17p11.2; chromosome 20, locus 20p11.2-p12; chromosome 22, locus 22q11.2; chromosome X, locus Xp21; chromosome X, locus Xp22; chromosome X, locus Xp22.3; and, chromosome Y, locus SRY locus/Yp.

In one aspect, the nucleic acids segments are immobilized onto a substrate surface (a substrate means). Any substrate surface can be used, e.g., a solid surface such as nitrocellulose, glass, quartz, fused silica, plastics and the like, or a semi-solid surface. The substrate surfaces can be flat or planar, be shaped as wells, capillary tubes, raised regions, etched trenches, pores, beads, filaments, or the like. The nucleic acid segments can be immobilized on a surface as an array.

The invention provides methods of detecting a chromosomal abnormality or for the diagnosis or prognosis of a syndrome associated with a contiguous gene abnormality in an individual comprising the following steps: (a) providing a compilation of nucleic acids of the invention; (b) providing a sample comprising a substantially full complement of genomic DNA from the individual; (c) contacting the genomic DNA of step (b) or a nucleic acid comprising a sequence equivalent to the genomic DNA of step (b) with the compilation of nucleic acids of step (a) under conditions wherein the nucleic acid in the sample can specifically hybridize to the compilation of nucleic acids; (g) measuring the location and amount of genomic DNA specifically hybridized to the compilation of nucleic acids of step (a), thereby detecting a chromosomal abnormality or making a diagnosis of a syndrome associated with a contiguous gene abnormality in an individual. In one aspect, detecting the chromosomal abnormality in the individual detects a disease or a condition or a syndrome in the individual. The individual can be a human. The individual can be an embryo.

In one aspect, the individual is suspected of having a chromosomal abnormality. In one aspect, the individual is suspected of having a disease or condition associated with a karyotype abnormality. The disease can comprise a cancer.

In one aspect, the sample comprises a body fluid sample, a cell sample or a tissue sample. The sample can comprise a cancer cell or a tumor cell sample. In one aspect, the sample is a biopsy sample, a blood sample, a urine sample, a cerebral spinal fluid (CSF) sample, an amniotic fluid sample a chorionic villus sample or an embryonic cell or embryo tissue sample.

The method can further comprise associating the sample nucleic acid or the compilation of nucleic acids with a detectable label. The detectable label can be covalently or non-covalently associated with the nucleic acid. The detectable label can comprise a fluorescent label, such as Cy5™ or equivalent or Cy3™ or equivalent. The fluorescent label can comprise a rhodamine, a fluorescein or an aryl-substituted 4,4-difluoro-4-bora-3a, 4a-diaza-s-indacene dye or equivalents.

In one aspect, the labeling of the nucleic acid segments involves random prime labeling or nick translation labeling. In alternative aspects, about 40%, 45%, 50%, 55%, 60%, 65%, 70%, 75%, 80%, 85%, 90%, 95%, 96%, 97%, 98%, or 99% or more or all of the nucleic acid segments comprise a detectable label.

The methods can further comprise use of a device that can detect a detectable label. The device can comprise a charge-coupled device (CCD). The device can be capable of multicolor fluorescence imaging.

The methods can further comprise use of a computer processor to analyze multicolor fluorescence imaging data. The methods can further comprise use of a computer and a computer program algorithm to interpret imaged data and display results.

The methods can further comprise a washing step, wherein nucleic acid in the sample not specifically hybridized to the compilation of nucleic acids are removed. The washing step can comprise use of a solution comprising a salt concentration of about 0.02 molar at pH 7 at a temperature of at least about 50° C. The washing step can comprise use of a solution comprising a salt concentration of about 0.15 M at a temperature of at least about 72° C. for about 15 minutes. The washing step can comprise use of a solution comprising a salt concentration of about 0.2×SSC at a temperature of at least about 50° C. for at least about 15 minutes.

The methods can further comprise associating the nucleic acid in the first sample with a detectable label. The methods can further comprise providing a second sample comprising nucleic acid complementary to a substantially complete genome, wherein the nucleic acid comprises a detectable label distinguishable from the detectable label associated with the first sample genomic nucleic acid, and the karyotype of the genome of the second sample is known. The methods can further comprise contacting the compilation of nucleic acids with the nucleic acid of the first sample and the nucleic acid of the second sample under conditions wherein the nucleic acid of the samples can specifically hybridize to the compilation of nucleic acids. The methods can further comprise measuring the location and amount of nucleic acid from the first and second sample specifically hybridized to the compilation of nucleic acids.

In one aspect, the nucleic acid from the first and the second sample are from the same species. The nucleic acid from the first and the second sample can be from a human sample. In one aspect, the substantially complete genome of the second sample comprises a wild type genome.

The invention provides kits comprising the following components: (a) a compilation of nucleic acids of the invention, e.g., a compilation of nucleic acids comprising a plurality of nucleic acids segments, wherein each nucleic acid is associated with a chromosomal abnormality, a contiguous gene abnormality, a genetically linked disease or a syndrome. In one aspect, the kit comprises instructions for using the compilation of nucleic acids of step (a) to detect a chromosomal abnormality. In the kit, the compilation of nucleic acids can be in one or a plurality of containers, e.g., vials, test tubes and the like. The kits can further comprise materials to prepare a sample comprising a genomic nucleic acid for application to the compilation of nucleic acids, materials to label the sample genomic nucleic acid and/or a sample of wild type genomic nucleic acid. The wild type genomic nucleic acid can be labeled. The wild type genomic nucleic acid can comprise a label different from that used to label the sample genomic nucleic acid. The wild type genomic nucleic acid can comprise a human wild type genomic nucleic acid.

The invention provides a method for selecting a genomic nucleic acid segment for use as a hybridization target in a hybridization reaction, e.g., a comparative genomic hybridization (CGH) reaction, for the detection of a chromosomal aneuploidy comprising (a) selecting a chromosomal segment that hybridizes to a single locus under stringent conditions, wherein the locus comprises a segment of the chromosome comprising the aneuploidy to be detected; (b) selecting a chromosomal segment having at least about 15% to 25% unique sequence not present in the other regions of the genome such that at least 75% to 85% of the sequence within the chromosomal segment is repetitive, except for chromosomal segments from the X chromosome or Y chromosome, which can have up to 90% to 95% repetitive sequences; and (c) selecting a clone selected in both step (a) and step (b), thereby selecting a genomic nucleic acid segment for use as a hybridization target in a comparative genomic hybridization (CGH) reaction for the detection of a chromosomal aneuploidy. In alternative aspects, the method comprises selecting a chromosomal segment having at least about 10%, 15%, 20%, 25% and 30% unique sequence not present in the other regions of the genome.

The invention provides an article of manufacture, e.g., an array, comprising a plurality of nucleic acid segments, wherein each nucleic acid segment comprises the following characteristics: (a) each nucleic acid segment comprises a genomic nucleic acid sequence that hybridizes to a single locus of the genome under stringent conditions; and (b) each nucleic acid segment has at least about 15% to 25% unique sequence not present in the other regions of the genome such that at least 75% to 85% of the sequence within the chromosomal segment is repetitive, except for chromosomal segments from the X chromosome or Y chromosome, which can have up to 90% to 95% repetitive sequences. In alternative aspects, the chromosomal segments have at least about 10%, 15%, 20%, 25% and 30% unique sequence not present in the other regions of the genome.

The invention provides a library, collection, set or compilation of nucleic acid segments, wherein each member of the library, collection, set or compilation comprises the following characteristics: (a) each member of the library comprises a genomic nucleic acid sequence that hybridizes to a single locus of the genome under stringent conditions; and (b) each member of the library has at least about 15% to 25% unique sequence not present in the other regions of the genome such that at least 75% to 85% of the sequence within the chromosomal segment is repetitive in nature, except for chromosomal segments from the X chromosome or Y chromosome, which can have up to 90% to 95% repetitive sequences. In alternative aspects, the nucleic acid segments have at least about 10%, 15%, 20%, 25% and 30% unique sequence not present in the other regions of the genome. The library, collection, set or compilation of nucleic acid segments can be used as hybridization target in comparative genomic hybridization (CGH) reactions for the detection of chromosomal aneuploidies.

The invention provides methods for selecting a genomic nucleic acid segment (e.g., a genomic fragment) for use as a hybridization target in a hybridization reaction, e.g., a comparative genomic hybridization (CGH) reaction, for the detection of a chromosomal abnormality, such as an aneuploidy, an amplification, a deletion and the like, comprising (a) selecting a chromosomal segment that hybridizes to a single locus under stringent conditions (see below, including Examples, for exemplary hybridization conditions), wherein the locus comprises a segment of the chromosome comprising the aneuploidy to be detected; (b) selecting a chromosomal segment having at least about 15% to 25% unique sequence not present in the other regions of the genome such that up to 75% to 85% of the sequence within the chromosomal segment is repetitive, except for chromosomal segments from the X chromosome or Y chromosome, which can have up to 90% to 95% repetitive sequences; and (c) selecting a clone selected in both step (a) and step (b), thereby selecting a genomic nucleic acid segment for use as a hybridization target in a comparative genomic hybridization (CGH) reaction for the detection of a chromosomal aneuploidy. In alternative aspects, the method comprises selecting a chromosomal segment having at least about 10%, 15%, 20%, 25%, 30%, 35%, 40%, 35%, 50%, 55%, 60%, 65%, 70%, 75%, 80%, 85%, 90%, 95% or more unique sequence not present in the other regions of the genome. In alternative aspects, the X chromosome or Y chromosome can have up to 50%, 55%, 60%, 65%, 70%, 75%, 80%, 85%, 90%, 95% or more repetitive sequences.

The invention provides an article of manufacture, e.g., an array, comprising a plurality of nucleic acid segments, wherein each nucleic acid segment comprises the following characteristics: (a) each nucleic acid segment comprises a genomic nucleic acid sequence that hybridizes to a single locus of the genome under stringent conditions; and (b) each nucleic acid segment has at least about 15% to 25% unique sequence not present in the other regions of the genome such that at least 75% to 85% of the sequence within the chromosomal segment is repetitive, except for chromosomal segments from the X chromosome or Y chromosome, which can have up to 90% to 95% repetitive sequences. In alternative aspects, the chromosomal segments can have at least about 10%, 15%, 20%, 25%, 30%, 35%, 40%, 35%, 50%, 55%, 60%, 65%, 70%, 75%, 80%, 85%, 90%, 95% or more unique sequence not present in the other regions of the genome. In alternative aspects, the X chromosome or Y chromosome can have up to 50%, 55%, 60%, 65%, 70%, 75%, 80%, 85%, 90%, 95% or more repetitive sequences.

The invention provides a library, collection, set (e.g., clone set) or compilation of nucleic acid segments, wherein each member of the library, collection, set or compilation comprises the following characteristics: (a) each member of the library comprises a genomic nucleic acid sequence that hybridizes to a single locus of the genome under stringent conditions; and (b) each member of the library has at least about 15% to 25% unique sequence not present in the other regions of the genome such that up to 75% to 85% of the sequence within the chromosomal segment is repetitive in nature, except for chromosomal segments from the X chromosome or Y chromosome, which can have up to 90% to 95% repetitive sequences. In alternative aspects, the nucleic acid segments have at least about 10%, 15%, 20%, 25% and 30% unique sequence not present in the other regions of the genome. The library, collection, set or compilation of nucleic acid segments can be used for multiple purposes, one of which is hybridization target in comparative genomic hybridization (CGH) reactions for the detection of chromosomal aneuploidies. In alternative aspects, the chromosomal segments can have at least about 10%, 15%, 20%, 25%, 30%, 35%, 40%, 35%, 50%, 55%, 60%, 65%, 70%, 75%, 80%, 85%, 90%, 95% or more unique sequence not present in the other regions of the genome. In alternative aspects, the X chromosome or Y chromosome can have up to 50%, 55%, 60%, 65%, 70%, 75%, 80%, 85%, 90%, 95% or more repetitive sequences.

In one aspect, the stringent hybridization conditions comprise post-hybridization washing conditions comprising: pre-warming the following hybridization solutions at 50° C. in individual Petri dishes: 2×SSC, 50% deionized formamide, 2×SSC, 0.1% NP-40, 0.2×SSC; soaking the array (e.g., a slide) in 2×SSC, 0.5% SDS briefly at room temperature (RT), or alternatively, just 2×SSC can be used; transfering the array (slide) to the pre-warmed 2×SSC, 50% formamide; washing the slides by incubating in the shaking incubator at 50° C. for 20 minutes. In one aspect, the post-hybridization washing conditions comprise repeating the wash using a pre-warmed 2×SSC, 0.1% NP-40. In one aspect, the post-hybridization washing conditions comprise repeating the wash using a pre-warmed 0.2×SSC for 10 minutes. In one aspect, the post-hybridization washing conditions comprise rinsing the slides with distilled deionized water. In one aspect, this last wash does not exceed 10 seconds. In one aspect, the arrays (slides) are immediately dried under forced air.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits cited herein are hereby expressly incorporated by reference for all purposes.

DETAILED DESCRIPTION

The invention provides novel compilations, or sets (e.g., clone sets), libraries or collections, of nucleic acids and articles of manufacture, e.g., arrays. Also provided are methods of making and using them. In one aspect, these compilations, or sets, libraries or collections, of nucleic acids and arrays are used in the detection of a chromosomal abnormality, such as a chromosomal aneuploidy (an abnormality involving a chromosome number that is not an exact multiple of the haploid number). They can also be used in the diagnosis or prognosis of a syndrome associated with a contiguous gene abnormality.

The invention provides novel compilations, or sets, libraries or collections, of nucleic acids and arrays and methods for the detection of a chromosomal abnormality or a diagnosis or prognosis of a syndrome associated with a contiguous gene abnormality. These compilations, or sets, libraries or collections, of nucleic acids and/or arrays can be used for routine or directed genetic screening of embryos, fetuses, children or adults. These compilations, or sets, libraries or collections, of nucleic acids and/or arrays can be used to aid in the diagnosis or prognosis of a syndrome, particularly when it is suspected that a patient may have symptoms associated with one or more chromosomal abnormalities, but those symptoms are not definitively diagnostic. Screening of individuals before symptoms appear will allow preventative or prophylactic treatment regimes.

The invention provides methods for selecting genomic fragments, or clone sets (including, e.g., libraries, collections or compilations of fragments or clones), that are effective as hybridization targets in the detection of chromosomal abnormalities, such as aneuploidies (i.e., abnormalities involving a chromosome number that is not an exact multiple of the haploid number), amplification, deletions and the like. In one aspect, these libraries, collections or compilations of genomic fragments or clones are immobilized on articles of manufacture, e.g., arrays. In one aspect, articles of manufacture, e.g., arrays, comprising these libraries, collections or compilations of genomic fragments or clones (e.g., clone sets) are used to perform comparative genomic hybridization (CGH) to detect chromosomal aneuploidies.

The selection process comprises selection of any clone containing a specific region of the chromosome that only hybridizes to a single locus (e.g., in silico and/or in situ). This insures specificity. The selection process can also comprise selection of chromosome fragments (e.g., clones) containing a fragment of the genome containing at least 15% unique sequences, i.e., sequences that are not present in the other regions of the genome. In other words, in one aspect, it allows up to 85% of the sequence within the fragment to be repetitive in nature, except for X chromosome and Y chromosome fragments (e.g., clones) (alternative aspects allow up to between about 30% to 95% or 99% of the sequence within the fragment to be repetitive). The X chromosome and Y chromosome segments can be up to 90% to 95% repetitive (alternative aspects allow up to between about 50% to 95% or 99% of the sequence within the X chromosome and Y chromosome fragments to be repetitive). In one aspect, selection process comprises both of these steps, i.e., selection of chromosome fragments (e.g., clones) containing a specific region of a chromosome that only hybridize to a single locus and chromosome fragments (e.g., clones) containing a fragment of the genome containing at least 15% unique sequences.

In aspect, the article of manufacture, e.g., array, comprises up to about 2500 (in one aspect, 2474) chromosome fragments (e.g., clones) selected by this method, for example, as described below. The genomic clones can be BAC, PAC, MAC, plasmids, recombinant viruses or phagemids and/or cosmids and the like. In one aspect, the selected chromosome fragments (e.g., clones) are cross-linked (immobilized) to a solid surface, e.g., an article of manufacture such as an array. In one aspect, the selected chromosome fragments (e.g., clones) are immobilized as described in U.S. Pat. No. 6,048,695. The article of manufacture can be an array comprising the selected chromosome fragments (e.g., clones) immobilized on a glass slide. In one aspect, the slide is hybridized with fluorescently labeled test and control target DNA. In aspect, the libraries, collections or compilations of fragments or clones of the invention comprise up to about 2500 (in one aspect, 2474) chromosome fragments (e.g., clones) selected by this method, for example, as described below.

In one aspect, the articles of manufacture, e.g., arrays, comprise a plurality of nucleic acids segments immobilized on a surface, for example, as an array, or "biochip," as they are sometimes called. As is typical of an array or array-like format, each segment can be immobilized onto a discrete and known area, or "spot," on the array. Each "spot" comprises a segment of genomic nucleic acid associated with a chromosomal abnormality, a contiguous gene abnormality, a genetically linked disease or a syndrome. In one aspect, while there may be many nucleic acids molecules immobilized on a particular spot, there is only one specie or representation of a genomic nucleic acid segment associated with a chromosomal abnormality per spot. All of the spots of the array of the invention can include genomic nucleic acid segment associated with a chromosomal abnormalities. In alternative embodiments, as noted above, varying subpopulations of array spots can comprise such genomic nucleic acid segments. Some spots can include nucleic acid segments that serve as positive and negative controls; in one aspect, the test samples are "spiked" with known types and amounts of nucleic acids to serve as positive and negative controls.

Also provided are kits comprising the compilations, or sets, libraries or collections, of nucleic acids and/or arrays of the invention. The kits can include instructions for use of the compilations, or sets, libraries or collections, of nucleic acids and/or arrays and practicing the methods of the invention, and, for the convenience of the practitioner, materials for extracting genomic DNA from a sample and preparing that DNA, including labeling of the genomic nucleic acid. In one aspect, the kits can also include labeled "wild type" genomic nucleic acid, e.g., human genomic nucleic acid that is "wild type," or genomic nucleic acid not known to have any or substantially having no chromosomal abnormalities and/or any contiguous gene abnormalities. The "wild type" genomic nucleic acid can comprise a substantially complete genome; which is useful if the practitioner will be performing a comparative genomic hybridization (CGH).

Definitions

Unless defined otherwise, all technical and scientific terms used herein have the meaning commonly understood by a person skilled in the art to which this invention belongs. As used herein, the following terms have the meanings ascribed to them unless specified otherwise.

The terms "array" or "microarray" or "DNA array" or "nucleic acid array" or "chip" or "biochip" as used herein is a plurality of target elements, each target element comprising a defined amount of one or more biological molecules, e.g., genomic nucleic acid segments, immobilized on a defined location on a substrate surface; as described in further detail, below.

The term "aryl-substituted 4,4-difluoro-4-bora-3a, 4a-diaza-s-indacene dye" as used herein includes all "boron dipyrromethene difluoride fluorophore" or "BODIPY" dyes and "dipyrromethaneboron difluoride dyes" (see, e.g., U.S. Pat. No. 4,774,339), or equivalents, are a class of fluorescent dyes commonly used to label nucleic acids for their detection when used in hybridization reactions; see, e.g., Chen (2000) J. Org Chem. 65:2900-2906: Chen (2000) J. Biochem. Biophys. Methods 42:137-151. See also U.S. Pat. Nos. 6,060,324; 5,994,063; 5,614,386; 5,248,782; 5,227,487; 5,187,288.

The terms "cyanine 5" or "Cy5™" and "cyanine 3" or "Cy3™" refer to fluorescent cyanine dyes produced by Amersham Pharmacia Biotech (Piscataway, N.J.) (Amersham Life Sciences, Arlington Heights, Ill.), as described in detail, below, or equivalents. See U.S. Pat. Nos. 6,027,709; 5,714,386; 5,268,486; 5,151,507; 5,047,519. These dyes are typically incorporated into nucleic acids in the form of 5-amino-propargyl-2'-deoxycytidine 5'-triphosphate coupled to Cy5™ or Cy3™.

The terms "fluorescent dye" and "fluorescent label" as used herein includes all known fluors, including rhodamine dyes (e.g., tetramethylrhodamine, dibenzorhodamine, see, e.g., U.S. Pat. No. 6,051,719); fluorescein dyes; "BODIPY" dyes and equivalents (e.g., dipyrrometheneboron difluoride dyes, see, e.g., U.S. Pat. No. 5,274,113); derivatives of 1-[isoindolyl]methylene-isoindole (see, e.g., U.S. Pat. No. 5,433,896); and all equivalents. See also U.S. Pat. Nos. 6,028,190; 5,188,934.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which one nucleic acid will hybridize preferentially to second sequence (e.g., a sample genomic nucleic acid hybridizing to an immobilized nucleic acid probe in an array), and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions as used herein can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Those of ordinary skill will readily recognize that alternative but comparable hybridization and wash conditions can be utilized to provide conditions of similar stringency.

However, the selection of a hybridization format is not critical, as is known in the art, it is the stringency of the wash conditions that set forth the conditions which determine whether a soluble, sample nucleic acid will specifically hybridize to an immobilized nucleic acid. Wash conditions can include, e.g.: a salt concentration of about 0.02 molar at pH 7 and a temperature of at least about 50° C. or about 55° C. to about 60° C.; or, a salt concentration of about 0.15 M NaCl and a temperature of at least about 72° C. for at least about 15 minutes; or, a salt concentration of about 0.2×SSC at a temperature of at least about 50° C. or about 55° C. to about 60° C. for at least about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. See Sambrook, Ausubel, or Tijssen (cited herein) for detailed descriptions of equivalent hybridization and wash conditions and for reagents and buffers, e.g., SSC buffers and equivalent reagents and conditions.

The phrase "labeled with a detectable composition" or "labeled with a detectable moiety" as used herein refers to a nucleic acid comprising a detectable composition, i.e., a label, as described in detail, below. The label can also be another biological molecule, as a nucleic acid, e.g., a nucleic acid in the form of a stem-loop structure as a "molecular beacon," as described below. This includes incorporation of labeled bases (or, bases which can bind to a detectable label) into the nucleic acid by, e.g., nick translation, random primer extension, amplification with degenerate primers, and the like. The label can be detectable by any means, e.g., visual, spectroscopic, photochemical, biochemical, immunochemical, physical or chemical means. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin.

The term "nucleic acid" as used herein refers to a deoxyribonucleotide or ribonucleotide in either single- or double-stranded form. The term encompasses nucleic acids containing known analogues of natural nucleotides. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The term nucleic acid is used interchangeably with gene, DNA, RNA, cDNA, mRNA, oligonucleotide primer, probe and amplification product.

The term "genomic DNA" or "genomic nucleic acid" includes nucleic acid isolated from a nucleus of one or more cells, and, includes nucleic acid derived from (e.g., isolated from, amplified from, cloned from, synthetic versions of) genomic DNA. The genomic DNA can be from any source, as discussed in detail, below. The term "wild type genomic nucleic acid" means a sample of genomic nucleic acid having no known or substantially no known contiguous gene abnormalities.

The term "a sample comprising a nucleic acid" or "sample of nucleic acid" as used herein refers to a sample comprising a DNA or an RNA, or nucleic acid representative of DNA or RNA isolated from a natural source, in a form suitable for hybridization (e.g., as a soluble aqueous solution) to another nucleic acid or polypeptide or combination thereof (e.g., immobilized probes). The nucleic acid may be isolated, cloned or amplified; it may be, e.g., genomic DNA, episomal DNA, mitochondrial DNA, mRNA, or cDNA; it may be a genomic segment that includes, e.g., particular promoters, enhancers, coding sequences, and the like; it may also include restriction fragments, cDNA libraries or fragments thereof, etc. The nucleic acid sample may be extracted from particular cells, tissues or body fluids, or, can be from cell cultures, including cell lines, or from preserved tissue sample, as described in detail, below.

As used herein, the terms "computer" and "processor" are used in their broadest general contexts and incorporate all such devices. The methods of the invention can be practiced using any computer/processor and in conjunction with any known software or methodology. For example, a computer/processor can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage.

Generating and Manipulating Nucleic Acids

Making and using the compilations, or sets, libraries or collections, of nucleic acids and/or arrays of the invention, and practicing the methods of the invention may involve the isolation, synthesis, cloning, amplification, labeling and hybridization (e.g., CGH) of nucleic acids. As described herein, the compilations, or sets, libraries or collections, of nucleic acids, the nucleic acid for analysis and the immobilized nucleic acid on the array can be representative of genomic DNA, including defined parts of, or entire, chromosomes, or entire genomes. Comparative genomic hybridization (CGH) reactions, see, e.g., U.S. Pat. Nos. 5,830,645; 5,976,790, are discussed in further detail, below. Nucleic acid samples, the compilations, or sets, libraries or collections, of nucleic acids and, in some aspects, immobilized nucleic acids, can be labeled with a detectable moiety, e.g., a fluorescent dye(s) or equivalent. For example, a first sample can be labeled with a fluor and a second sample labeled with a second dye (e.g., Cy3™ and Cy5™). In one aspect, each sample nucleic acid is labeled with at least one different detectable moiety, e.g., different fluorescent dyes, than those used to label the other samples of nucleic acids.

In some cases, the nucleic acids may be amplified using standard techniques such as PCR. Amplification can also be used to subclone or label the nucleic acid prior to the hybridization. The sample and/or the immobilized nucleic acid can be labeled, as described herein. The sample or the probe on the array an be produced from and collectively can be representative of a source of nucleic acids from one or more particular (pre-selected) portions of, e.g., a collection of polymerase chain reaction (PCR) amplification products, substantially an entire chromosome or a chromosome fragment, or substantially an entire genome, e.g., as a collection of clones, e.g., BACs, PACs, YACs, and the like (see below). The array-immobilized nucleic acid or genomic nucleic acid sample may be processed in some manner, e.g., by blocking or removal of repetitive nucleic acids or by enrichment with selected nucleic acids.

In one aspect, samples are applied to the immobilized probes (e.g., on the array) and, after hybridization and washing, the location (e.g., spots on the array) and amount of each dye are read. The compilations, or sets, libraries or collections, of nucleic acids or plurality of immobilized nucleic acid segments can be representative of any segment of genomic nucleic acid associated with a chromosomal abnormality, a contiguous gene abnormality, a genetically linked disease or a syndrome; including, e.g., part of or all of a chromosome or genome. The compilations, or sets, libraries or collections, of nucleic acids or array-immobilized nucleic acid can be in the form of cloned DNA, e.g., YACs, BACs, PACs, and the like, as described herein. As is typical of array technology, in one aspect, each "spot" on the array has a known sequence, e.g., a known segment of genome or other sequence. The invention can be practiced in conjunction with any method or protocol or device known in the art, which are well described in the scientific and patent literature.

General Techniques

The nucleic acids used to practice this invention, whether RNA, cDNA, genomic DNA, vectors, viruses or hybrids thereof, may be isolated from a variety of sources, genetically engineered, amplified, and/or expressed/generated recombinantly. Any recombinant expression system can be used, including, in addition to bacterial cells, e.g., mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with a primer sequence.

Techniques for the manipulation of nucleic acids, such as, e.g., subcloning, labeling probes (e.g., random-primer labeling using Klenow polymerase, nick translation, amplification), sequencing, hybridization, G-banding, CGH, SKY, FISH and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Cloning of Genomic Nucleic Acids

The compilations, or sets, libraries or collections, of nucleic acids or genomic nucleic acids used in the arrays and methods of the invention, e.g., those immobilized onto arrays or used as samples, can be obtained and manipulated by cloning into various vehicles. If necessary, genomic nucleic acid samples can be screened and re-cloned or amplified from any source of genomic DNA. Thus, in various aspects, forms of genomic nucleic acid used in the methods of the invention (including arrays and samples) include genomic DNA, e.g., genomic libraries, contained in mammalian and human artificial chromosomes, satellite artificial chromosomes, yeast artificial chromosomes, bacterial artificial chromosomes, PI artificial chromosomes, recombinant vectors and viruses, plasmids, and the like.

Mammalian artificial chromosomes (MACs) and human artificial chromosomes (HAC) are, e.g., described in Ascenzioni (1997) Cancer Lett. 118:135-142; Kuroiwa (2000) Nat. Biotechnol. 18:1086-1090; U.S. Pat. Nos. 5,288,625; 5,721,118; 6,025,155; 6,077,697). MACs can contain inserts larger than 400 kilobase (Kb), see, e.g., Mejia (2001) Am. J. Hum. Genet. 69:315-326. Auriche (2001) EMBO Rep. 2:102-107, has built a human minichromosomes having a size of 5.5 kilobase.

Satellite artificial chromosomes, or, satellite DNA-based artificial chromosomes (SATACs), are, e.g., described in Warburton (1997) Nature 386:553-555; Roush (1997) Science 276:38-39; Rosenfeld (1997) Nat. Genet. 15:333-335). SATACs can be made by induced de novo chromosome formation in cells of different mammalian species; see, e.g., Hadlaczky (2001) Curr. Opin. Mol. Ther. 3:125-132; Csonka (2000) J. Cell Sci. 113 (Pt 18):3207-3216.

Yeast artificial chromosomes (YACs) can also be used and typically contain inserts ranging in size from 80 to 700 kb. YACs have been used for many years for the stable propagation of genomic fragments of up to one million base pairs in size; see, e.g., U.S. Pat. Nos. 5,776,745; 5,981,175; Feingold (1990) Proc. Natl. Acad. Sci. USA 87:8637-8641; Tucker (1997) Gene 199:25-30; Adam (1997) Plant J. 11:1349-1358; Zeschnigk (1999) Nucleic Acids Res. 27:21.

Bacterial artificial chromosomes (BACs) are vectors that can contain 120 Kb or greater inserts, see, e.g., U.S. Pat. Nos. 5,874,259; 6,277,621; 6,183,957. BACs are based on the *E. coli* F factor plasmid system and simple to manipulate and purify in microgram quantities. Because BAC plasmids are kept at one to two copies per cell, the problems of rearrangement observed with YACs, which can also be employed in the present methods, are eliminated; see, e.g., Asakawa (1997) Gene 69-79; Cao (1999) Genome Res. 9:763-774.

P1 artificial chromosomes (PACs), bacteriophage P1-derived vectors are, e.g., described in Woon (1998) Genomics 50:306-316; Boren (1996) Genome Res. 6:1123-1130; Ioannou (1994) Nature Genet. 6:84-89; Reid (1997) Genomics 43:366-375; Nothwang (1997) Genomics 41:370-378; Kern (1997) Biotechniques 23:120-124). P1 is a bacteriophage that infects *E. coli* that can contain 75 to 100 Kb DNA inserts (see, e.g., Mejia (1997) Genome Res 7:179-186; Ioannou (1994) Nat Genet 6:84-89). PACs are screened in much the same way as lambda libraries. See also Ashworth (1995) Analytical Biochem. 224:564-571; Gingrich (1996) Genomics 32:65-74.

Other cloning vehicles can also be used, for example, recombinant viruses; cosmids, plasmids or cDNAs; see, e.g., U.S. Pat. No. 5,501,979; 5,288,641; 5,266,489.

These vectors can include marker genes, such as, e.g., luciferase and green fluorescent protein genes (see, e.g., Baker (1997) Nucleic Acids Res 25:1950-1956). Sequences, inserts, clones, vectors and the like can be isolated from natural sources, obtained from such sources as ATCC or GenBank libraries or commercial sources, or prepared by synthetic or recombinant methods.

Amplification of Nucleic Acids

Amplification using oligonucleotide primers can be used to generate or manipulate, e.g., subclone, nucleic acids of the compilations, or sets, libraries or collections, of nucleic acids or the nucleic acids used in the arrays and methods of the invention, to incorporate label into immobilized or sample nucleic acids, to detect or measure levels of nucleic acids hybridized to an array, and the like. Amplification, typically with degenerate primers, is also useful for incorporating detectable probes (e.g., Cy5™- or Cy3™-cytosine conjugates) into nucleic acids representative of test or control genomic DNA to be used to hybridize to immobilized genomic DNA. Amplification can be used to quantify the amount of nucleic acid is in a sample, see, e.g., U.S. Pat. No. 6,294,338. The skilled artisan can select and design suitable oligonucleotide amplification primers. Amplification methods are also well known in the art, and include, e.g., polymerase chain reaction, PCR(PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989)

Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques, e.g., nucleic acid sequence based amplification, or, "NASBA," see, e.g., Birch (2001) Lett. Appl. Microbiol. 33:296-301; Greijer (2001) J. Virol. Methods 96:133-147. See also Berger (1987) Methods Enzymol. 152:307-316; Sambrook; Ausubel; U.S. Pat. Nos. 4,683,195 and 4,683,202.

Hybridizing Nucleic Acids

In practicing the methods of the invention, samples of nucleic acid, e.g., isolated, cloned or amplified genomic nucleic acid, are hybridized to the compilations, or sets, libraries or collections, of nucleic acids or the immobilized nucleic acids. In alternative aspects, the hybridization and/or wash conditions are carried out under moderate to stringent conditions. The invention provides methods for selecting a genomic nucleic acid segment for use as a hybridization target in a hybridization reaction, e.g., a comparative genomic hybridization (CGH) reaction, for the detection of a chromosomal abnormality comprising, inter alia, selecting a chromosomal segment that hybridizes to a single locus under stringent conditions. Exemplary hybridization conditions, including stringent hybridization conditions, are set forth below.

An extensive guide to the hybridization of nucleic acids is found in, e.g., Sambrook Ausubel, Tijssen. Stringent hybridization and wash conditions can be selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

Exemplary stringent hybridization conditions for hybridization of complementary nucleic acids which have more than 100 complementary residues on an array can comprise 42° C. using standard hybridization solutions (see, e.g., Sambrook), with the hybridization being carried out overnight. Exemplary highly stringent wash conditions can also comprise 0.15 M NaCl at 72° C. for about 15 minutes. Exemplary stringent wash conditions can also comprise a 0.2×SSC wash at 65° C. for 15 minutes (see, e.g., Sambrook). In one aspect, a high stringency wash is preceded by a medium or low stringency wash to remove background probe signal. An exemplary medium stringency wash for a duplex of, e.g., more than 100 nucleotides, comprises 1×SSC at 45° C. for 15 minutes. An exemplary low stringency wash for a duplex of, e.g., more than 100 nucleotides, can comprise 4×to 6×SSC at 40° C. for 15 minutes.

In alternative aspects, in making the compilations, or sets, libraries or collections, of nucleic acids or arrays, and practicing the methods of the invention, the fluorescent dyes Cy3™ and Cy5™ can be used to differentially label nucleic acid fragments from two samples, e.g., nucleic acid generated from a control (e.g., "wild type"), versus a test cell or tissue sample, or, to label the compilations, or sets, libraries or collections, of nucleic acids or array-immobilized nucleic acid and/or sample nucleic acid. Many commercial instruments are designed to accommodate the detection of these two dyes. To increase the stability of Cy5™, or fluors or other oxidation-sensitive compounds, antioxidants and free radical scavengers can be used in hybridization mixes, the hybridization and/or the wash solutions. Thus, Cy5™ signals are dramatically increased and longer hybridization times are possible.

In alternative aspects, the methods of the invention are carried out in a controlled, unsaturated humidity environment, and, the compilations, or sets, libraries or collections, of nucleic acids or arrays of the invention can further comprise apparatus or devices capable of controlling humidity. Controlling humidity is one parameter that can be manipulated to increase hybridization sensitivity. Thus, in one aspect, in practicing the methods of the invention, hybridization can be carried out in a controlled, unsaturated humidity environment; hybridization efficiency is significantly improved if the humidity is not saturated. The hybridization efficiency can be improved if the humidity is dynamically controlled, i.e., if the humidity changes during hybridization. Array devices comprising housings and controls that allow the operator to control the humidity during pre-hybridization, hybridization, wash and/or detection stages can be used. The device can have detection, control and memory components to allow pre-programming of the humidity (and temperature and other parameters) during the entire procedural cycle, including pre-hybridization, hybridization, wash and detection steps.

In alternative aspects, the methods of the invention can incorporate hybridization conditions comprising temperature fluctuations and, the compilations, or sets, libraries or collections, of nucleic acids or arrays of the invention can further comprise apparatus or devices capable of controlling temperature, e.g., an oven. Hybridization has much better efficiency in a changing temperature environment as compared to conditions where the temperature is set precisely or at relatively constant level (e.g., plus or minus a couple of degrees, as with most commercial ovens). Reaction chamber temperatures can be fluctuatingly modified by, e.g., an oven, or other device capable of creating changing temperatures.

In alternative aspects, the methods of the invention can comprise hybridization conditions comprising osmotic fluctuations, and, the compilations, or sets, libraries or collections, of nucleic acids or arrays of the invention can further comprise apparatus or devices capable of controlling osmotic conditions, e.g., generate a e.g., a solute gradient. Hybridization efficiency (i.e., time to equilibrium) can also be enhanced by a hybridization environment that comprises changing hyper-/hypo-tonicity, e.g., a solute gradient. A solute gradient is created in a device. For example, a low salt hybridization solution is placed on one side of the array hybridization chamber and a higher salt buffer is placed on the other side to generate a solute gradient in the chamber.

Fragmentation and Digestion of Nucleic Acid

In practicing the methods of the invention, the compilations, or sets, libraries or collections, of nucleic acids, the immobilized and/or sample nucleic acids can be cloned, labeled or immobilized in a variety of lengths. For example, in one aspect, the genomic nucleic acid segments can have a length smaller than about 200 bases. Use of labeled genomic DNA limited to this small size significantly improves the resolution of the molecular profile analysis, e.g., in array-based CGH. For example, use of such small fragments allows for significant suppression of repetitive sequences and other unwanted, "background" cross-hybridization on the immobilized nucleic acid. Suppression of repetitive sequence hybridization greatly increases the reliability of the detection of copy number differences (e.g., amplifications or deletions) or detection of unique sequences.

The resultant fragment lengths can be modified by, e.g., treatment with DNase. Adjusting the ratio of DNase to DNA polymerase in a nick translation reaction changes the length of the digestion product. Standard nick translation kits typically generate 300 to 600 base pair fragments. If desired, the labeled nucleic acid can be further fragmented to segments below 200 bases, down to as low as about 25 to 30 bases, random enzymatic digestion of the DNA is carried out, using, e.g., a DNA endonucleases, e.g., DNase (see, e.g., Herrera (1994) J. Mol. Biol. 236:405-411; Suck (1994) J. Mol. Recognit. 7:65-70), or, the two-base restriction endonuclease CviJI (see, e.g., Fitzgerald (1992) Nucleic Acids Res. 20:3753-3762) and standard protocols, see, e.g., Sambrook, Ausubel, with or without other fragmentation procedures.

Other procedures can also be used to fragment genomic DNA, e.g. mechanical shearing, sonication (see, e.g., Deininger (1983) Anal. Biochem. 129:216-223), and the like (see, e.g., Sambrook, Ausubel, Tijssen). For example, one mechanical technique is based on point-sink hydrodynamics that result when a DNA sample is forced through a small hole by a syringe pump, see, e.g., Thorstenson (1998) Genome Res. 8:848-855. See also, Oefner (1996) Nucleic Acids Res. 24:3879-3886; Ordahl (1976) Nucleic Acids Res. 3:2985-2999. Fragment size can be evaluated by a variety of techniques, including, e.g., sizing electrophoresis, as by Siles (1997) J. Chromatogr. A. 771:319-329, that analyzed DNA fragmentation using a dynamic size-sieving polymer solution in a capillary electrophoresis. Fragment sizes can also be determined by, e.g., matrix-assisted laser desorption/ionization time-of-flight mass spectrometry, see, e.g., Chiu (2000) Nucleic Acids Res. 28:E31.

Syndromes Associated with a Contiguous Gene Abnormality

In one aspect, the invention provides compilations, or sets, libraries or collections, of nucleic acids and arrays and methods for the detection of a chromosomal abnormality or for the diagnosis or prognosis of a syndrome associated with a contiguous gene abnormality. Any set or combination of genomic nucleic acid segments associated with a chromosomal abnormality, a contiguous gene abnormality, a genetically linked disease or a syndrome, without limitation, can be used in making and using the compilations, or sets, libraries or collections, of nucleic acids or arrays and practicing the methods of the invention, including genomic nucleic acid segments not specifically exemplified herein. For example, the compilations, or sets, libraries or collections, of nucleic acids or arrays and methods of the invention can comprise genomic nucleic acid segments set forth in the literature, see, e.g., Charles R. Scriver, et al., (2000) "The Metabolic and Molecular Bases of Inherited Disease," 8$^{th}$ edition, New York, McGraw-Hill; Pat Gilbert (2000) "The A-Z Reference Book of Syndromes and Inherited Disorders: A Manual for Health, Social and Education Workers" 3 Ed edition, Stanley Thomes Pub Ltd.; Suzanne B. Cassidy, et al. (Ed), (2001) "Management of Genetic Syndromes," Wiley-Liss.

The compilations, or sets, libraries or collections, of nucleic acids or arrays and methods of the invention can be used for the differential diagnosis of genetically linked diseases or syndromes, formulating appropriate treatment plans and estimating a prognosis. The methods of the invention can be used in situations where the causality, diagnosis, or prognosis (e.g., severity, metastatic potential) of a pathology or condition is associated with one or more genetic defects, e.g., a syndrome caused by a contiguous chromosomal defect.

For example, determining the presence of a contiguous gene defect can be helpful in predicting diagnosing and the prognosis of cancer, classifying a cancer or formulating a treatment plan or prognosis. For example, metastasis suppressor genes on human chromosomes for cutaneous melanoma, as well as a variety of other forms of human cancer, have been located on, e.g., 7q21-22, 7q31.2-32, 8p21-12, 10q11-22, 11p13-11.2, 12p11-q13, 12q24-ter, and 17pter-q23 (see, e.g., Goldberg (2000) Am. J. Hum. Genet. 67(2): 417-431; Ichikawa (2000) Asian J. Androl. 2(3):167-171). Accordingly, the methods and arrays of the invention can be used for predicting, diagnosing and the prognosis of cancers.

1p Deletion Syndrome

In one aspect, the compilations, or sets, libraries or collections, of nucleic acids or arrays of the invention comprise a segment of genomic nucleic acid comprising chromosome 1, locus 1p;36, and the syndrome detected is 1p Deletion Syndrome. Patients with deletion of band 1p36.33, have had clinical findings of obesity and hyperphagia; and the overlap of manifestations with Prader-Willi syndrome. See, e.g., Eugster (1997) Am. J. Med. Genet. 70(4):409-412. Patients with karyotypic abnormalities resulting in monosomy for a portion of 1p36.3 can have microcephaly, mental retardation, prominent forehead, deep-set eyes, depressed nasal bridge, flat midface, relative prognathism, and abnormal ears. See, e.g., Reish (1995) Am. J. Med. Genet. 59(4):467-475.

3p Deletion Syndrome

In one aspect, the compilations, or sets, libraries or collections, of nucleic acids or arrays of the invention comprise a segment of genomic nucleic acid comprising chromosome 3, locus 3p25-pter, and the syndrome detected is p3p Deletion Syndrome.

Chromosome 3p deletions are thought to be involved in the pathogenesis of sporadic endocrine pancreatic tumors (EPTs); also, von Hippel-Lindau's disease (VHL gene at 3p25.5) has been associated with EPTs. Chromosome 3p deletion is frequently involved in solid human tumors. See, e.g., Barghom (2001) J. Pathol. 194(4):451-458. Allele loss in some regions of chromosome 3p has been detected in primary breast tumors. See, e.g., Maitra (2001) Am. J. Pathol. 159(1):119-130.

3p Duplication Syndrome and "C Syndrome"

In one aspect, the compilations, or sets, libraries or collections, of nucleic acids or arrays of the invention comprise a segment of genomic nucleic acid comprising chromosome 3, locus 3p21-pter, and the syndrome detected is 3p Duplication Syndrome. A partial trisomy of chromosome 3P, an inverted duplication 3p22—>3pter (dup(3) (pter—>p26::p22(p26::p26—>ter)), was found to be associated with psychomotor retardation and slight dysmorphism. A partial 3p trisomy, a 3p/17p translocation: t(3;7)(p253;p133), was found to be associated with mental retardation and poor speech development. See, e.g., Smeets (2001) Genet. Couns. 12(1):85-89. "C syndrome," a multiple congenital anomaly/mental retardation (MCA/MR) syndrome, was found to be associated with a duplication of 3p. See, e.g., McGaughran (2000) Am. J. Med. Genet. 94(4):311-315.

Wolf-Hirschhorn Syndrome and Pitt-Rogers-Danks Syndrome

In one aspect, the compilations, or sets, libraries or collections, of nucleic acids or arrays of the invention comprise a segment of genomic nucleic acid comprising chromosome 4, locus 4p16.3, and the syndrome detected is Wolf-Hirschhorn Syndrome. Wolf-Hirschhorn syndrome (WHS) is a well-known congenital malformation syndrome caused by deletion of the short arm of chromosome 4 (4p-). Most cases occur de novo and are of paternal origin. WHS children have severe developmental disabilities. The phenotype of adult WHS is in general similar to that of childhood WHS. Growth retardation, microcephaly and mental retardation are the rule in both adults and children. Facial dysmorphism also remains similar. The main difference lies in the absence of serious internal (cardiac) abnormalities in adult WHS. See, e.g., Battaglia (2001) Adv. Pediatr. 48:75-113; Marcelis (2001) Genet. Couns. 12:35-48. See, e.g., Kant (1997) J. Med. Genet. 34(7):569-572. Pitt-Rogers-Danks syndrome has also been associated with deletions on chromosome 4p16.

4p Duplication Syndrome

In one aspect, the compilations, or sets, libraries or collections, of nucleic acids or arrays of the invention comprise a segment of genomic nucleic acid comprising chromosome 4, locus 4p15.2-16.1, and the syndrome detected is 4p Duplication Syndrome. Duplications of the distal half of 4p give rise to the partial trisomy 4 syndrome, characterized by a "boxer" nose configuration and deep-set eyes. These signs are usually observed even in cases of small terminal duplications. A "tandem" duplication of 4p16.1p16.3 has been detected in association with a subtle deletion of 4p16.3pter on the same chromosome in a patient with the WHS phenotype. See, e.g., Zollino (1999) Am. J. Med. Genet. 82(5):371-375.

Cri du Chat Syndrome

In one aspect, the compilations, or sets, libraries or collections, of nucleic acids or arrays of the invention comprise a segment of genomic nucleic acid comprising chromosome 5, locus 5p15.2-pter, and the syndrome detected is Cri du Chat Syndrome. Most patients with cri-du-chat syndrome have a de novo deletion of the short arm of chromosome 5 (5p). Patients show phenotypic and cytogenetic variability. Examples of deletions include: terminal –46,XX,del(5) (pter - - - p15.2:); interstitial –46,XX, del(5) (pter - - - p15.2::p13.3 - - - qter); 46,XX,der(5)t(5;11) (p15;q25)mat. Clinically, younger patients can have a typical high-pitched cry, psychomotor retardation, microcephaly, growth rate failure, and craniofacial abnormalities including round face, hypertelorism, broad nasal bridge, downward slanting palpebral fissures, and micrognathia. See, e.g., Mainardi (2001) J. Med. Genet. 38(3):151-158; Van Buggenhout (2000) Am. J. Med. Genet. 90(3):203-215.

Miller-Dieker Syndrome

In one aspect, the compilations, or sets, libraries or collections, of nucleic acids or arrays of the invention comprise a segment of genomic nucleic acid comprising chromosome 7, locus 7p13.3, and the syndrome detected is Miller-Dieker Syndrome. Trisomy 5p and Miller-Dieker syndromes frequently are the result of unbalanced segregations of reciprocal translocations of chromosomes 5 and 17 with other autosomes. Miller-Dieker Syndrome has been associated with a breakpoint in chromosome 17p13. Miller-Dieker syndrome patients can present with mental retardation, postnatal growth deficiency, generalized muscular hypotonia, seizures, microcephaly, cortical atrophy, partial agenesis of corpus callosum, cerebral ventriculomegaly, facial anomalies. See, e.g., Mutchinick (1999) Am. J. Med. Genet. 85(2):99-104; Pollin (1999) Am. J. Med. Genet. 85(4):369-375.

Williams Syndrome

In one aspect, the compilations, or sets, libraries or collections, of nucleic acids or arrays of the invention comprise a segment of genomic nucleic acid comprising chromosome 7, locus 7q11.23, and the syndrome detected is William's Syndrome. Williams syndrome is typically due to a contiguous gene deletion at 7q11.23, and has been associated with a distinctive facial appearance, cardiac abnormalities, infantile hypercalcemia, and growth and developmental retardation, including mild to severe mental retardation. For example, Williams syndrome was seen in a karyotype having microdeletions at 7q11.23 and 7q36 and additional chromosomal material at 7q36. See, e.g., Donnai (2000) Am. J. Med. Genet. 97(2):164-171; Wouters (2001) Am. J. Med. Genet. 102(3):261-265.

Langer-Giedion Syndrome (LGS) or TRPS II

In one aspect, the compilations, or sets, libraries or collections, of nucleic acids or arrays of the invention comprise a segment of genomic nucleic acid comprising chromosome 8, locus 8q24.1, and the syndrome detected is Langer-Giedion Syndrome (LGS) or tricho-rhino-phalangeal syndrome type II (TRPS II). It comprises the clinical features of two autosomal dominant diseases, TRPS I, and a form of multiple cartilaginous exostoses caused by mutations in the EXT1 gene. In contrast to TRPS I patients, most TRPS II patients have cytogenetically visible deletions and are often mentally retarded. See, e.g., Hilton (2001) Genomics 71(2):192-199; Nardmann (1997) Hum. Genet. 99(5): 638-643. Other syndromes with contiguous deletions of chromosome 8q include Cohen syndrome (8q22-q23), Klip-Feil syndrome (8q22.2), hereditary spastic paraplegia (8q24), and benign adult familial myoclonic epilepsy (8q23.3-q24.1).

Trichorhinophalangeal Syndrome (TRPS) or TRPS I

In one aspect, the compilations, or sets, libraries or collections, of nucleic acids or arrays of the invention comprise a segment of genomic nucleic acid comprising chromosome 8, locus 8q24.1, and the syndrome detected is Trichorhinophalangeal Syndrome (TRPS) or TRPS I. TRPS I individuals typically have dysmorphic features and severe short stature. TRPS comprises a distinctive combination of hair, facial and bony abnormalities with variable expression. The absence of generalized shortness of all phalanges, metacarpals and metatarsals distinguish it from TRPS III, and absence of exostosis and mental retardation rule out TRPS II. See, e.g., George (1998) J. Eur. Acad. Dermatol. Venereol. 11(1):66-68; Naselli (1998) Pediatr. Radiol. 28(11):851-855.

9p Deletion Syndrome

In one aspect, the compilations, or sets, libraries or collections, of nucleic acids or arrays of the invention comprise a segment of genomic nucleic acid comprising chromosome 9, locus 9p, e.g., locus 9p22-pter, and the syndrome detected is 9p Deletion Syndrome. This syndrome has been associated with de novo deletions in the short arm of chromosome 9. Patients can have developmental delay/ mental retardation, seizures and learning disabilities. Mental retardation can be of variable degrees and there can be a marked deficit in visuo-praxic and visuo-spatial skills associated with memory disturbance. See, e g., Chilosi (2001)

Am. J. Med. Genet. 100(2):138-144. In contrast, cases of tetrasomy 9p are extremely rare; the principal clinical manifestations of this condition are characteristic craniofacial abnormalities, generalized hypotonia and severe mental retardation, see, e g., Kobayashi (2000) J. Craniomaxillofac. Surg. 28(3):165-170.

DiGeorge Syndrome II

In one aspect, the compilations, or sets, libraries or collections, of nucleic acids or arrays of the invention comprise a segment of genomic nucleic acid comprising chromosome 10, locus 10p13-p14, and the syndrome detected is DiGeorge Syndrome II. This syndrome is characterized by neural-crest-related developmental defects. Partial monosomy 10p is a rare chromosomal condition and a significant proportion of patients show features of DiGeorge syndrome (DGS) and velocardiofacial syndrome (VCFS). One patient with DiGeorge syndrome (DGS) phenotype had an unbalanced translocation [45,XY,−10,−22,+der(10),t(10; 22)(p13;q11)] resulting in monosomy of 10p3-pter and 22q11-pter. See, e.g., Dasouki (1997) Am. J. Med. Genet. 73(1):72-75; Lichtner (2000) J. Med. Genet. 37(1):33-37; Epstein (2001) Trends Genet. 17(10):S13-17.

WAGR Syndrome II

In one aspect, the compilations, or sets, libraries or collections, of nucleic acids or arrays of the invention comprise a segment of genomic nucleic acid comprising chromosome 11, locus 11p13, and the syndrome detected is WAGR Syndrome. The Wilms' tumor-aniridia-genital anomalies-mental retardation (WAGR) syndrome is associated with an increased risk for developing Wilms' tumor. WAGR (Wilms' tumor, aniridia, genital anomalies, and mental retardation) syndrome anomalies have been associated with balanced reciprocal 7;11 translocation and an 11p13 breakpoint. See, e.g., Crolla (1997) J. Med. Genet. 34(3):207-212; Ariel (1996) Pediatr. Pathol. Lab. Med. 16(6):1013-1021.

Beckwith-Wiedemann Syndrome (BWS)

In one aspect, the compilations, or sets, libraries or collections, of nucleic acids or arrays of the invention comprise a segment of genomic nucleic acid comprising chromosome 11, locus 11p15.5, and the syndrome detected is Beckwith-Wiedemann Syndrome. Beckwith-Wiedemann syndrome (BWS) is an imprinting disorder characterized by somatic overgrowth, congenital malformations, and predisposition to childhood tumors. Chromosome 11p15.5 have been reported to have an imprinted gene cluster of 1 Mb, which has been implicated in a wide variety of malignancies and BWS. See, e.g., Li (2001) Genomics 74(3):370-376; Horike (2000) Hum. Mol. Genet. 9(14):2075-2083.

Potocki-Shaffer Syndrome (Multiple Exostoses II Locus)

In one aspect, the compilations, or sets, libraries or collections, of nucleic acids or arrays of the invention comprise a segment of genomic nucleic acid comprising chromosome 11, locus 11p11.2, and the syndrome detected is Potocki-Shaffer Syndrome (Multiple Exostoses II Locus). Potocki-Shaffer Syndrome is caused by a proximal deletion in the short arm of chromosome 11. Patients having the syndrome can have oval defects of the parietal bones (parietal foramina). See, e.g., Wu (2000) Am. J. Hum. Genet. 67(5):1327-1332.

Angelman Syndrome (AS)

In one aspect, the compilations, or sets, libraries or collections, of nucleic acids or arrays of the invention comprise a segment of genomic nucleic acid comprising chromosome 15, locus 15q12 or 15q13, and the syndrome detected is Angelman Syndrome. It has been reported to be caused by the haploinsufficiency of the 15q11-q13 region, and, de novo deletions of chromosome 15q11-q13. It has also been reported that Angelman syndrome can be caused by genetic abnormalities affecting the maternal copy of chromosome region 15q12. It has been observed that extra copies of this same genomic region, in the form of inv-dup (15) or intra-chromosomal duplications, of maternal origin, are usually associated with a severe neurological phenotype characterized by developmental delay and untreatable seizures. See, e.g., Torrisi (2001) Am. J. Med. Genet. 106(2): 125-128; Baumer (1999) Hum. Genet. 105(6):598-602; Greger (1997) Am. J. Hum. Genet. 60(3):574-580.

Prader-Willi Syndrome (PWS)

In one aspect, the compilations, or sets, libraries or collections, of nucleic acids or arrays of the invention comprise a segment of genomic nucleic acid comprising chromosome 15, locus 15q12, and the syndrome detected is Prader-Willi Syndrome (PWS). PWS is a neuroendocrine disorder reported to be due to: a large paternally derived chromosome deletion of 15q11q13, to maternal uniparental disomy (UPD), or imprinting mutation (IC). Severe learning disabilities (e.g., attention-deficit hyperactivity disorder), dyslexia, and excessive daytime sleepiness are common symptoms in PWS. See, e.g., Manni (2001) Clin. Neurophysiol. 112(5):800-805; Fernandez-Novoa (2001) Rev. Neurol. 32(10):935-938.

Rubinstein-Taybi Syndrome (RTS)

In one aspect, the compilations, or sets, libraries or collections, of nucleic acids or arrays of the invention comprise a segment of genomic nucleic acid comprising chromosome 16, locus distal 16p13.3, and the syndrome detected is Rubinstein-Taybi Syndrome (RTS). RTS is a malformation syndrome characterized by facial abnormalities, broad thumbs, broad big toes, and mental retardation. In a subset of RTS patients, microdeletions, translocations, and inversions involving chromosome band 16p13.3 can be detected. Immunodeficiency can be a prominent feature of this syndrome and may predispose these patients to recurrent infections. See, e.g., Petrij (2000) J. Med. Genet. 37(3):168-176; Villella (2000) Arch. Dis. Child. 83(4):360-361.

Charcot-Marie-Tooth Disease Type 1A(CMT-1A)

In one aspect, the compilations, or sets, libraries or collections, of nucleic acids or arrays of the invention comprise a segment of genomic nucleic acid comprising chromosome 17, locus 17p12, and the syndrome detected is Charcot-Marie-Tooth Disease Type 1A(CMT-1A). Charcot-Marie-Tooth neuropathy type 1 (CMT1) is a genetically heterogeneous group of chronic demyelinating polyneuropathies with loci mapping to chromosome 17 (CMT1A), chromosome 1 (CMT1B) and to another unknown autosome (CMT1C). CMT1A accounts for 70-90% of cases of Charcot-Marie-Tooth Disease Type 1 and is most frequently caused by the tandem duplication of a 1.4-Mb genomic fragment on chromosome 17p12. Locus 17p12 is also associated with the peripheral neuropathies, such as hereditary neuropathy with liability to pressure palsies (HNPP) (see below). Some analyses have suggested that the syndrome is associated with de novo 17p11.2 duplication, paternal in origin, arising from unequal crossing over due to homologous recombination between flanking repeat gene clusters. X-linked dominant Charcot-Marie-Tooth (CMTX) disease is a motor and sensory neuropathy caused by mutations in the connexin 32 (CX32) gene. See, e.g., Badano (2001) Clin. Chem. 47(5):838-843; Potocki (2000) Nat. Genet. 24(1):84-87.

Hereditary Neuropathy (HNPP)

In one aspect, the compilations, or sets, libraries or collections, of nucleic acids or arrays of the invention comprise a segment of genomic nucleic acid comprising chromosome 17, locus 17p12, and the syndrome detected is Hereditary Neuropathy with Liability to Pressure Palsies (HNPP). HNPP is an autosomal dominant disorder that results in a recurrent, episodic demyclinating neuropathy. It also can be characterized by reversible episodes of sensorimotor deficits after neural compression injuries. Also known as tomaculous neuropathy, HNPP is further characterized ultrastructurally by multiple focal thickenings (tomacula) of peripheral myelin and has an autosomal dominant inheritance. HNPP is associated with a 1.5-Mb deletion in chromosome 17p11.2-12 and results from reduced expression of the PMP22 gene. See, e.g., Mersiyanova (2000) Hum. Mutat.15(4):340-347; Chance (2001) Phys. Med. Rehabil. Clin. N. Am. 12(2):277-291; Lane (2001) J. Hand Surg. [Am] 26(4):670-674.

Miller-Dieker Syndrome/Isolated Lissencephaly

In one aspect, the compilations, or sets, libraries or collections, of nucleic acids or arrays of the invention comprise a segment of genomic nucleic acid comprising chromosome 17, locus 17p13.3, and the syndrome detected is Miller-Dicker Syndrome/Isolated Lissencephaly. The Miller-Dieker syndrome (type I lissencephaly) is a neuronal migration disorder that is associated with microdeletions in the short arm of chromosome 17, at locus 17p13.3. For example, one patient was found to have a de novo balanced translocation with breakpoint at 8p11.23 and 17p13.3. In contrast, neurofibromatosis type I (NF1) is an autosomal dominant condition associated with mutations in the long arm of chromosome 17, and characterized by neurofibromas, cafe-au-lait spots and axillary freckling. See, e.g., King (2000) Acta Neuropathol. (Berl) 99(4):425-427; Honda (1998) Brain Dev. 20(3):190-192.

Smith-Magenis Syndrome (SMS)

In one aspect, the compilations, or sets, libraries or collections, of nucleic acids or arrays of the invention comprise a segment of genomic nucleic acid comprising chromosome 17, locus 17p11.2, and the syndrome detected is Smith-Magenis Syndrome (SMS). SMS is a clinically recognizable syndrome comprising multiple congenital anomalies and mental retardation. Its symptoms can include facial anomalies, brachydactyly, severe mental retardation, and self-injuring behavior. SMS is associated with a microdeletion (an interstitial deletion) of the short arm of chromosome 17, locus 17p11.2. Interestingly, a patient with a del(17)(p11.2p12) karyotype displayed symptoms of both SMS and Joubert syndrome (JS), the later characterized by cerebellar vermis hypoplasia, hypotonia, ataxic gait, developmental delay, and abnormal respiratory pattern. A prenatal case of SMS found dysmorphic facial features, tetralogy of Fallot, a thymic duct remnant, pancreatic islet cell hyperplasia, and abnormal lung fissuring. See, e.g., Juyal (1996) Am. J. Hum. Genet. 58(5):998-1007; Natacci (2000) Am. J. Med. Genet. 95(5):467-472; Thomas (2000) Fetal Diagn. Ther. 15(6):335-337.

Alagille Syndrome (AGS)

In one aspect, the compilations, or sets, libraries or collections, of nucleic acids or arrays of the invention comprise a segment of genomic nucleic acid comprising chromosome 20, locus 20p11.2-p12, and the syndrome detected is Alagille Syndrome (AGS), also known as arteriohepatic dysplasia. Patients can have a deletion in chromosome 20p, with 20p11.23-p12.2 as the area of minimal overlap. One AGS case had aparacentric inversion (PAI) of chromosome 20p12.2p13. Locus 20p11.2-p12 encodes a ligand for the Notch1 transmembrane receptor, which plays a key role in cell-to-cell signaling during differentiation. See, e.g., Yuan (1997) Acta Paediatr. Jpn 39(6):647-652; Hol (1995) Hum. Genet. 95(6):687-690.

Digeorge/Velocardiofacial Syndrome (VCFS)

In one aspect, the compilations, or sets, libraries or collections, of nucleic acids or arrays of the invention comprise a segment of genomic nucleic acid comprising chromosome 22, locus 22q11.2, and the syndrome detected is Digeorge/Velocardiofacial Syndrome (VCFS). VCFS can result from a microdeletion on chromosome 22, locus 22q11.2. VCFS is associated with a broad clinical spectrum characterized by multiple congenital malformations, including cleft palate and cardiac anomalies, that frequently overlaps the DiGeorge syndrome. Estimates suggest that the 22q11.2 deletion occurs in approximately 1 in 4000 live births. Clinical studies indicate that more than 30% of children with VCFS will develop schizophrenia. Velofacial hypoplasia (Sedlackova syndrome) and velocardiofacial (Shprintzen) syndrome are also both associated with del 22q11.2. See, e.g., Eliez (2001) Am. J. Psychiatry 158(3): 447-453; Fokstuen (2001) Eur. J. Pediatr. 160(1):54-57; Duke (2000) Arch. Otolaryngol. Head Neck Surg. 126(9): 1141-1145.

Adrenal Hypoplasia Congenita (AHC)

In one aspect, the compilations, or sets, libraries or collections, of nucleic acids or arrays of the invention comprise a segment of genomic nucleic acid comprising chromosome X, locus Xp21, and the syndrome detected is Adrenal Hypoplasia Congenita (AHC). AHC patients have a deletion on the short arm of the X chromosome, locus p21.1 to p22.1. AHC is a developmental disorder of the human adrenal cortex and has been proposed to be caused by deletion or mutation of the DAX-1 gene within locus p21.1 to p22.1; DAX-1 is a member of the nuclear hormone receptor superfamily. The Xp21 syndrome should be considered in any infant with adrenal insufficiency. Measurement of serum triglycerides and creatine kinase activity and karyotype screening tests will facilitate early diagnosis. See, e.g., Peter (1998) J. Clin. Endocrinol. Metab. 83(8):2666-2674; Cole (1994) Clin. Chem. 40(11 Pt 1):2099-2103, and the Glycerol kinase deficiency (GKD) discussion, below.

Duchenne/Becker Muscular Dystrophy

In one aspect, the compilations, or sets, libraries or collections, of nucleic acids or arrays of the invention comprise a segment of genomic nucleic acid comprising chromosome X, locus Xp21, and the syndrome detected is Duchenne/Becker Muscular Dystrophy. Cardiac abnormalities, cardiomyopathy and skeletal muscle weakness have been described in female carriers of the Xp21 (Duchenne and Becker) muscular dystrophies. Duchenne and Becker dystrophies have been associated with the absence or altered expression of dystrophin in cardiac and skeletal muscles. They are frequently complicated by cardiac hypertrophy and dilated cardiomyopathy. See, e.g., Grain (2001) Neuromuscul. Disord. 11(2):186-191; Crilley (2000) J. Am. Coll. Cardiol. 36(6):1953-1958, and the Glycerol kinase deficiency (GKD) discussion, below.

Glycerol Kinase Deficiency (GKD)

In one aspect, the compilations, or sets, libraries or collections, of nucleic acids or arrays of the invention comprise a segment of genomic nucleic acid comprising chromosome X, locus Xp21, and the syndrome detected is Glycerol Kinase Deficiency (GKD). Glycerol kinase deficiency (GKD) is an X-linked recessive disorder having a deletion on the short arm of the X chromosome, locus p21.1 to p22.1. There are two types. an isolated form and a complex form. The clinical and biochemical phenotype of isolated GKD may vary from a life-threatening childhood metabolic crisis to asymptomatic adult 'pseudohypertriglyceridaemia', resulting from hyperglycerolaemia. The complex GKD is an Xp2l contiguous gene syndrome involving the glycerol kinase locus together with the adrenal hypoplasia congenita (AHC) or Duchenne muscular dystrophy (DMD) loci or both. Complex GKD patients can have an "hourglass" appearance of the middle of the face; hypertelorism; rounded palpebral fissures; esotropia; wide, flattened earlobes; and a downturned mouth. See, e.g., Sjarif (2000) J. Inherit. Metab. Dis. 23(6):529-547; Scheuerle (1995) J. Pediatr. 126(5 Pt 1):764-767.

Pelizaeus-Merzbacher Disease (PMD)

In one aspect, the compilations, or sets, libraries or collections, of nucleic acids or arrays of the invention comprise a segment of genomic nucleic acid comprising chromosome X, locus Xp22, and the syndrome detected is Pelizaeus-Merzbacher Disease (PMD). PMD is an X-linked recessive dysmyelinating disorder of the central nervous system. Most patients have point mutations in exons of the proteolipid protein (PLP1) gene or duplication of a genomic region that includes the PLP1 gene, on locus Xp22, on the short arm of the X chromosome. See, e.g., Hobson (2001) Hum. Mutat. 17(2):152; Hodes (2000) Am. J. Hum. Genet. 67(1):14-22; Inoue (1999) Ann. Neurol. 45(5):624-632.

Steroid Sulfatase Deficiency

In one aspect, the compilations, or sets, libraries or collections, of nucleic acids or arrays of the invention comprise a segment of genomic nucleic acid comprising chromosome X, locus Xp22.3, and the syndrome detected comprises steroid sulfatase deficiency. X chromosome deletions in the Xp22.3 region can result in steroid sulfatase deficiency and X-linked ichthyosis. In one patient, an interstitial deletion in Xp22.3 involved the Kallmann (KAL) gene, the steroid sulfatase (STS) gene and a putative mental retardation locus (MRX). X-linked ichthyosis (XLI) is an inborn error of metabolism due to steroid sulfatase (STS) deficiency. X-linked ichthyosis is a disorder of keratinization characterized by a generalized desquamation of large, adherent, dark brown scales. Extracutaneous manifestations include corneal opacity and cryptorchidism. See, e.g., Weissortel (1998) Clin. Genet. 54(1):45-51; Santolaya-Forgas (1997) Fetal Diagn. Ther. 12(1):36-39; Valdes-Flores (2001) Am. J. Med. Genet. 102(2): 146-148.

Abnormalities of the SRY Locus

In one aspect, the compilations, or sets, libraries or collections, of nucleic acids or arrays of the invention comprise a segment of genomic nucleic acid comprising chromosome Y, locus SRY locus/Yp, and the syndrome detected comprises abnormalities of the SRY (sex-determining region on the Y chromosome) locus. SRY has been identified at band Yp11.31p11.32 in normal XY males and in woman with XY gonadal dysgenesis. SRY signals have also been identified on Xp22 in one XX male. Ullrich-Turner syndrome (UTS) has been associated with Y fragments and gonadoblastomas. Thus, some clinicians have suggested that UTS patients should be examined for Y chromosome material, and that positive cases should have their dysgenic gonads excised due to the high risk of malignancy. See, e.g., Kadandale (2000) Am. J. Med. Genet. 95(1):71-74; Damiani (1999) J. Pediatr. Endocrinol. Metab. 12(6):827-831; Kadandale (2000) Microb. Comp. Genomics 5(2):71-74.

Sex Reversal (DSS)

In one aspect, the compilations, or sets, libraries or collections, of nucleic acids or arrays of the invention comprise a segment of genomic nucleic acid comprising chromosome X, locus Xp21, and the syndrome detected is Sex Reversal (DSS). The Xp21 locus contains the gene Ahch, also known as Dax1. Ahch encodes a transcription factor that has been implicated in sex determination and gonadal differentiation. Mutations in human AHC cause X-linked, adrenal hypoplasia congenita (AHC) and hypogonadotropic hypogonadism (HH). Studies have found Xp duplications in patients with sex reversal, with female or ambiguous genitalia occurring in spite of an intact Yp or SRY gene. Five different exchanges have been described two or more times: t(X;Y)(p21;q11), t(X;Y)(p22;p11), t(X;Y)(p22;q11-12), t(X;Y) (q22;q12), and t(X;Y)(q28;q12). See, e.g., Yu (1998) Nat. Genet. 20(4):353-7; Vasquez (1999) Genet. Couns. 10(3):301-334.

Kallman's Disease or Kallmann's Syndrome (KS)

In one aspect, the compilations, or sets, libraries or collections, of nucleic acids or arrays of the invention comprise a segment of genomic nucleic acid comprising chromosome X, locus Xp22.3, and the syndrome detected is Kaliman's Disease or Kallmann's syndrome (KS). KS is characterized by hypogonadotrophic hypogonadism in association with anosmia or hyposmia. KS can be associated with X-linked ichthyosis (XLI) in a contiguous gene syndrome comprising a genetic defect in the Xp22.3 region. KS has also been associated with olfactory neuroblastoma. See, e.g., Maya-Nunez (1999) Clin. Endocrinol. (Oxf) 50(2):157-162; Zappia (1992) J. Otolaryngol. 21(1):16-19.

17p11.2 Duplication Syndrome and Birt-Hogg-Dube Syndrome (BHD)

In one aspect, the compilations, or sets, libraries or collections, of nucleic acids or arrays of the invention comprise a segment of genomic nucleic acid comprising chromosome 17, locus 17p11.2, and the syndrome detected is 17p11.2 Duplication Syndrome. Duplication of locus 17p11.2 may be associated with Birt-Hogg-Dube syndrome (BHD), an autosomal dominant neoplasia syndrome characterized mainly by benign skin tumors (e.g., benign tumors of the hair follicle), and to a lesser extent, renal tumors, lung cysts, and spontaneous pneumothorax. The gene for BHD may associated with renal neoplasia and for lung and hair-follicle developmental defects. See, e.g., Schmidt (2001) Am. J. Hum. Genet. 69(4):876-82; Khoo (2001) Oncogene 20(37):5239-5242.

Smith-Magenis Syndrome (SMS)

In one aspect, the compilations, or sets, libraries or collections, of nucleic acids or arrays of the invention comprise a segment of genomic nucleic acid comprising chromosome 17, locus 17p11.2, and the syndrome detected is Smith-Magenis syndrome (SMS). SMS is a clinically recognizable contiguous gene syndrome ascribed to interstitial deletions of chromosome 17p11.2. SMS patients have clinically recognizable multiple congenital anomalies and mental retardation, including self-injury, tantrums, and sleep disturbance. SMS patients have a phase shift of their circadian rhythm of melatonin with a paradoxical diurnal secretion of the hormone. See, e.g., De Leersnyder (2001) J. Med. Genet. 38(9):586-590; De Leersnyder (2001) J. Pediatr. 139(1):111-116; Smith (1998) Am. J. Med. Genet. 81(2): 186-191.

Idiopathic Epilepsy and Paroxysmal Dyskinesia

In one aspect, the compilations, or sets, libraries or collections, of nucleic acids or arrays of the invention comprise a segment of genomic nucleic acid comprising chromosome 16, pericentromeric region, and the syndrome detected is idiopathic epilepsy and paroxysmal dyskinesia. This is a homogeneous syndrome of autosomal dominant infantile convulsions and paroxysmal (dystonic) choreoathetosis (ICCA). Use of the arrays and methods of the invention may be particularly useful because motor manifestations of epilepsy and of paroxysmal dyskinesia may be difficult to differentiate clinically. See, e.g., Guerrini (2001) Epilepsia 42 Suppl 3:36-41.

Hirschsprung Disease Type 2 and Waardenburg Syndrome

In one aspect, the compilations, or sets, libraries or collections, of nucleic acids or arrays of the invention comprise a segment of genomic nucleic acid comprising chromosome 13, locus 13q22, and the syndrome detected is Hirschsprung disease, including Hirschsprung disease type 2, and Waardenburg syndrome. Hirschsprung disease is a developmental disorder resulting from the arrest of the craniocaudal migration of enteric neurons from the neural crest along gastrointestinal segments of variable length. Waardenburg-Shah syndrome is an auditory pigmentary disorder. Hirschsprung disease, malrotation, isochromia, a profound sensorineural hearing loss, and several other anomalies were found in an infant with an interstitial deletion of 13q, see, e.g., Shanske (2001) Am. J. Med. Genet. 102(3):231-236.

Branchio-oto-renal (BOR) Syndrome

In one aspect, the compilations, or sets, libraries or collections, of nucleic acids or arrays of the invention comprise a segment of genomic nucleic acid comprising 8, locus 8q13.3, and the syndrome detected is branchio-oto-renal (BOR) syndrome. Branchio-oto-renal (BOR) syndrome is an autosomal dominant disorder involving hearing loss, branchial defects, ear pits and renal abnormalities. The arrays and methods of the invention can be used to distinguish it from oto-facio-cervical (OFC) syndrome, which is clinically similar to BOR syndrome, with clinical features in addition to those of BOR syndrome. See, e.g., Rickard (2001) Hum. Genet. 108(5):398-403.

Smith-Magenis Syndrome (SMS)

In one aspect, the compilations, or sets, libraries or collections, of nucleic acids or arrays of the invention comprise a segment of genomic nucleic acid comprising chromosome 1, locus 7p11.2, and the syndrome detected is Smith-Magenis syndrome (SMS). Smith-Magenis syndrome (SMS) is a multiple congenital anomaly/mental retardation (MCA/MR) syndrome link to a contiguous-gene deletion syndrome, involving chromosome 17p11.2, whose incidence is estimated to be 1:25,000 live births. SMS is characterized by a specific physical, behavioral and developmental pattern. The main clinical features consist of a broad flat midface with brachycefaly, broad nasal bridge, brachydactily, speech delay, hoarse deep voice and peripheral neuropathy. See, e.g., Di Cicco (2001 Int. J. Pediatr. Otorhinolaryngol. 59(2):147-150.

Leri-Weill Syndrome

In one aspect, the compilations, or sets, libraries or collections, of nucleic acids or arrays of the invention comprise a segment of genomic nucleic acid comprising chromosome X, locus Xp22.3, and the syndrome detected is Leri-Weill syndrome. Leri-Weill syndrome is characterized by short stature (SHOX), chondrodysplasia punctata (ARSE), bilateral Madelung deformity and mental retardation. See, e.g., Spranger (1999) Am. J. Med. Genet. 83(5): 367-371.

Chromosome abnormalities are common causes of congenital malformations and spontaneous abortions. They include structural abnormalities, polyploidy, trisomy, and mosaicism. Very few autosomal trisomies survive to birth, the three most common being those for chromosome 13, 18 and 21 giving rise to the syndromes named Patau, Edward's and Down's respectively (see, e.g., Moore (2000) Eur. J. Hum. Genet. 8:223-228). Thus, in alternative aspects, the arrays methods of the invention are used to diagnose Patau Syndrome, Edward's Syndrome and Down's Syndrome. See, e.g., Djalali (2000) Prenat. Diagn. 20:934-935. Table 1 sets forth in summary form exemplary contiguous gene syndromes that can be diagnosed by the compilations, or sets, libraries or collections, of nucleic acids, arrays and methods of the invention:

TABLE 1

Chromosome Loci Profiles of Contiguous Gene Syndromes

| Chromosome number | Locus | Syndrome |
| --- | --- | --- |
| 1 | 1p36 | 1p Deletion Syndrome |
| 3 | 3p25 - pter | 3p Deletion Syndrome |
| 3 | 3p21 - pter | 3p Duplication Syndrome |
| 4 | 4p16.3 | Wolf-Hirschhorn Syndrome |
| 4 | 4p15.2 - 16.1 | 4p Duplication Syndrome |
| 5 | 5p15.2 - pter | Cri du Chat Syndrome |
| 7 | 7p13.3 | Miller-Dieker Syndrome |
| 7 | 7p11.23 | William's Syndrome |
| 8 | 8q24.1 | Langer-Giedion Syndrome (LGS) |
| 8 | 8q24.1 | Trichorhinophalangeal Syndrome (TRPS) |
| 9 | 9p, usually 9p22 - pter | 9p Deletion Syndrome |
| 10 | 10p13p14 | DiGeorge Syndrome II |
| 11 | 11p13 | WAGR Syndrome |
| 11 | 11p15.5 | Beckwith-Wiedemann Syndrome |
| 11 | 11p11.2 | Potocki-Shaffer Syndrome (Multiple Exostoses II Locus) |
| 15 | 15q12 | Angelman Syndrome |
| 15 | 15q12 | Prader-Willi Syndrome |
| 16 | Distal 16p13.3 | Rubinstein-Taybi Syndrome |
| 17 | 17p12 | Charcot-Marie-Tooth Disease Type 1A(CMT-1A) |
| 17 | 17p12 | Hereditary Neuropathy with Liability to Pressure Palsies |
| 17 | 17p13.3 | Miller-Dieker Syndrome/Isolated Lissencephaly |
| 17 | 17p11.2 | Smith-Magenis Syndrome |
| 20 | 20p11.2p12 | Alagille Syndrome |
| 22 | 22q11.2 (also see 1-p13p14) | Digeoege/Velocardiofacial Syndrome |
| X | Xp21 | Adrenal Hypoplasia Congenita (AHC) |
| X | Xp21 | Duchenne/Becker Muscular Dystrophy |
| X | Xp21 | Glycerol Kinase Deficiency |
| X | Xp22 | Pelizaeus-Merzbacher Disease |
| X | Xp22.3 | Steroid Sulfatase Deficiency |
| Y | SRY locus/Yp | Abnormalities of the SRY locus |

The compilations, or sets, libraries or collections, of nucleic acids, arrays and methods of the invention can also be used to detect aneuploidy of chromosomes 13, 18, 21, X, and Y from genomic DNA from newborn uncultured blood samples (see, e.g., Jalal (1997) Mayo Clin. Proc. 72:705-710). Chromosomal abnormalities have been reported to occur in approximately 1%-2% of viable pregnancies studied by chorionic villus sampling at 9-11 weeks of gestation. See, e.g., Harrison (1993) Hum. Genet. 92:353-358.

In in vitro fertilization (IVF) programs, preimplantation genetic diagnosis (PGD) of oocytes and embryos has become the technique of choice to select against abnormal embryos before embryo transfer. Thus, in alternative aspects, the compilations, or sets, libraries or collections, of nucleic acids, arrays and methods of the invention are used for preimplantation genetic diagnosis and the diagnosis of chromosomal abnormalities and structural abnormalities in oocytes and embryos. See, e.g., Fung (2001) J. Histochem. Cytochem. 49:797-798. Thus, in alternative aspects, the compilations, or sets, libraries or collections, of nucleic acids, arrays and methods of the invention are used with chorionic villus sampling (CVS) and fetal karyotyping. See, e.g., Sanz (2001) Fetal Diagn. Ther. 16:95-97.

Genetic defects are frequent among transgenic animals produced by pronuclear microinjection. A successful method for the screening of founder animals for a chromosomal abnormality prior to mating would greatly reduce the costs associated with the propagation of the transgenic lines, and improve the efficiency of transgenic livestock production. Thus, in alternative aspects, the compilations, or sets, libraries or collections, of nucleic acids, arrays and methods of the invention are used in the production of transgenic animals, particularly, the screening of founder animals for gene defects prior to mating. See, e.g., Ibanez (2001) Mol. Reprod. Dev. 58:166-172.

Comparative Genomic Hybridization (CGH)

In one aspect, compilations, or sets, libraries or collections, of nucleic acids, the arrays and methods of the invention incorporate array-based comparative genomic hybridization (CGH) reactions to detect chromosomal abnormalities, e.g., contiguous gene abnormalities, in cell populations, such as tissue, e.g., biopsy or body fluid samples. CGH is a molecular cytogenetics approach that can be used to detect regions in a genome undergoing quantitative changes, e.g., gains or losses of sequence or copy numbers. Analysis of genomes of tumor cells can detect a region or regions of anomaly under going gains and/or losses.

CGH reactions compare the genetic composition of test versus controls samples; e.g., whether a test sample of genomic DNA (e.g., from a cell population suspected of having one or more subpopulations comprising different, or cumulative, genetic defects) has amplified or deleted or mutated segments, as compared to a "negative" control, e.g., "normal" or "wild type" genotype, or "positive" control, e.g., a known cancer cell or a cell with a known defect, e.g., a translocation or deletion or amplification or the like.

Making and using the compilations, or sets, libraries or collections, of nucleic acids, arrays and practicing the methods of the invention can incorporate all known methods and means and variations thereof for carrying out comparative genomic hybridization, see, e.g., U.S. Pat. Nos. 6,197,501; 6,159,685; 5,976,790; 5,965,362; 5,856,097; 5,830,645; 5,721,098; 5,665,549; 5,635,351; and, Diago (2001) American J. of Pathol. May; 158(5):1623-1631; Theillet (2001) Bull. Cancer 88:261-268; Werner (2001) Pharmacogenomics 2:25-36; Jain (2000) Pharmacogenomics 1:289-307.

Arrays, or "BioChips"

The invention provides articles of manufacture, such as arrays, comprising the compilations, or sets, libraries or collections, of nucleic acids of the invention. Making and using the compilations, or sets, libraries or collections, of nucleic acids, arrays and practicing the methods of the present invention can incorporate any known "array," also referred to as a "microarray" or "DNA array" or "nucleic acid array" or "biochip," or variation thereof. Arrays are generically a plurality of "target elements," or "spots," each target element comprising a defined amount of one or more biological molecules, e.g., polypeptides, nucleic acid molecules, or probes, immobilized on a defined location on a substrate surface. Typically, the immobilized biological molecules are contacted with a sample for specific binding, e.g., hybridization, between molecules in the sample and the array. Immobilized nucleic acids can contain sequences from specific messages (e.g., as cDNA libraries) or genes (e.g., genomic libraries), including, e.g., substantially all or a subsection of a chromosome or substantially all of a genome, including a human genome. Other target elements can contain reference sequences, such as positive and negative controls, and the like. The target elements of the arrays may be arranged on the substrate surface at different sizes and different densities. Different target elements of the arrays can have the same molecular species, but, at different amounts, densities, sizes, labeled or unlabeled, and the like. The target element sizes and densities will depend upon a number of factors, such as the nature of the label (the immobilized molecule can also be labeled), the substrate support (it is solid, semi-solid, fibrous, capillary or porous), and the like. Each target element may comprise substantially the same nucleic acid sequences, or, a mixture of nucleic acids of different lengths and/or sequences. Thus, for example, a target element may contain more than one copy of a cloned piece of DNA, and each copy may be broken into fragments of different lengths, as described herein. The length and complexity of the nucleic acid fixed onto the array surface is not critical to the invention. The array can comprise nucleic acids immobilized on any substrate, e.g., a solid surface (e.g., nitrocellulose, glass, quartz, fused silica, plastics and the like). See, e.g., U.S. Pat. No. 6,063,338 describing multi-well platforms comprising cycloolefin polymers if fluorescence is to be measured. Arrays used in the methods of the invention can comprise housing comprising components for controlling humidity and temperature during the hybridization and wash reactions.

In making and using the compilations, or sets, libraries or collections, of nucleic acids, arrays and practicing the methods of the invention, known arrays and methods of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765. The present invention can use any known array, e.g., GeneChips™, Affymetrix, Santa Clara, Calif.; SPECTRALCHIP™ Mouse BAC Arrays, SPECTRAL- CHIP™ Human BAC Arrays and Custom Arrays of Spectral Genomics, Houston, Tex., and their accompanying manufacturer's instructions.

In alternative embodiments, the compilations, or sets, libraries or collections, of nucleic acids of the invention, and the articles of manufacture, such as arrays, of the invention, can comprise one, several or all of the human genomic nucleic acid segments set forth below in Table 2 (listing 2474 clones derived from all/representing all 24 human chromosomes). These clones have RPI or CTB clone names; these descriptors for the clones can be found in Nature 409:953-958 (2001), "Integration of cytogenetic landmarks into the draft sequence of the human genome." The BAC Resource Consortium. The numbers in the right-hand column of Table 2 indicate the linear length of the cloned nucleic acid segment are megabases (Mb). These clones represent all 24 human chromosomes in about 1 Mb resolution.

TABLE 2

| clone_id | chromosome | linear |
|---|---|---|
| RP11-421C4 | 1 | 0.7 |
| RP1-283E3 | 1 | 0.9 |
| RP4-703E10 | 1 | 2.4 |
| RP1-163G9 | 1 | 2.8 |
| RP11-447M5 | 1 | 4.4 |
| RP3-491M17 | 1 | 4.7 |
| RP11-33M12 | 1 | 5.4 |
| RP3-438L4 | 1 | 6.4 |
| RP3-330O12 | 1 | 8.2 |
| RP4-633I8 | 1 | 9.1 |
| RP11-476D13 | 1 | 9.6 |
| AL358492.9 | 1 | 10.9 |
| RP5-888M10 | 1 | 12 |
| RP11-219C24 | 1 | 12.4 |
| RP4-726F20 | 1 | 13.8 |
| RP5-864I18 | 1 | 14.6 |
| RP11-169K16 | 1 | 15.7 |
| RP1-163M9 | 1 | 16.4 |
| RP1-37C10 | 1 | 17.2 |
| RP11-79D15 | 1 | 18 |
| RP1-8B22 | 1 | 18.8 |
| RP11-91K11 | 1 | 20.1 |
| RP3-340N1 | 1 | 20.5 |
| RP5-886K2 | 1 | 24.4 |
| RP3-462O23 | 1 | 25.2 |
| RP3-465N24 | 1 | 26 |
| RP1-125I3 | 1 | 26.6 |
| RP11-261P19 | 1 | 27.8 |
| RP1-50O24 | 1 | 29 |
| RP1-212P9 | 1 | 29.7 |
| RP3-437I16 | 1 | 30.1 |
| RP5-893G23 | 1 | 31.2 |
| RP4-655C4 | 1 | 33.3 |
| AL033524.11 | 1 | 34.1 |
| RP3-423B22 | 1 | 35.5 |
| RP1-93K19 | 1 | 36.2 |
| RP1-117O3 | 1 | 37.9 |
| RP5-1007G16 | 1 | 38.6 |
| RP1-34M23 | 1 | 39.5 |
| RP4-811I8 | 1 | 40.6 |
| AL512599 | 1 | 41.7 |
| RP1-92O14 | 1 | 44.4 |
| RP5-1029K14 | 1 | 45.3 |
| RP11-319C21 | 1 | 46.1 |
| RP5-820O16 | 1 | 47.2 |
| RP4-639P2 | 1 | 48.2 |
| RP11-112C15 | 1 | 48.9 |
| RP5-965L7 | 1 | 50.3 |
| RP11-116M11 | 1 | 51.5 |
| RP5-1013G21 | 1 | 52.1 |
| RP11-253A20 | 1 | 52.4 |
| RP4-814E15 | 1 | 53.4 |
| RP5-1024N4 | 1 | 55.5 |
| RP11-13N22 | 1 | 56.5 |

TABLE 2-continued

| clone_id | chromosome | linear |
|---|---|---|
| RP11-79A13 | 1 | 57.1 |
| RP11-89O16 | 1 | 57.7 |
| RP4-737A23 | 1 | 58.6 |
| RP11-63G10 | 1 | 59.5 |
| RP11-89D5 | 1 | 61.3 |
| RP3-333A15 | 1 | 62.4 |
| RP4-685B19 | 1 | 63.3 |
| RP11-79O23 | 1 | 64 |
| RP11-205P11 | 1 | 65.3 |
| RP5-879H24 | 1 | 66.8 |
| RP4-542O18 | 1 | 67.3 |
| RP11-221L2 | 1 | 67.9 |
| RP6-65F20 | 1 | 68.9 |
| RP4-662P1 | 1 | 69.7 |
| RP11-5P4 | 1 | 71.4 |
| RP4-534K7 | 1 | 71.9 |
| RP4-537F10 | 1 | 72.3 |
| RP11-75N16 | 1 | 73.4 |
| RP11-26A10 | 1 | 74.7 |
| RP11-131O15 | 1 | 75.7 |
| RP11-89K2 | 1 | 76.9 |
| RP11-88B10 | 1 | 78 |
| RP11-492C3 | 1 | 79.5 |
| RP4-595K12 | 1 | 79.7 |
| RP5-1153M13 | 1 | 80.8 |
| RP11-80G24 | 1 | 81.7 |
| RP5-831O21 | 1 | 82.8 |
| RP4-572F19 | 1 | 83.6 |
| RP5-989D17 | 1 | 84.8 |
| RP11-79I13 | 1 | 85.7 |
| RP4-612J11 | 1 | 86 |
| RP4-601K24 | 1 | 86.9 |
| RP5-896C23 | 1 | 88 |
| RP11-78E18 | 1 | 88.2 |
| RP4-552O12 | 1 | 89.1 |
| RP11-193H16 | 1 | 90.7 |
| AL122002.16 | 1 | 91.7 |
| RP5-1027O11 | 1 | 92.9 |
| RP5-905H16 | 1 | 93.8 |
| RP5-1007M22 | 1 | 94.5 |
| RP5-871E2 | 1 | 95 |
| RP11-99A8 | 1 | 95.6 |
| RP11-47K11 | 1 | 96.5 |
| RP11-79M15 | 1 | 98.2 |
| RP11-163M2 | 1 | 98.9 |
| RP4-713B5 | 1 | 99.7 |
| RP11-148B18 | 1 | 100.9 |
| RP11-48A6 | 1 | 101.7 |
| RP11-335D10 | 1 | 102 |
| RP11-122C9 | 1 | 103.2 |
| RP4-672J20 | 1 | 104.5 |
| RP11-79C3 | 1 | 105 |
| RP11-90N15 | 1 | 105.4 |
| RP11-411H5 | 1 | 108.5 |
| RP11-79H19 | 1 | 109 |
| RP11-259N12 | 1 | 110.5 |
| RP4-669H10 | 1 | 113 |
| RP5-1077K16 | 1 | 113.8 |
| RP11-96F24 | 1 | 114.6 |
| RP11-180N18 | 1 | 117.6 |
| RP5-1125M8 | 1 | 118.9 |
| RP4-773A18 | 1 | 119.2 |
| RP4-580L15 | 1 | 120.3 |
| RP5-1156J9 | 1 | 122.1 |
| RP11-90J3 | 1 | 124 |
| RP11-88D6 | 1 | 124.2 |
| RP11-315I20 | 1 | 126.1 |
| RP4-599G15 | 1 | 128.4 |
| RP4-787H6 | 1 | 130.5 |
| RP11-433J22 | 1 | 149.1 |
| RP11-458I7 | 1 | 149.9 |
| RP4-790G17 | 1 | 150.3 |
| RP11-71L20 | 1 | 151.6 |
| RP11-81P11 | 1 | 153.1 |
| RP1-148L21 | 1 | 153.8 |
| RP11-137P24 | 1 | 154.6 |
| RP11-77I10 | 1 | 161 |

TABLE 2-continued

| clone_id | chromosome | linear |
|---|---|---|
| RP11-80F2 | 1 | 162.4 |
| RP11-260G23 | 1 | 163.2 |
| RP11-90A11 | 1 | 164.6 |
| RP11-80B20 | 1 | 165 |
| RP11-80D6 | 1 | 166.4 |
| RP1-9E21 | 1 | 167.9 |
| RP11-354K16 | 1 | 169.4 |
| Z99572.1 | 1 | 170.8 |
| RP11-81H19 | 1 | 172 |
| RP11-89P2 | 1 | 173.2 |
| RP11-79E17 | 1 | 174.4 |
| RP11-469I6 | 1 | 175.5 |
| RP1-105D12 | 1 | 175.8 |
| RP3-395P12 | 1 | 176.4 |
| RP11-415M14 | 1 | 178.2 |
| RP11-91K17 | 1 | 179 |
| RP11-90C19 | 1 | 179.5 |
| RP4-593C16 | 1 | 180.7 |
| AL022171 | 1 | 182.3 |
| RP11-12M5 | 1 | 183.3 |
| RP11-375F5 | 1 | 184.2 |
| RP11-46A10 | 1 | 184.6 |
| RP11-98G7 | 1 | 185 |
| RP11-317P15 | 1 | 186 |
| RP11-452O22 | 1 | 187.7 |
| RP11-63O2 | 1 | 188.7 |
| RP1-53A19 | 1 | 189.7 |
| RP11-79I7 | 1 | 190.3 |
| RP4-799N4 | 1 | 191.8 |
| RP11-71C11 | 1 | 192.9 |
| RP11-91N1 | 1 | 193 |
| RP11-113I24 | 1 | 194.4 |
| RP3-419C19 | 1 | 197.7 |
| RP11-101E13 | 1 | 197.9 |
| RP11-358A9 | 1 | 198.8 |
| RP11-173E24 | 1 | 201.4 |
| RP11-88D12 | 1 | 201.7 |
| RP11-91G12 | 1 | 202.5 |
| RP11-88N22 | 1 | 204.3 |
| RP11-80N24 | 1 | 205.1 |
| AF190464.1 | 1 | 207 |
| RP11-150L7 | 1 | 208.1 |
| RP11-335O13 | 1 | 209.2 |
| RP11-80N9 | 1 | 210.4 |
| RP11-243M13 | 1 | 211.2 |
| RP11-246J15 | 1 | 212.1 |
| RP11-35C1 | 1 | 214.1 |
| RP11-45F21 | 1 | 214.5 |
| RP11-79M12 | 1 | 216.3 |
| RP11-89N3 | 1 | 217 |
| RP11-90A5 | 1 | 219.9 |
| RP11-91G6 | 1 | 220.1 |
| RP11-79H5 | 1 | 223.4 |
| RP11-260A10 | 1 | 224.6 |
| RP11-66M7 | 1 | 224.7 |
| RP11-135J2 | 1 | 226.9 |
| RP11-553F10 | 1 | 227.6 |
| RP11-124J24 | 1 | 228.5 |
| RP11-239E10 | 1 | 231.6 |
| RP5-1090A23 | 1 | 232.2 |
| RP11-543G21 | 1 | 232.7 |
| RP11-275O4 | 1 | 234.5 |
| RP5-915N17 | 1 | 235.4 |
| RP11-108F13 | 1 | 236.5 |
| RP11-543E8 | 1 | 237.6 |
| RP5-865N13 | 1 | 238.9 |
| RP5-1016N21 | 1 | 240.2 |
| RP5-885P2 | 1 | 240.9 |
| RP4-781K5 | 1 | 241.8 |
| RP4-670F13 | 1 | 243.8 |
| RP11-80P14 | 1 | 245.4 |
| RP11-136B18 | 1 | 245.6 |
| RP11-90L13 | 1 | 247 |
| RP11-81J5 | 1 | 247.8 |
| AL365366.19 | 1 | 249.3 |
| RP11-28E22 | 1 | 250.4 |
| RP1-241M7 | 1 | 251.9 |
| RP11-152M6 | 1 | 252.5 |
| RP11-656O22 | 1 | 252.7 |
| RP11-88H4 | 1 | 254.4 |
| RP11-91C5 | 1 | 254.5 |
| RP11-407H12 | 1 | 256.1 |
| RP11-438F14 | 1 | 256.1 |
| RP11-1N7 | 2 | 0.1 |
| RP11-90H11 | 2 | 1.6 |
| RP11-352J11 | 2 | 1.7 |
| AC011995.8 | 2 | 2.2 |
| RP11-457A20 | 2 | 2.6 |
| RP11-36C8 | 2 | 2.9 |
| RP11-513H7 | 2 | 4 |
| RP11-350H23 | 2 | 4.9 |
| AC007464.4 | 2 | 7.2 |
| RP11-327F6 | 2 | 8 |
| RP11-484O9 | 2 | 10.9 |
| RP11-91E9 | 2 | 12.8 |
| RP11-282G6 | 2 | 15.6 |
| RP11-79E20 | 2 | 16.6 |
| RP11-80H16 | 2 | 19.9 |
| RP11-414D15 | 2 | 22.9 |
| RP11-443B20 | 2 | 24.2 |
| RP11-91I23 | 2 | 24.9 |
| RP11-88F6 | 2 | 25.9 |
| RP11-45M3 | 2 | 26.8 |
| AC024386.5 | 2 | 27.8 |
| RP11-328L16 | 2 | 28.7 |
| RP11-62F14 | 2 | 30 |
| RP11-93O2 | 2 | 31.1 |
| RP11-444D15 | 2 | 31.2 |
| RP11-3J7 | 2 | 32.4 |
| RP11-77G15 | 2 | 34 |
| RP11-119B15 | 2 | 35.7 |
| RP11-89F19 | 2 | 38.3 |
| RP11-555N21 | 2 | 39 |
| RP11-299C5 | 2 | 42.5 |
| RP11-119J12 | 2 | 44.3 |
| AC084265.2 | 2 | 45.9 |
| RP11-130P22 | 2 | 46.5 |
| RP11-436K12 | 2 | 47.9 |
| RP11-89G16 | 2 | 49.7 |
| AC016714.5 | 2 | 53.9 |
| RP11-321E13 | 2 | 56.2 |
| RP11-494H5 | 2 | 56.8 |
| RP11-482H16 | 2 | 57.4 |
| RP11-81L7 | 2 | 58 |
| RP11-90D1 | 2 | 60.2 |
| RP11-81L13 | 2 | 61.3 |
| RP11-79K21 | 2 | 62.1 |
| RP11-355B11 | 2 | 62.7 |
| RP11-240J3 | 2 | 64.9 |
| RP11-90B13 | 2 | 65.7 |
| RP11-88F20 | 2 | 66.2 |
| RP11-79H11 | 2 | 66.6 |
| RP11-340F16 | 2 | 67.3 |
| RP11-474G23 | 2 | 68.1 |
| RP11-179G23 | 2 | 69.5 |
| RP11-401N16 | 2 | 70.7 |
| RP11-175A7 | 2 | 71.5 |
| RP11-356H17 | 2 | 72.4 |
| AC013408 | 2 | 73.9 |
| AC007681.3 | 2 | 76 |
| AC016758 | 2 | 78.1 |
| RP11-91F23 | 2 | 78.3 |
| RP11-79C11 | 2 | 79.2 |
| RP11-79D19 | 2 | 80.1 |
| RP11-79O3 | 2 | 81.4 |
| RP11-89C12 | 2 | 82.7 |
| RP11-345F13 | 2 | 84.3 |
| RP11-451C8 | 2 | 84.6 |
| RP11-4C8 | 2 | 87.1 |
| RP11-90C7 | 2 | 87.6 |
| RP11-21P18 | 2 | 88.4 |
| RP11-554H10 | 2 | 88.7 |
| RP11-81F3 | 2 | 91.9 |
| AC013270.5 | 2 | 92.5 |

TABLE 2-continued

| clone_id | chromosome | linear |
|---|---|---|
| RP11-89J19 | 2 | 93 |
| RP11-629A22 | 2 | 94 |
| RP11-38C17 | 2 | 94.8 |
| RP11-89L1 | 2 | 95.5 |
| RP11-90J9 | 2 | 96.3 |
| RP11-315O22 | 2 | 101 |
| RP11-83A12 | 2 | 101.3 |
| RP11-289J14 | 2 | 101.9 |
| RP11-89O22 | 2 | 102.6 |
| RP11-90O9 | 2 | 103 |
| RP11-88F14 | 2 | 103.8 |
| RP11-89O10 | 2 | 104.1 |
| AC010978.7 | 2 | 104.6 |
| RP11-464P18 | 2 | 105.4 |
| RP11-79K7 | 2 | 106.4 |
| AC092645.1 | 2 | 109.2 |
| RP11-368K23 | 2 | 110.3 |
| RP11-91C22 | 2 | 111.3 |
| RP11-89L12 | 2 | 112.3 |
| RP11-98C1 | 2 | 113.8 |
| RP11-434I13 | 2 | 114.4 |
| RP11-17N4 | 2 | 116.6 |
| RP11-438O12 | 2 | 117.6 |
| RP11-90K23 | 2 | 118.5 |
| RP11-498O20 | 2 | 119.5 |
| RP11-91G8 | 2 | 121.7 |
| RP11-270M20 | 2 | 122.2 |
| RP11-67G15 | 2 | 123.8 |
| RP11-140B20 | 2 | 124.4 |
| RP11-88B6 | 2 | 125.5 |
| RP11-81H7 | 2 | 125.9 |
| RP11-32C20 | 2 | 126.9 |
| RP11-91K13 | 2 | 127.1 |
| RP11-89B17 | 2 | 128.2 |
| RP11-294I11 | 2 | 128.8 |
| AC097499.2 | 2 | 129.8 |
| RP11-467A23 | 2 | 130.8 |
| RP11-289K3 | 2 | 131.8 |
| RP11-81H1 | 2 | 132.9 |
| AC010873.12 | 2 | 133.8 |
| RP11-119N3 | 2 | 133.9 |
| RP11-472M4 | 2 | 134.6 |
| RP11-231E19 | 2 | 134.9 |
| RP11-91C20 | 2 | 136.2 |
| RP11-434H14 | 2 | 137.9 |
| AC009957.10 | 2 | 138.2 |
| RP11-67J2 | 2 | 138.9 |
| RP11-357J9 | 2 | 139 |
| RP11-29N17 | 2 | 141.8 |
| RP11-90K5 | 2 | 143.6 |
| AC018465.7 | 2 | 144.9 |
| RP11-375H16 | 2 | 145.3 |
| RP11-91A11 | 2 | 147.6 |
| RP11-79A11 | 2 | 149 |
| RP11-364H22 | 2 | 149.6 |
| RP11-185M22 | 2 | 150.6 |
| RP11-17E6 | 2 | 151.4 |
| RP11-11C17 | 2 | 152.4 |
| RP11-44N6 | 2 | 153.4 |
| RP11-79B5 | 2 | 154.8 |
| RP11-546J1 | 2 | 157.1 |
| RP11-91K6 | 2 | 158.4 |
| RP11-50J20 | 2 | 159.1 |
| RP11-615B17 | 2 | 159.3 |
| RP11-79L13 | 2 | 161 |
| AC010876 | 2 | 161.5 |
| AC092632.1 | 2 | 162.1 |
| AC016723.10 | 2 | 165.9 |
| RP11-79E23 | 2 | 167.2 |
| RP11-91O10 | 2 | 167.8 |
| RP11-80D14 | 2 | 170 |
| RP11-81F17 | 2 | 170.1 |
| RP11-91L3 | 2 | 170.8 |
| RP11-79D11 | 2 | 171.8 |
| RP11-91L23 | 2 | 172.2 |
| RP11-91A9 | 2 | 172.3 |
| RP11-79C17 | 2 | 172.6 |
| AC013467.8 | 2 | 173.4 |
| RP11-12N7 | 2 | 174.5 |
| RP11-279N12 | 2 | 176.2 |
| RP11-428I14 | 2 | 177.1 |
| RP11-88L24 | 2 | 178.1 |
| RP11-30N9 | 2 | 179.4 |
| RP11-131G20 | 2 | 179.8 |
| RP11-69G4 | 2 | 181.5 |
| RP11-598C21 | 2 | 182.4 |
| AC074182.6 | 2 | 183 |
| RP11-270G18 | 2 | 188.5 |
| RP11-88L20 | 2 | 188.6 |
| AC046197 | 2 | 189.8 |
| RP11-192M8 | 2 | 190.4 |
| RP11-59L22 | 2 | 191.1 |
| RP11-30M1 | 2 | 193.5 |
| RP11-90C17 | 2 | 194.1 |
| RP11-387H5 | 2 | 195.4 |
| RP11-89B13 | 2 | 195.7 |
| RP11-2C13 | 2 | 197 |
| AC020718.6 | 2 | 198.3 |
| RP11-91M5 | 2 | 200.4 |
| RP11-329O10 | 2 | 202.6 |
| RP11-47E6 | 2 | 203.5 |
| AC009498.3 | 2 | 203.9 |
| RP11-15J24 | 2 | 204.4 |
| RP11-89K8 | 2 | 205.2 |
| RP11-90D19 | 2 | 205.9 |
| RP11-89J16 | 2 | 206.8 |
| RP11-13N10 | 2 | 207.7 |
| RP11-90O3 | 2 | 208.9 |
| RP11-79C24 | 2 | 210.5 |
| RP11-300D24 | 2 | 211.3 |
| RP11-560C24 | 2 | 212.6 |
| RP11-44J16 | 2 | 213.6 |
| AC073284.3 | 2 | 215.2 |
| RP11-4B6 | 2 | 217.2 |
| RP11-146N10 | 2 | 218.2 |
| RP11-316O14 | 2 | 219.2 |
| AC009310.3 | 2 | 219.7 |
| RP11-23G2 | 2 | 220.9 |
| AC009231.4 | 2 | 221.6 |
| RP11-247E23 | 2 | 222.6 |
| RP11-551D18 | 2 | 223.4 |
| RP11-79C2 | 2 | 223.8 |
| RP11-89F8 | 2 | 226.8 |
| RP11-91J17 | 2 | 226.8 |
| AC009950 | 2 | 227.6 |
| RP11-91C14 | 2 | 228 |
| RP11-252C12 | 2 | 229.1 |
| RP11-69J7 | 2 | 230.4 |
| RP11-71H20 | 2 | 231.2 |
| RP11-91N19 | 2 | 232.5 |
| RP11-176L22 | 2 | 232.7 |
| RP11-79G2 | 2 | 234.2 |
| RP11-21K1 | 2 | 234.7 |
| RP11-680O16 | 2 | 235.7 |
| RP11-155J6 | 2 | 236.4 |
| RP11-88P18 | 2 | 237.5 |
| RP11-118M12 | 2 | 239.8 |
| RP11-89N23 | 2 | 240.3 |
| RP11-463B12 | 2 | 241 |
| RP11-204C23 | 3 | 3 |
| RP11-32F23 | 3 | 4.1 |
| RP11-63O1 | 3 | 4.8 |
| RP11-91K16 | 3 | 6.3 |
| RP11-33E18 | 3 | 7.9 |
| RP11-271E2 | 3 | 9.2 |
| RP11-21J23 | 3 | 10.4 |
| RP11-91K4 | 3 | 11.5 |
| RP11-115G3 | 3 | 13.3 |
| RP11-105H19 | 3 | 13.8 |
| RP11-57D6 | 3 | 15.7 |
| RP11-255O19 | 3 | 18.3 |
| RP11-80D24 | 3 | 19.7 |
| RP11-451A20 | 3 | 22 |
| RP11-90I9 | 3 | 22.3 |

TABLE 2-continued

| clone_id | chromosome | linear |
|---|---|---|
| RP11-79E6 | 3 | 23.7 |
| RP11-89F18 | 3 | 25.8 |
| RP11-41F5 | 3 | 26.1 |
| RP11-245E5 | 3 | 26.7 |
| RP11-421F9 | 3 | 27.8 |
| RP11-451C4 | 3 | 28 |
| AC013500.4 | 3 | 29.8 |
| RP11-11L6 | 3 | 30.7 |
| RP11-103N21 | 3 | 31.8 |
| RP11-56P22 | 3 | 35.9 |
| RP11-286G5 | 3 | 37.2 |
| RP11-90M23 | 3 | 38.6 |
| RP11-90B15 | 3 | 40.7 |
| RP11-241P3 | 3 | 42.6 |
| RP11-219I21 | 3 | 43.1 |
| RP11-24L15 | 3 | 44.3 |
| RP11-348P10 | 3 | 45.3 |
| RP11-91E8 | 3 | 46.4 |
| RP11-425J9 | 3 | 47.6 |
| RP11-91M18 | 3 | 48 |
| RP11-804H8 | 3 | 51 |
| RP11-89F17 | 3 | 51.6 |
| RP11-865O5 | 3 | 53.6 |
| RP11-124O2 | 3 | 54.8 |
| RP11-189K9 | 3 | 55 |
| RP11-754F19 | 3 | 57.2 |
| RP11-80H18 | 3 | 58.2 |
| RP11-79K17 | 3 | 59.2 |
| RP11-34D21 | 3 | 60.7 |
| RP11-88P20 | 3 | 63.2 |
| RP11-108A8 | 3 | 64 |
| RP11-89O2 | 3 | 64.9 |
| RP11-129B22 | 3 | 65 |
| RP11-88H12 | 3 | 66.2 |
| RP11-146E16 | 3 | 67.9 |
| RP11-89A12 | 3 | 68.2 |
| RP11-79C12 | 3 | 68.3 |
| RP11-81N13 | 3 | 68.3 |
| RP11-444P10 | 3 | 70 |
| RP11-90H15 | 3 | 71.6 |
| RP11-522N9 | 3 | 73.1 |
| RP11-781E19 | 3 | 74.8 |
| RP11-89H10 | 3 | 76.1 |
| RP11-79O5 | 3 | 76.4 |
| RP11-447J13 | 3 | 78.2 |
| RP11-79F5 | 3 | 80.3 |
| RP11-220O14 | 3 | 80.7 |
| AC018918 | 3 | 81.5 |
| RP11-208G16 | 3 | 86.5 |
| RP11-81P15 | 3 | 89.2 |
| RP11-424C9 | 3 | 90 |
| RP11-91A15 | 3 | 96.4 |
| AC019233.7 | 3 | 97.4 |
| RP11-91M15 | 3 | 98.4 |
| RP11-449F7 | 3 | 100.5 |
| RP11-114I8 | 3 | 103.1 |
| AC018352.13 | 3 | 103.7 |
| RP11-490H13 | 3 | 106.5 |
| RP11-90I19 | 3 | 108 |
| RP11-91B3 | 3 | 108.7 |
| RP11-71D1 | 3 | 113.1 |
| RP11-12P11 | 3 | 114.8 |
| RP11-745L2 | 3 | 115 |
| RP11-79H17 | 3 | 115.2 |
| RP11-5K13 | 3 | 116.9 |
| RP11-24O5 | 3 | 117.1 |
| RP11-342J15 | 3 | 118.3 |
| RP11-373C21 | 3 | 119.8 |
| AC027296.12 | 3 | 120.3 |
| RP11-91F9 | 3 | 120.6 |
| RP11-169N13 | 3 | 122 |
| RP11-217N3 | 3 | 123.3 |
| RP11-10G15 | 3 | 125.6 |
| RP11-79M2 | 3 | 126.7 |
| RP11-25L9 | 3 | 128.6 |
| RP11-59J16 | 3 | 130.5 |
| RP11-205A6 | 3 | 131.8 |
| RP11-525K18 | 3 | 133 |
| RP11-452H12 | 3 | 134.1 |
| RP11-446K3 | 3 | 137.3 |
| RP11-79L21 | 3 | 138.3 |
| RP11-91K8 | 3 | 138.9 |
| RP11-91O5 | 3 | 140.4 |
| RP11-220J13 | 3 | 141.1 |
| RP11-566E10 | 3 | 141.8 |
| RP11-197K1 | 3 | 142.2 |
| RP11-630C21 | 3 | 143.6 |
| RP11-79L9 | 3 | 144.6 |
| RP11-548O1 | 3 | 144.8 |
| RP11-166D18 | 3 | 145.8 |
| RP11-89E16 | 3 | 146.2 |
| RP11-372E1 | 3 | 148.8 |
| RP11-80H8 | 3 | 149 |
| RP11-260J24 | 3 | 149.9 |
| RP11-88H10 | 3 | 151.7 |
| RP11-229G6 | 3 | 155.5 |
| RP11-145F16 | 3 | 156.4 |
| RP11-385G14 | 3 | 157.2 |
| RP11-362A9 | 3 | 158.4 |
| RP11-372M20 | 3 | 159.8 |
| RP11-451C20 | 3 | 160.7 |
| RP11-286N6 | 3 | 162.1 |
| RP11-392A22 | 3 | 163.2 |
| RP11-90N21 | 3 | 164 |
| RP11-79A14 | 3 | 164.1 |
| RP11-91L9 | 3 | 164.7 |
| RP11-79M21 | 3 | 164.9 |
| RP11-209H21 | 3 | 166.5 |
| RP11-203L15 | 3 | 167.7 |
| RP11-79G24 | 3 | 168.6 |
| RP11-90M7 | 3 | 170.1 |
| RP11-79F11 | 3 | 171.1 |
| RP11-80L14 | 3 | 171.1 |
| RP11-91B7 | 3 | 173.3 |
| AC018356.25 | 3 | 176.1 |
| RP11-151A21 | 3 | 176.4 |
| RP11-172G5 | 3 | 177.2 |
| RP11-91A17 | 3 | 179.4 |
| RP11-44A1 | 3 | 180.2 |
| RP11-89J17 | 3 | 180.7 |
| RP11-278A4 | 3 | 183 |
| RP11-114M1 | 3 | 183.4 |
| RP11-91K9 | 3 | 183.7 |
| RP11-89B3 | 3 | 185.1 |
| RP11-45I24 | 3 | 185.4 |
| RP11-510K16 | 3 | 186.2 |
| RP11-275H4 | 3 | 186.7 |
| RP11-259I19 | 3 | 187.9 |
| RP11-102G2 | 3 | 188.4 |
| RP11-63G1 | 3 | 189.7 |
| RP11-79K10 | 3 | 190.5 |
| RP11-379C23 | 3 | 191.6 |
| RP11-88P6 | 3 | 192.6 |
| RP11-67E18 | 3 | 194.6 |
| RP11-54L9 | 3 | 196.1 |
| RP11-88H6 | 3 | 197.1 |
| RP11-608P9 | 3 | 197.6 |
| RP11-91M9 | 3 | 198.2 |
| RP11-326J2 | 3 | 200.1 |
| RP11-313F11 | 3 | 201.8 |
| RP11-778E2 | 3 | 202.9 |
| RP11-338O10 | 3 | 204.6 |
| AC018707.5 | 3 | 204.9 |
| AC092535.3 | 4 | 0.7 |
| RP11-572O17 | 4 | 1.1 |
| RP11-262P20 | 4 | 1.2 |
| RP11-478C1 | 4 | 1.9 |
| RP3-323A24 | 4 | 2.8 |
| RP11-520M5 | 4 | 4 |
| RP11-808B21 | 4 | 4.5 |
| RP11-357G3 | 4 | 5.3 |
| AC004555.2 | 4 | 7.6 |
| RP11-101J14 | 4 | 9.3 |
| RP11-17I9 | 4 | 10.6 |

TABLE 2-continued

| clone_id | chromosome | linear |
|---|---|---|
| RP11-34C20 | 4 | 11.9 |
| RP11-79G9 | 4 | 13.4 |
| RP11-81N5 | 4 | 14 |
| RP11-89K12 | 4 | 14.6 |
| RP11-81L15 | 4 | 15.5 |
| RP11-91N13 | 4 | 16.8 |
| RP11-206O9 | 4 | 17.1 |
| RP11-89H17 | 4 | 18.2 |
| RP11-79N22 | 4 | 19.4 |
| RP11-11M9 | 4 | 20.1 |
| RP11-91B20 | 4 | 20.8 |
| RP11-151G21 | 4 | 21.9 |
| RP11-238L9 | 4 | 22.2 |
| RP11-88B22 | 4 | 23.9 |
| RP11-660M5 | 4 | 26.9 |
| RP11-239C17 | 4 | 28.4 |
| RP11-89I6 | 4 | 31.6 |
| RP11-53F2 | 4 | 32.1 |
| RP11-363G1 | 4 | 32.2 |
| RP11-81H11 | 4 | 33.9 |
| RP11-79E3 | 4 | 35.8 |
| RP11-81N11 | 4 | 36.6 |
| RP11-108H14 | 4 | 38.9 |
| RP11-24G16 | 4 | 40 |
| RP11-472B18 | 4 | 41.5 |
| RP11-138F23 | 4 | 42.7 |
| RP11-227F19 | 4 | 43.4 |
| RP11-91F19 | 4 | 44.4 |
| RP11-90L23 | 4 | 45.1 |
| RP11-89N6 | 4 | 49.7 |
| RP11-109P3 | 4 | 50 |
| AC022904.3 | 4 | 52.9 |
| RP11-80L11 | 4 | 55.4 |
| AC069068.9 | 4 | 56.4 |
| RP11-7J22 | 4 | 57.4 |
| RP11-319E12 | 4 | 58.3 |
| RP11-89B16 | 4 | 59.8 |
| RP11-91C3 | 4 | 61 |
| RP11-24I7 | 4 | 62.8 |
| RP11-63E13 | 4 | 66.5 |
| RP11-89M12 | 4 | 68.3 |
| RP11-642E20 | 4 | 69 |
| RP11-529K3 | 4 | 70.5 |
| RP11-121P15 | 4 | 71.3 |
| RP11-89G2 | 4 | 71.7 |
| RP11-373J21 | 4 | 72.7 |
| RP11-155P6 | 4 | 73.8 |
| RP11-88J6 | 4 | 74.6 |
| RP11-144I19 | 4 | 76.2 |
| RP11-49H14 | 4 | 77.5 |
| RP11-79M16 | 4 | 78 |
| RP11-17P19 | 4 | 78.4 |
| AC021127.8 | 4 | 80.5 |
| RP11-110P12 | 4 | 81.3 |
| RP11-449B1 | 4 | 83 |
| RP11-91J11 | 4 | 83.7 |
| RP11-36G19 | 4 | 84.5 |
| RP11-91E6 | 4 | 86.4 |
| RP11-397E7 | 4 | 87.3 |
| RP11-203P12 | 4 | 87.5 |
| RP11-17P8 | 4 | 88.9 |
| RP11-79M20 | 4 | 89.8 |
| RP11-49M7 | 4 | 90.7 |
| RP11-451M10 | 4 | 91.3 |
| RP11-16I17 | 4 | 94.3 |
| RP11-21O14 | 4 | 96.8 |
| RP11-369I16 | 4 | 98.2 |
| RP11-144B4 | 4 | 99.3 |
| RP11-414I7 | 4 | 100.8 |
| RP11-91G13 | 4 | 103 |
| RP11-26E14 | 4 | 104.5 |
| RP11-91C2 | 4 | 105.2 |
| RP11-88D10 | 4 | 107.8 |
| RP11-80H22 | 4 | 109.9 |
| RP11-81J9 | 4 | 110 |
| RP11-89G6 | 4 | 110.3 |
| RP11-144H4 | 4 | 111.1 |
| RP11-380D23 | 4 | 112.1 |
| RP11-18D18 | 4 | 112.9 |
| RP11-89D13 | 4 | 113.2 |
| RP11-73K9 | 4 | 113.8 |
| RP11-260E23 | 4 | 115.2 |
| RP11-362M19 | 4 | 116 |
| RP11-778G8 | 4 | 118.8 |
| RP11-21I10 | 4 | 119.7 |
| RP11-101N17 | 4 | 119.9 |
| AC007512.2 | 4 | 121.1 |
| RP11-647P12 | 4 | 122.4 |
| RP11-100E15 | 4 | 123.9 |
| RP11-27C19 | 4 | 124.7 |
| RP11-728C8 | 4 | 125.2 |
| RP11-79I18 | 4 | 126.1 |
| RP11-89D9 | 4 | 126.9 |
| RP11-77P11 | 4 | 128.4 |
| RP11-11P20 | 4 | 129.2 |
| RP11-184M15 | 4 | 130.2 |
| RP11-14N24 | 4 | 131.4 |
| RP11-80P12 | 4 | 132.2 |
| RP11-94J9 | 4 | 134.8 |
| RP11-89P23 | 4 | 135.7 |
| RP11-81F5 | 4 | 136.8 |
| RP11-60A1 | 4 | 137.8 |
| AC016487.5 | 4 | 138.3 |
| RP11-53C1 | 4 | 139.6 |
| AC019343.3 | 4 | 141 |
| RP11-5K16 | 4 | 141.9 |
| RP11-79E2 | 4 | 143 |
| RP11-739G21 | 4 | 143.4 |
| RP11-122I3 | 4 | 144.7 |
| RP11-89E4 | 4 | 145.5 |
| AC032008.2 | 4 | 147 |
| RP11-91O3 | 4 | 148.1 |
| RP11-56F3 | 4 | 149 |
| RP11-24I21 | 4 | 150.6 |
| RP11-77F4 | 4 | 152.3 |
| RP11-73G16 | 4 | 153.3 |
| RP11-119B13 | 4 | 154.6 |
| RP11-136D2 | 4 | 157.9 |
| RP11-17C4 | 4 | 158.7 |
| RP11-89C4 | 4 | 159.8 |
| RP11-81P7 | 4 | 160.9 |
| AC011101.4 | 4 | 162.2 |
| RP11-177L7 | 4 | 163.4 |
| RP11-808H17 | 4 | 163.6 |
| RP11-79E19 | 4 | 166.4 |
| RP11-6F19 | 4 | 167 |
| RP11-36G9 | 4 | 170 |
| RP11-90E13 | 4 | 171.1 |
| RP11-90D5 | 4 | 173.2 |
| RP11-110O14 | 4 | 174.5 |
| RP11-89D7 | 4 | 174.9 |
| RP11-134F18 | 4 | 175.6 |
| RP11-122D8 | 4 | 177.5 |
| RP11-79K2 | 4 | 178 |
| RP11-62B4 | 4 | 179 |
| RP11-79G20 | 4 | 180.5 |
| RP11-80P4 | 4 | 181.8 |
| RP11-244K2 | 4 | 182.6 |
| RP11-125M9 | 4 | 182.8 |
| RP11-18D7 | 4 | 183.9 |
| RP11-90E7 | 4 | 184.8 |
| RP11-267E24 | 4 | 185.6 |
| RP11-279K24 | 4 | 186.8 |
| RP11-597P9 | 4 | 187.5 |
| RP11-91J3 | 4 | 188.5 |
| AC025775.4 | 5 | 1.9 |
| RP11-20B3 | 5 | 2.7 |
| RP11-89N22 | 5 | 3.2 |
| AC010635.5 | 5 | 6.2 |
| RP11-58A5 | 5 | 7.1 |
| RP11-72C10 | 5 | 8.2 |
| RP11-79G1 | 5 | 8.6 |
| RP11-145B1 | 5 | 9.6 |
| RP11-91M12 | 5 | 10.3 |

TABLE 2-continued

| clone_id | chromosome | linear |
|---|---|---|
| RP11-91E7 | 5 | 11.1 |
| RP11-91M19 | 5 | 12 |
| RP11-88L18 | 5 | 13.7 |
| RP11-81P9 | 5 | 14.7 |
| RP11-135M13 | 5 | 16.4 |
| AC018409.3 | 5 | 17.5 |
| RP11-260E18 | 5 | 19.4 |
| RP11-91E20 | 5 | 21.8 |
| RP11-91L13 | 5 | 21.9 |
| RP11-90G17 | 5 | 22.9 |
| RP11-5N11 | 5 | 26.2 |
| RP11-422J14 | 5 | 26.5 |
| RP11-89M18 | 5 | 27.5 |
| RP11-81B23 | 5 | 28 |
| RP11-79I8 | 5 | 30.4 |
| RP11-80D4 | 5 | 31.2 |
| AC025447.4 | 5 | 32.9 |
| RP11-67N10 | 5 | 33.6 |
| RP11-90P7 | 5 | 35.8 |
| AC008830.4 | 5 | 39.6 |
| RP11-91I22 | 5 | 42.6 |
| RP11-79E13 | 5 | 44.1 |
| RP11-91M6 | 5 | 45.4 |
| RP11-19F12 | 5 | 45.6 |
| AC027339.3 | 5 | 48.4 |
| RP11-551B22 | 5 | 49.1 |
| RP11-17H13 | 5 | 52.4 |
| RP11-143O12 | 5 | 53.9 |
| AC034244.6 | 5 | 54.6 |
| AC016635.8 | 5 | 60.2 |
| RP11-19I19 | 5 | 61.7 |
| RP11-79C4 | 5 | 63.5 |
| RP11-89N5 | 5 | 63.5 |
| RP11-79C20 | 5 | 65.7 |
| RP11-480H11 | 5 | 66 |
| RP11-91C10 | 5 | 68.1 |
| RP11-88J2 | 5 | 70.1 |
| RP11-91M11 | 5 | 71.4 |
| RP11-91E18 | 5 | 71.5 |
| RP11-79I10 | 5 | 73.9 |
| RP11-90A9 | 5 | 78.7 |
| RP11-90M19 | 5 | 80.3 |
| RP11-80D2 | 5 | 82.6 |
| RP11-275E14 | 5 | 83.2 |
| RP11-258M21 | 5 | 85 |
| RP11-90J17 | 5 | 86.1 |
| AC005406.2 | 5 | 89.9 |
| AC104125.1 | 5 | 90.3 |
| RP11-88D22 | 5 | 94.3 |
| RP11-89C2 | 5 | 99.6 |
| RP11-115L24 | 5 | 101.1 |
| RP11-277N18 | 5 | 103.3 |
| RP11-252I13 | 5 | 103.7 |
| RP11-88L16 | 5 | 108.1 |
| RP11-89L24 | 5 | 110 |
| RP11-91G9 | 5 | 110.6 |
| RP11-64F17 | 5 | 111.4 |
| RP11-58G19 | 5 | 112.4 |
| RP11-81L23 | 5 | 113.8 |
| RP11-47L19 | 5 | 118.1 |
| RP11-81C5 | 5 | 120.5 |
| RP11-79K4 | 5 | 121.6 |
| RP11-90A15 | 5 | 123 |
| RP11-90G5 | 5 | 123.9 |
| RP11-265M23 | 5 | 124.7 |
| RP11-42M12 | 5 | 129 |
| AC004038.1 | 5 | 130.2 |
| AC005178.1 | 5 | 133.5 |
| RP11-21C10 | 5 | 134.5 |
| AC027305.4 | 5 | 134.8 |
| CTD-2004C12 | 5 | 137.5 |
| RP11-89G4 | 5 | 137.9 |
| AC008667.7 | 5 | 141.2 |
| RP11-115I4 | 5 | 142 |
| RP11-15J20 | 5 | 143 |
| RP11-55M16 | 5 | 143.1 |
| CTB-60P23 | 5 | 144.7 |
| RP11-124B12 | 5 | 149 |
| AC011352.4 | 5 | 149.8 |
| RP11-89F1 | 5 | 151.9 |
| RP11-79I6 | 5 | 153.9 |
| RP11-86C20 | 5 | 155 |
| RP11-91G17 | 5 | 156.3 |
| AC010603 | 5 | 158.2 |
| RP11-79I9 | 5 | 159.1 |
| RP11-89J5 | 5 | 159.9 |
| RP11-90N23 | 5 | 161.1 |
| RP11-31B18 | 5 | 164.8 |
| CTB-4E7 | 5 | 165.7 |
| RP11-134N14 | 5 | 166.7 |
| AC010254.5 | 5 | 167.1 |
| AC091921.1 | 5 | 169.7 |
| RP11-94L2 | 5 | 171 |
| RP11-13H20 | 5 | 172.6 |
| RP11-90C21 | 5 | 173.2 |
| AC011384.3 | 5 | 174.5 |
| RP11-14K9 | 5 | 175 |
| RP11-15F10 | 5 | 175.6 |
| AC011387.4 | 5 | 177.7 |
| RP11-626B22 | 5 | 182.4 |
| RP1-136B1 | 6 | 0.1 |
| AL035696.14 | 6 | 0.4 |
| RP11-91F13 | 6 | 1.7 |
| RP3-380B8 | 6 | 3.7 |
| RP1-80N2 | 6 | 4.3 |
| RP11-177C16 | 6 | 5.2 |
| RP3-470K1 | 6 | 6.2 |
| RP1-103M22 | 6 | 7.2 |
| RP3-416J7 | 6 | 7.9 |
| RP1-20B11 | 6 | 8.3 |
| RP11-79M24 | 6 | 9.4 |
| RP11-90P11 | 6 | 9.5 |
| RP11-91C13 | 6 | 10.5 |
| RP3-398A12 | 6 | 10.8 |
| RP11-421M1 | 6 | 11.6 |
| RP11-304M10 | 6 | 12.7 |
| RP3-441J1 | 6 | 13.7 |
| RP1-257A7 | 6 | 14.3 |
| RP11-90I11 | 6 | 15.4 |
| RP3-365E2 | 6 | 15.5 |
| RP1-147M19 | 6 | 16.7 |
| RP1-273P12 | 6 | 18.9 |
| RP11-90M17 | 6 | 19.3 |
| RP1-298J15 | 6 | 19.7 |
| RP1-209A6 | 6 | 21.3 |
| RP11-91H17 | 6 | 22.2 |
| RP3-369A17 | 6 | 22.9 |
| RP1-242N11 | 6 | 23.8 |
| RP1-130G2 | 6 | 25.2 |
| RP1-52M20 | 6 | 26.3 |
| RP1-224B21 | 6 | 27.8 |
| AL0201917.3 | 6 | 28.8 |
| RP5-874C20 | 6 | 30.6 |
| RP11-88D2 | 6 | 30.8 |
| RP5-974I11 | 6 | 31.6 |
| RP3-377H14 | 6 | 32.1 |
| RP11-79J17 | 6 | 35.2 |
| RP11-79J23 | 6 | 37.1 |
| RP3-329A5 | 6 | 37.5 |
| RP3-524E15 | 6 | 38.4 |
| RP1-50J22 | 6 | 38.6 |
| RP11-91E11 | 6 | 39.7 |
| RP3-460D19 | 6 | 40.7 |
| RP11-505E17 | 6 | 42.1 |
| RP11-81F7 | 6 | 43.9 |
| RP11-79I2 | 6 | 44.3 |
| RP5-973N23 | 6 | 45.9 |
| RP11-121G20 | 6 | 47.1 |
| RP3-449H6 | 6 | 47.4 |
| RP1-244F24 | 6 | 48.3 |
| RP3-447E21 | 6 | 48.9 |
| RP11-90H17 | 6 | 49.3 |
| RP1-306F2 | 6 | 51.1 |
| RP11-79F13 | 6 | 52 |

TABLE 2-continued

| clone_id | chromosome | linear |
|---|---|---|
| RP4-753D5 | 6 | 53.7 |
| RP3-357H1 | 6 | 54.7 |
| RP11-90K15 | 6 | 55.2 |
| RP1-27K12 | 6 | 56.3 |
| RP11-7H16 | 6 | 56.4 |
| RP11-146B10 | 6 | 58.5 |
| RP11-79O24 | 6 | 59.2 |
| RP3-496N17 | 6 | 60.4 |
| RP1-271N20 | 6 | 65.5 |
| AL133459.9 | 6 | 66 |
| RP11-448N11 | 6 | 66.6 |
| RP11-79F21 | 6 | 67.7 |
| RP11-88N6 | 6 | 68.1 |
| RP3-442I1 | 6 | 68.4 |
| RP5-819L10 | 6 | 69.5 |
| RP1-129L7 | 6 | 70.1 |
| RP11-80L16 | 6 | 70.4 |
| RP1-304O5 | 6 | 71.6 |
| RP1-46B1 | 6 | 73.3 |
| RP3-376F14 | 6 | 74.8 |
| RP1-104A17 | 6 | 75.5 |
| RP11-90G9 | 6 | 76.4 |
| RP5-1046G13 | 6 | 76.9 |
| RP11-374I18 | 6 | 77.6 |
| RP11-28P18 | 6 | 79 |
| RP1-238D15 | 6 | 79.8 |
| RP1-134M13 | 6 | 80.5 |
| RP11-343P23 | 6 | 81.9 |
| RP11-79L15 | 6 | 82.8 |
| RP1-136A11 | 6 | 83.4 |
| RP11-217L13 | 6 | 83.5 |
| RP1-232L24 | 6 | 84.6 |
| RP1-159G19 | 6 | 84.9 |
| RP1-279A18 | 6 | 85.5 |
| RP5-1046E21 | 6 | 86.1 |
| RP11-801I18 | 6 | 87.2 |
| AL049699.8 | 6 | 88.3 |
| RP4-676J13 | 6 | 89.1 |
| RP1-33L1 | 6 | 90 |
| RP11-43O2 | 6 | 91.5 |
| RP1-102H19 | 6 | 92.5 |
| RP3-486L4 | 6 | 93.2 |
| RP4-570O12 | 6 | 93.8 |
| RP1-131H7 | 6 | 94.8 |
| RP1-154G14 | 6 | 96 |
| RP3-433F14 | 6 | 97.2 |
| RP1-149C7 | 6 | 97.9 |
| RP11-538A16 | 6 | 98.5 |
| RP11-79F23 | 6 | 100 |
| RP1-104O17 | 6 | 101.6 |
| RP11-22L21 | 6 | 102.6 |
| RP3-453D15 | 6 | 103.9 |
| RP11-79G15 | 6 | 104.6 |
| RP1-121G13 | 6 | 105.8 |
| RP11-79K22 | 6 | 106.6 |
| RP11-90O11 | 6 | 106.8 |
| RP11-79O12 | 6 | 107.1 |
| RP3-514B11 | 6 | 108.8 |
| RP11-284O5 | 6 | 109.8 |
| RP3-454N4 | 6 | 110.9 |
| RP3-429G5 | 6 | 113.6 |
| RP1-128O3 | 6 | 113.7 |
| RP1-70A9 | 6 | 115.1 |
| RP1-261K5 | 6 | 115.9 |
| RP3-487J7 | 6 | 117.1 |
| RP11-506B6 | 6 | 117.9 |
| RP11-91B17 | 6 | 118.7 |
| RP11-367G18 | 6 | 119.4 |
| RP1-124O9 | 6 | 120.2 |
| Z95329.1 | 6 | 120.5 |
| RP1-136O14 | 6 | 122.1 |
| RP1-94G16 | 6 | 123.5 |
| RP3-344F17 | 6 | 124.2 |
| RP1-193N13 | 6 | 125.3 |
| RP11-411H20 | 6 | 126 |
| RP1-224E15 | 6 | 126.6 |
| RP3-438G17 | 6 | 128 |
| RP3-425C14 | 6 | 128.7 |
| RP11-80B14 | 6 | 129.4 |
| RP3-329N18 | 6 | 129.9 |
| RP1-249H1 | 6 | 130.1 |
| RP11-138M12 | 6 | 131.5 |
| RP1-312L17 | 6 | 133.3 |
| RP3-480J14 | 6 | 134.1 |
| RP1-86D1 | 6 | 134.8 |
| RP1-69D17 | 6 | 136.2 |
| RP3-353O9 | 6 | 137.7 |
| RP1-215F14 | 6 | 138.7 |
| RP11-435E4 | 6 | 139.4 |
| RP11-368O13 | 6 | 140.4 |
| RP11-557H15 | 6 | 141.3 |
| RP1-38C16 | 6 | 142.4 |
| RP11-89G8 | 6 | 142.6 |
| RP11-91G15 | 6 | 143.7 |
| RP3-372K1 | 6 | 144.2 |
| RP11-133O15 | 6 | 145 |
| RP1-225E12 | 6 | 145.9 |
| RP5-899B16 | 6 | 147 |
| AL357080.13 | 6 | 148 |
| RP11-89A10 | 6 | 148.5 |
| RP3-468K18 | 6 | 150.9 |
| RP11-43G16 | 6 | 152.3 |
| RP11-545I5 | 6 | 153 |
| RP1-69B13 | 6 | 153.6 |
| RP3-434O8 | 6 | 155 |
| RP1-281H8 | 6 | 156.6 |
| RP1-12G14 | 6 | 156.7 |
| RP11-291C6 | 6 | 157.7 |
| RP3-358E10 | 6 | 159.9 |
| RP11-535A9 | 6 | 160.4 |
| RP1-278N12 | 6 | 161.6 |
| RP1-257I9 | 6 | 162.7 |
| RP11-91I3 | 6 | 164.4 |
| RP11-266C7 | 6 | 165.3 |
| RP11-88B24 | 6 | 166.4 |
| RP3-393E18 | 6 | 166.9 |
| RP3-428L16 | 6 | 168.3 |
| RP11-81H13 | 6 | 168.4 |
| RP1-119H20 | 6 | 169.1 |
| RP1-51J12 | 6 | 171 |
| RP11-104N13 | 6 | 172.2 |
| RP3-345E4 | 6 | 173.5 |
| RP1-167A14 | 6 | 174.6 |
| RP1-125N5 | 6 | 175.9 |
| RP11-351J23 | 6 | 176.7 |
| RP1-182D15 | 6 | 177.5 |
| RP1-140C12 | 6 | 178.1 |
| AC073957.7 | 7 | 0.7 |
| RP11-90J23 | 7 | 3.8 |
| RP11-42B7 | 7 | 3.9 |
| RP11-2K20 | 7 | 4.7 |
| RP11-161C7 | 7 | 6.1 |
| RP11-79G16 | 7 | 7.6 |
| RP11-79O21 | 7 | 9.3 |
| RP11-451C12 | 7 | 10.9 |
| RP11-89B15 | 7 | 15.1 |
| RP11-123E5 | 7 | 17.1 |
| RP11-70K3 | 7 | 17.8 |
| RP11-91A24 | 7 | 19.4 |
| CTB-23M10 | 7 | 21.1 |
| RP11-79G17 | 7 | 21.5 |
| RP11-79D17 | 7 | 22.8 |
| CTB-119H12 | 7 | 23.6 |
| AC010677.4 | 7 | 27.1 |
| RP11-81F15 | 7 | 28 |
| RP11-88B20 | 7 | 29 |
| RP11-80J6 | 7 | 29.9 |
| RP11-242I4 | 7 | 30.5 |
| RP11-90J13 | 7 | 32.1 |
| AC018648.5 | 7 | 33 |
| RP11-89N17 | 7 | 34 |
| RP11-115G23 | 7 | 35.4 |
| AC083876.2 | 7 | 36.7 |
| RP11-75O22 | 7 | 37.5 |

TABLE 2-continued

| clone_id | chromosome | linear |
|---|---|---|
| RP11-115G1 | 7 | 39 |
| RP11-64I2 | 7 | 40 |
| RP11-112L4 | 7 | 40.1 |
| AC005027.2 | 7 | 42.3 |
| RP11-100C21 | 7 | 43.3 |
| RP11-449D13 | 7 | 44.2 |
| RP11-52M17 | 7 | 45.2 |
| RP11-109N2 | 7 | 46.9 |
| AC073341.9 | 7 | 48.1 |
| RP11-11D14 | 7 | 48.4 |
| RP11-15L23 | 7 | 51.8 |
| RP11-91C9 | 7 | 53.2 |
| RP11-90N11 | 7 | 54.6 |
| AC073347.3 | 7 | 56.5 |
| RP11-90O18 | 7 | 61 |
| RP11-45N18 | 7 | 61.9 |
| RP11-35P20 | 7 | 65.5 |
| AC006319.3 | 7 | 66 |
| RP11-41F23 | 7 | 67.7 |
| RP11-89D15 | 7 | 67.8 |
| RP11-88H20 | 7 | 68.5 |
| RP11-114E12 | 7 | 69.2 |
| RP11-90B1 | 7 | 69.6 |
| RP11-137E8 | 7 | 72.5 |
| RP11-89A20 | 7 | 74.8 |
| RP11-451M14 | 7 | 75.5 |
| RP11-88H22 | 7 | 76.8 |
| RP11-60N2 | 7 | 78 |
| RP11-91E1 | 7 | 78.4 |
| RP11-89L18 | 7 | 78.9 |
| AC005064.3 | 7 | 80.5 |
| RP11-90N9 | 7 | 83.2 |
| RP11-22M18 | 7 | 84.7 |
| RP11-88D24 | 7 | 85 |
| RP11-46O13 | 7 | 87.7 |
| AC000059.1 | 7 | 89.6 |
| RP11-90H9 | 7 | 91.8 |
| RP11-79O7 | 7 | 93.2 |
| RP11-91M13 | 7 | 93.8 |
| RP11-10D8 | 7 | 99.1 |
| RP11-80P24 | 7 | 99.4 |
| RP11-72J24 | 7 | 105 |
| RP11-80L6 | 7 | 106.9 |
| RP11-89M2 | 7 | 107.6 |
| RP11-77E2 | 7 | 108.5 |
| AC002487.1 | 7 | 109.2 |
| RP11-12L9 | 7 | 112.3 |
| CTB-22K14 | 7 | 113.2 |
| RP11-90N13 | 7 | 113.4 |
| RP11-88J20 | 7 | 114.3 |
| RP11-89O20 | 7 | 115.1 |
| RP11-78C11 | 7 | 116.5 |
| RP11-110C11 | 7 | 117.5 |
| RP11-51M22 | 7 | 117.9 |
| CTB-133K23 | 7 | 119.2 |
| RP11-140O21 | 7 | 122.6 |
| RP11-3L10 | 7 | 123 |
| RP11-112P4 | 7 | 123.6 |
| RP11-81B7 | 7 | 129.3 |
| RP11-80N8 | 7 | 129.9 |
| RP11-66F23 | 7 | 131.3 |
| RP11-35B6 | 7 | 131.9 |
| AC007938.1 | 7 | 132.8 |
| RP11-79E7 | 7 | 136.5 |
| RP11-140I14 | 7 | 137.7 |
| RP11-88K4 | 7 | 139.5 |
| RP11-80J18 | 7 | 140.1 |
| RP11-137O4 | 7 | 141 |
| AC083883.6 | 7 | 141.6 |
| AC004853.1 | 7 | 147.4 |
| RP11-79M8 | 7 | 148.1 |
| RP11-79K23 | 7 | 151 |
| RP11-89P11 | 7 | 151.3 |
| RP11-91P1 | 7 | 152.3 |
| RP11-43L19 | 7 | 155.6 |
| RP11-79K9 | 7 | 157.4 |
| RP11-80J22 | 7 | 157.8 |

TABLE 2-continued

| clone_id | chromosome | linear |
|---|---|---|
| RP11-58F7 | 7 | 160.8 |
| RP11-91J19 | 8 | 0.2 |
| AF188030.3 | 8 | 1.5 |
| RP11-11P7 | 8 | 2.7 |
| RP11-121F7 | 8 | 3.3 |
| RP11-45M12 | 8 | 4 |
| RP11-89I12 | 8 | 4.6 |
| RP11-1K11 | 8 | 4.8 |
| RP11-90J21 | 8 | 7.4 |
| RP11-79E11 | 8 | 7.8 |
| RP11-79I19 | 8 | 9.3 |
| RP11-252K12 | 8 | 11.5 |
| RP11-80B8 | 8 | 11.6 |
| RP11-90O17 | 8 | 12.9 |
| RP11-23H1 | 8 | 15.5 |
| AC010656.7 | 8 | 16 |
| RP11-90I3 | 8 | 17.1 |
| RP11-89M16 | 8 | 17.8 |
| RP11-51C1 | 8 | 20 |
| RP11-89O4 | 8 | 21.5 |
| RP11-110I16 | 8 | 22.3 |
| RP11-89M8 | 8 | 23.6 |
| RP11-76B12 | 8 | 25.7 |
| RP11-90M13 | 8 | 26.7 |
| RP11-70L1 | 8 | 27.7 |
| RP11-138J2 | 8 | 28.4 |
| RP11-116F9 | 8 | 29.3 |
| RP11-662B19 | 8 | 29.8 |
| RP11-279J6 | 8 | 30.9 |
| RP11-173D10 | 8 | 31.9 |
| RP11-139G9 | 8 | 32.2 |
| RP11-57I3 | 8 | 33.7 |
| RP11-2I13 | 8 | 34.6 |
| RP11-91P13 | 8 | 34.9 |
| RP11-79H13 | 8 | 36.1 |
| RP11-237M13 | 8 | 37.4 |
| RP11-89M20 | 8 | 37.8 |
| RP11-113G10 | 8 | 39.4 |
| RP11-90P5 | 8 | 39.5 |
| RP11-262I23 | 8 | 40.5 |
| AC015649.6 | 8 | 42.2 |
| RP11-89A4 | 8 | 43.3 |
| RP11-12L15 | 8 | 46 |
| RP11-113H14 | 8 | 47.9 |
| RP11-10H3 | 8 | 49 |
| RP11-11C20 | 8 | 51.6 |
| AC090814.2 | 8 | 52.7 |
| RP11-105K5 | 8 | 53.4 |
| RP11-767C6 | 8 | 54 |
| RP11-99M6 | 8 | 54.5 |
| RP11-172D2 | 8 | 54.7 |
| AC046176.7 | 8 | 55.9 |
| RP11-16M8 | 8 | 56.2 |
| AC021393.5 | 8 | 58.4 |
| RP11-91I20 | 8 | 58.8 |
| RP11-24L2 | 8 | 60.2 |
| AC019357.5 | 8 | 61.5 |
| AC023533.6 | 8 | 62.5 |
| RP11-89A16 | 8 | 63.2 |
| AC087768.3 | 8 | 64.3 |
| RP11-79G22 | 8 | 67.5 |
| RP11-11K9 | 8 | 69.9 |
| RP11-114M5 | 8 | 71.2 |
| RP11-148M7 | 8 | 73.2 |
| RP11-359N14 | 8 | 73.7 |
| RP11-117N14 | 8 | 74.3 |
| RP11-88N8 | 8 | 75.1 |
| RP11-65J24 | 8 | 76.3 |
| RP11-89H1 | 8 | 77.4 |
| RP11-80F24 | 8 | 78.3 |
| RP11-90B7 | 8 | 79.1 |
| RP11-15K1 | 8 | 79.9 |
| RP11-89I14 | 8 | 80.5 |
| RP11-93E11 | 8 | 81.6 |
| RP11-257P3 | 8 | 82.2 |
| RP11-90F1 | 8 | 85.5 |
| RP11-90O15 | 8 | 85.7 |

TABLE 2-continued

| clone_id | chromosome | linear |
|---|---|---|
| RP11-96G1 | 8 | 86.5 |
| RP11-91K2 | 8 | 87 |
| RP11-80P18 | 8 | 87.7 |
| RP11-90G19 | 8 | 88.6 |
| RP11-88J22 | 8 | 89.6 |
| RP11-88J8 | 8 | 91 |
| RP11-89F14 | 8 | 91.9 |
| RP11-27I15 | 8 | 94.1 |
| RP11-90N3 | 8 | 95.2 |
| RP11-80P10 | 8 | 96.1 |
| RP11-90D11 | 8 | 98.8 |
| RP11-30J11 | 8 | 100 |
| RP11-91O11 | 8 | 102.2 |
| RP11-79F7 | 8 | 107 |
| RP11-79J9 | 8 | 108 |
| RP11-81B5 | 8 | 109.2 |
| RP11-80D8 | 8 | 109.8 |
| RP11-79C21 | 8 | 109.9 |
| RP11-91K1 | 8 | 110.8 |
| RP11-79C18 | 8 | 111.2 |
| RP11-3A12 | 8 | 113.6 |
| RP11-89I16 | 8 | 115.3 |
| RP11-30P9 | 8 | 119 |
| RP11-89P19 | 8 | 119.5 |
| RP11-88J18 | 8 | 121.8 |
| AC037486.2 | 8 | 122.6 |
| RP11-89P9 | 8 | 125.8 |
| RP11-91M23 | 8 | 127.3 |
| RP11-65D17 | 8 | 127.7 |
| RP11-89K10 | 8 | 128.1 |
| RP11-79E8 | 8 | 131.1 |
| RP11-94M13 | 8 | 133.3 |
| RP11-184M21 | 8 | 134.7 |
| AF186190.3 | 8 | 135.1 |
| RP11-45B19 | 8 | 135.9 |
| RP11-21H16 | 8 | 136.2 |
| RP11-17M8 | 8 | 137.9 |
| RP11-449D3 | 8 | 138.2 |
| RP11-489O18 | 8 | 139.1 |
| RP11-13A18 | 8 | 141.7 |
| RP11-642A1 | 8 | 141.7 |
| RP11-349C2 | 8 | 144.7 |
| RP5-1124C13 | 8 | 145.2 |
| RP11-31M2 | 9 | 0.7 |
| AL136231.12 | 9 | 1.2 |
| RP11-140C18 | 9 | 1.9 |
| RP11-207C16 | 9 | 2.4 |
| RP11-79M14 | 9 | 3 |
| RP11-79K3 | 9 | 4.3 |
| RP11-376O21 | 9 | 5 |
| RP11-91E3 | 9 | 6.5 |
| RP11-32D4 | 9 | 8.5 |
| RP11-130C19 | 9 | 10.6 |
| RP11-88P16 | 9 | 11.6 |
| RP11-125B21 | 9 | 12.3 |
| RP11-32F11 | 9 | 13.1 |
| RP11-328C23 | 9 | 14.1 |
| RP11-382H24 | 9 | 14.6 |
| RP11-79B9 | 9 | 15.7 |
| RP11-490C5 | 9 | 16.8 |
| RP11-109M15 | 9 | 17.8 |
| RP11-340N12 | 9 | 18.9 |
| RP11-163F8 | 9 | 19.3 |
| RP11-81B11 | 9 | 20.5 |
| RP11-87O1 | 9 | 20.7 |
| RP11-399M15 | 9 | 21.1 |
| RP11-89C6 | 9 | 21.7 |
| RP11-408N14 | 9 | 24.2 |
| AL391117.7 | 9 | 24.9 |
| RP11-332M12 | 9 | 26.9 |
| AL139235 | 9 | 27.1 |
| RP11-381K22 | 9 | 28.4 |
| RP11-57P14 | 9 | 29.2 |
| RP11-64M21 | 9 | 30.1 |
| RP11-159L16 | 9 | 31.5 |
| RP11-29M23 | 9 | 32.1 |
| RP11-630H9 | 9 | 32.6 |
| RP11-70F16 | 9 | 33.3 |
| RP11-52I10 | 9 | 34 |
| RP11-79E21 | 9 | 34.4 |
| RP11-54K16 | 9 | 35.3 |
| RP11-395N21 | 9 | 37.6 |
| RP11-327L3 | 9 | 38.2 |
| RP11-12P15 | 9 | 39 |
| RP11-203L2 | 9 | 59.2 |
| RP11-16N10 | 9 | 59.7 |
| RP11-129O15 | 9 | 60.8 |
| RP11-89K20 | 9 | 61.2 |
| RP11-63P12 | 9 | 62.8 |
| RP11-54O21 | 9 | 63.6 |
| RP11-174B4 | 9 | 65.5 |
| RP11-323A7 | 9 | 66.5 |
| RP11-158I5 | 9 | 67.5 |
| AL445684 | 9 | 69.1 |
| RP11-79G7 | 9 | 70.7 |
| RP11-91M2 | 9 | 71.6 |
| RP11-79J13 | 9 | 72.7 |
| RP11-22C13 | 9 | 73.7 |
| RP11-80F16 | 9 | 73.7 |
| RP11-80H20 | 9 | 74.9 |
| RP11-65C15 | 9 | 76.9 |
| RP11-79I21 | 9 | 77.7 |
| RP11-65B23 | 9 | 78.7 |
| RP11-88J16 | 9 | 79.6 |
| RP11-406A20 | 9 | 80.4 |
| RP11-563G12 | 9 | 81 |
| RP11-95G21 | 9 | 81.5 |
| RP11-89K14 | 9 | 82.1 |
| RP11-62C3 | 9 | 83.4 |
| RP11-19J3 | 9 | 83.8 |
| RP11-30L4 | 9 | 84.8 |
| RP11-173G21 | 9 | 87.1 |
| RP11-89L5 | 9 | 88 |
| RP11-80J10 | 9 | 88.2 |
| RP11-79A20 | 9 | 88.3 |
| RP11-23B15 | 9 | 89.2 |
| RP11-69F21 | 9 | 90.7 |
| AL356798.17 | 9 | 91.9 |
| RP11-80H12 | 9 | 92.7 |
| RP11-91L19 | 9 | 94.2 |
| RP11-318L4 | 9 | 95.4 |
| RP11-217O12 | 9 | 96.4 |
| RP11-80N14 | 9 | 96.9 |
| RP11-80F13 | 9 | 99.6 |
| RP11-505C13 | 9 | 100.4 |
| RP11-115J22 | 9 | 101.3 |
| RP11-81P13 | 9 | 102.6 |
| RP11-104M22 | 9 | 103.2 |
| RP11-4O1 | 9 | 104.4 |
| RP11-408O19 | 9 | 105.4 |
| RP11-9H12 | 9 | 105.7 |
| RP11-88F16 | 9 | 107.5 |
| RP11-45A16 | 9 | 109 |
| RP11-451E16 | 9 | 111 |
| RP11-98E22 | 9 | 111.5 |
| RP11-57K1 | 9 | 112.4 |
| RP11-342H3 | 9 | 114 |
| RP11-297L11 | 9 | 114.7 |
| RP11-74E13 | 9 | 115.7 |
| RP11-142K22 | 9 | 115.8 |
| RP11-116C10 | 9 | 117.2 |
| RP11-91G7 | 9 | 117.9 |
| RP11-282P20 | 9 | 118.8 |
| RP11-1M19 | 9 | 119.8 |
| RP11-339B21 | 9 | 121.1 |
| RP11-98H23 | 9 | 121.8 |
| RP11-17O4 | 9 | 122.5 |
| RP11-89P10 | 9 | 123.4 |
| RP11-81P5 | 9 | 125.3 |
| RP11-326L24 | 9 | 126 |
| RP11-153P4 | 9 | 127.1 |
| AL354671.10 | 9 | 127.7 |
| RP11-92B21 | 9 | 128.5 |
| RP11-145E17 | 9 | 129.3 |

TABLE 2-continued

| clone_id | chromosome | linear |
|---|---|---|
| RP11-100C15 | 9 | 129.8 |
| RP11-417A4 | 9 | 131.3 |
| AL590627.18 | 9 | 132.2 |
| RP11-10D13 | 10 | 0.2 |
| RP11-164C1 | 10 | 0.7 |
| RP11-809C18 | 10 | 0.7 |
| RP11-38M7 | 10 | 0.9 |
| RP11-90D7 | 10 | 1 |
| RP11-89B19 | 10 | 1.2 |
| RP11-74N14 | 10 | 1.7 |
| RP11-80D10 | 10 | 2.6 |
| RP11-118K6 | 10 | 3.1 |
| RP11-89J3 | 10 | 4.5 |
| RP11-90M21 | 10 | 7 |
| RP11-79C22 | 10 | 7.6 |
| RP11-42I17 | 10 | 8.6 |
| RP11-91K20 | 10 | 8.8 |
| AL136319.8 | 10 | 11.2 |
| RP11-89C21 | 10 | 12.1 |
| RP11-796C22 | 10 | 13.5 |
| RP11-24J20 | 10 | 13.8 |
| AL157392.11 | 10 | 14.2 |
| RP11-22K18 | 10 | 15.1 |
| RP11-271M1 | 10 | 15.7 |
| RP11-149I8 | 10 | 16.3 |
| RP11-394I23 | 10 | 16.7 |
| RP11-337F21 | 10 | 17.8 |
| RP11-576H16 | 10 | 18.8 |
| RP11-91D9 | 10 | 19.3 |
| RP11-60J16 | 10 | 20.5 |
| RP11-108B14 | 10 | 22.6 |
| RP11-89J6 | 10 | 23.4 |
| RP11-90F7 | 10 | 23.6 |
| RP11-176P2 | 10 | 24.9 |
| RP11-80K21 | 10 | 26 |
| RP11-79D7 | 10 | 27.5 |
| RP11-91A23 | 10 | 28.7 |
| RP11-89I20 | 10 | 29.4 |
| RP11-89D1 | 10 | 30 |
| RP11-15H10 | 10 | 30.6 |
| RP11-125C10 | 10 | 33.1 |
| RP11-33I16 | 10 | 33.4 |
| RP11-79K19 | 10 | 34.5 |
| RP11-174P15 | 10 | 35.9 |
| RP11-365P10 | 10 | 37.1 |
| RP11-155G16 | 10 | 37.3 |
| RP11-393J16 | 10 | 38.4 |
| RP11-109N22 | 10 | 39.4 |
| RP11-22B24 | 10 | 41 |
| RP11-80J20 | 10 | 41.2 |
| RP11-48O11 | 10 | 43.9 |
| RP11-20J15 | 10 | 44.6 |
| RP11-42B19 | 10 | 47.4 |
| AL390716.26 | 10 | 49.1 |
| RP11-71N21 | 10 | 49.7 |
| RP11-27P22 | 10 | 50.3 |
| RP11-92I18 | 10 | 51.4 |
| RP11-75M12 | 10 | 52.3 |
| RP11-133C15 | 10 | 53 |
| RP11-319F12 | 10 | 53.9 |
| RP11-449J3 | 10 | 55.1 |
| RP11-394D15 | 10 | 55.5 |
| RP11-88B18 | 10 | 56.6 |
| RP11-373P23 | 10 | 59 |
| RP11-79A2 | 10 | 61.1 |
| RP11-91H19 | 10 | 62.3 |
| RP11-166B18 | 10 | 63.4 |
| RP11-267O2 | 10 | 64.3 |
| RP11-90E17 | 10 | 65.5 |
| RP11-351O1 | 10 | 66.5 |
| RP11-428G2 | 10 | 68.4 |
| RP11-344A5 | 10 | 70.2 |
| RP11-474D14 | 10 | 71.2 |
| RP11-86K9 | 10 | 71.9 |
| RP11-135E4 | 10 | 72.3 |
| RP11-6P16 | 10 | 73 |
| RP11-52K17 | 10 | 73.4 |

TABLE 2-continued

| clone_id | chromosome | linear |
|---|---|---|
| RP11-91A1 | 10 | 74.2 |
| RP11-472K8 | 10 | 75.8 |
| RP11-354E23 | 10 | 76.9 |
| RP11-390A15 | 10 | 78 |
| RP11-90D9 | 10 | 79 |
| RP11-89A18 | 10 | 79.3 |
| RP11-399K21 | 10 | 79.8 |
| RP11-79M9 | 10 | 80.8 |
| RP11-19C18 | 10 | 81.8 |
| RP11-157J13 | 10 | 82.8 |
| RP11-90J7 | 10 | 83.5 |
| RP11-93O23 | 10 | 85.4 |
| RP11-175M21 | 10 | 86.4 |
| RP11-315E23 | 10 | 87.1 |
| RP11-185K11 | 10 | 87.8 |
| RP11-124L5 | 10 | 88.9 |
| RP11-90O7 | 10 | 90.3 |
| RP11-52G13 | 10 | 91.7 |
| RP11-57C13 | 10 | 92.2 |
| RP11-79A15 | 10 | 92.7 |
| RP11-129G17 | 10 | 93.3 |
| AL157394.14 | 10 | 94 |
| RP11-248C1 | 10 | 94.9 |
| RP11-152G7 | 10 | 96.5 |
| AC079844.3 | 10 | 96.6 |
| RP11-366I13 | 10 | 97.8 |
| RP11-91M16 | 10 | 99.7 |
| RP11-80J24 | 10 | 99.8 |
| RP11-90J1 | 10 | 100.1 |
| RP11-79M5 | 10 | 101.1 |
| RP11-90O1 | 10 | 102 |
| RP11-123G19 | 10 | 103.4 |
| CTD-2022D20 | 10 | 104.6 |
| RP11-483F11 | 10 | 105.8 |
| RP11-316M21 | 10 | 106.3 |
| RP11-108L7 | 10 | 107.2 |
| RP11-68M5 | 10 | 107.9 |
| RP11-89G15 | 10 | 108.5 |
| RP11-416N2 | 10 | 110.3 |
| RP11-541N10 | 10 | 110.5 |
| RP11-202C2 | 10 | 111.8 |
| RP11-89G20 | 10 | 112.8 |
| RP11-432B10 | 10 | 114.1 |
| RP11-626C11 | 10 | 115.1 |
| RP11-90K19 | 10 | 115.9 |
| RP11-469M11 | 10 | 117.3 |
| RP11-271I13 | 10 | 118 |
| RP11-431P18 | 10 | 119.9 |
| RP11-89C18 | 10 | 120.2 |
| RP11-106N20 | 10 | 121.5 |
| RP11-89H7 | 10 | 123 |
| RP11-96N16 | 10 | 124.7 |
| CTB-54O2 | 10 | 125.6 |
| RP11-140G2 | 10 | 126.2 |
| RP11-354M20 | 10 | 126.7 |
| RP11-51G15 | 10 | 127.6 |
| RP11-79M19 | 10 | 128 |
| RP11-140B17 | 10 | 129 |
| RP11-95I16 | 10 | 129.8 |
| RP11-500G22 | 10 | 130.9 |
| RP11-101I20 | 10 | 131.9 |
| RP11-8O10 | 10 | 133.1 |
| RP11-16P8 | 10 | 133.9 |
| RP11-42K2 | 10 | 135.3 |
| RP11-88B12 | 10 | 135.7 |
| RP11-48A2 | 10 | 135.9 |
| RP11-90O13 | 10 | 137.6 |
| RP11-122K13 | 10 | 138.1 |
| RP11-408L20 | 10 | 139.2 |
| RP11-142I8 | 10 | 139.6 |
| AL392043.10 | 10 | 140.6 |
| RP11-288G11 | 10 | 141.2 |
| RP11-90B19 | 10 | 141.4 |
| RP11-108K14 | 10 | 141.8 |
| RP11-371C18 | 11 | 1.5 |
| RP11-89O6 | 11 | 5.8 |
| RP11-21N2 | 11 | 7 |

TABLE 2-continued

| clone_id | chromosome | linear |
|---|---|---|
| RP11-79E12 | 11 | 9.4 |
| RP11-170F20 | 11 | 9.9 |
| RP11-206L19 | 11 | 10.9 |
| RP11-98J9 | 11 | 12.5 |
| RP11-21L19 | 11 | 13.1 |
| RP11-7O20 | 11 | 13.8 |
| RP11-89P13 | 11 | 14.6 |
| RP11-166E15 | 11 | 16 |
| RP11-108J18 | 11 | 16.9 |
| RP11-81D23 | 11 | 17.2 |
| RP11-80B10 | 11 | 18.3 |
| RP11-11A11 | 11 | 19 |
| AC016904.4 | 11 | 21.4 |
| AC009638.4 | 11 | 24.4 |
| RP11-16H3 | 11 | 26 |
| RP11-79M22 | 11 | 26.8 |
| RP11-79E9 | 11 | 29.1 |
| RP5-859D17 | 11 | 29.6 |
| RP1-296L11 | 11 | 31 |
| AC027548 | 11 | 31.8 |
| RP1-187A11 | 11 | 33.2 |
| RP11-90F13 | 11 | 33.9 |
| RP1-22J9 | 11 | 34.1 |
| RP11-91G22 | 11 | 35.6 |
| AC026970.4 | 11 | 36.1 |
| RP1-72A10 | 11 | 36.6 |
| RP11-219O3 | 11 | 37.2 |
| RP11-36H11 | 11 | 37.9 |
| RP11-89G12 | 11 | 39.3 |
| AC013488.6 | 11 | 40.9 |
| RP11-220C23 | 11 | 41.4 |
| RP11-150D18 | 11 | 42.4 |
| RP11-79O11 | 11 | 44 |
| RP11-12C11 | 11 | 45.6 |
| AP002509.1 | 11 | 48.3 |
| RP11-79A4 | 11 | 48.6 |
| RP11-56E13 | 11 | 51.5 |
| RP11-77M17 | 11 | 53.9 |
| RP11-135H8 | 11 | 54.6 |
| AC090309.4 | 11 | 57.6 |
| RP11-205I14 | 11 | 59.1 |
| RP11-729B4 | 11 | 59.4 |
| RP11-5F17 | 11 | 61 |
| RP11-49D19 | 11 | 62.4 |
| RP11-15L8 | 11 | 64.3 |
| RP11-607L20 | 11 | 64.4 |
| RP11-203N8 | 11 | 67.7 |
| AP000405.3 | 11 | 68 |
| RP11-20K4 | 11 | 68.8 |
| RP11-730K20 | 11 | 69.7 |
| RP11-80B24 | 11 | 71.2 |
| RP11-8D13 | 11 | 71.4 |
| RP11-44J5 | 11 | 72.7 |
| RP11-548G17 | 11 | 73.6 |
| RP11-115O9 | 11 | 74.5 |
| RP11-168B13 | 11 | 75.6 |
| RP11-102M18 | 11 | 77.4 |
| RP11-91P18 | 11 | 78.2 |
| RP11-483P13 | 11 | 78.6 |
| AP002343.1 | 11 | 79.3 |
| RP11-79B7 | 11 | 80.2 |
| RP11-7H7 | 11 | 81 |
| AP001557.3 | 11 | 82 |
| RP11-91A3 | 11 | 82.9 |
| RP11-1E8 | 11 | 84.7 |
| RP11-90K17 | 11 | 86.5 |
| RP11-89M14 | 11 | 87.2 |
| RP11-19P3 | 11 | 87.8 |
| RP11-80P16 | 11 | 88.7 |
| RP11-80F20 | 11 | 89.4 |
| RP11-876F8 | 11 | 91.2 |
| RP11-30C9 | 11 | 92.7 |
| RP11-372E19 | 11 | 94.7 |
| RP11-163O18 | 11 | 96.6 |
| RP11-91O4 | 11 | 96.9 |
| RP11-16K5 | 11 | 99.1 |
| RP11-267L1 | 11 | 101.3 |

TABLE 2-continued

| clone_id | chromosome | linear |
|---|---|---|
| RP11-775E2 | 11 | 103.8 |
| RP11-88H18 | 11 | 106.4 |
| RP11-33F6 | 11 | 106.6 |
| RP11-179B7 | 11 | 108.1 |
| RP11-51M23 | 11 | 108.6 |
| RP11-648J7 | 11 | 109.9 |
| AP003057.1 | 11 | 110.9 |
| RP11-56J3 | 11 | 112.4 |
| RP11-209E9 | 11 | 112.6 |
| RP11-2F21 | 11 | 114.1 |
| RP11-89O8 | 11 | 114.4 |
| RP11-163A13 | 11 | 116.1 |
| RP11-79I17 | 11 | 117.6 |
| AP003463.1 | 11 | 119.5 |
| RP11-356E17 | 11 | 121.2 |
| RP11-35P15 | 11 | 122.2 |
| RP11-45N4 | 11 | 123.2 |
| RP11-112I9 | 11 | 123.7 |
| RP11-62A14 | 11 | 124.6 |
| RP11-89H13 | 11 | 125.6 |
| RP11-89P5 | 11 | 126.2 |
| RP11-344F5 | 11 | 127.5 |
| RP11-164B14 | 11 | 128.1 |
| RP11-87O12 | 11 | 129.2 |
| RP11-11C15 | 11 | 129.4 |
| RP11-164A10 | 11 | 130.2 |
| RP11-10N17 | 11 | 131.2 |
| RP11-50B3 | 11 | 132.4 |
| RP11-20M1 | 11 | 132.8 |
| RP11-41K5 | 11 | 133.2 |
| RP11-112M22 | 11 | 134.7 |
| AP003482.1 | 11 | 136 |
| AC023429 | 11 | 136.9 |
| RP11-354O3 | 11 | 137.6 |
| RP11-77C9 | 11 | 138.6 |
| RP11-17M17 | 11 | 139.6 |
| AP000903.5 | 11 | 139.7 |
| RP11-27H17 | 11 | 140.9 |
| RP11-469N6 | 11 | 141.4 |
| RP11-598F7 | 12 | 0.1 |
| RP11-283I3 | 12 | 0.2 |
| RP11-359B12 | 12 | 1 |
| RP11-79K20 | 12 | 1 |
| RP11-543P15 | 12 | 3.1 |
| RP11-88D16 | 12 | 3.3 |
| RP11-74M9 | 12 | 4.2 |
| RP11-388F6 | 12 | 4.4 |
| RP11-91B13 | 12 | 4.6 |
| RP11-319E16 | 12 | 5.2 |
| RP11-451H11 | 12 | 5.9 |
| RP11-433J6 | 12 | 6.7 |
| RP11-277E18 | 12 | 8.3 |
| RP11-13C13 | 12 | 10.2 |
| RP11-144O23 | 12 | 11.1 |
| RP11-434C1 | 12 | 12 |
| RP11-4N23 | 12 | 13.4 |
| RP11-59H1 | 12 | 13.8 |
| RP11-96K24 | 12 | 14.5 |
| RP11-502N13 | 12 | 15 |
| RP11-91B19 | 12 | 16.3 |
| RP11-1018J8 | 12 | 17.2 |
| AC087311.22 | 12 | 17.7 |
| RP11-871F6 | 12 | 18.7 |
| RP11-489N6 | 12 | 20.1 |
| RP11-206D16 | 12 | 21.3 |
| RP11-956A19 | 12 | 22.7 |
| RP11-460N10 | 12 | 23.4 |
| RP11-12D15 | 12 | 24.7 |
| RP11-80N2 | 12 | 25 |
| RP11-729I10 | 12 | 26.1 |
| RP11-90K13 | 12 | 28.3 |
| RP11-89L4 | 12 | 29.3 |
| RP11-64J22 | 12 | 30.1 |
| RP11-1060J15 | 12 | 31.7 |
| RP11-780A5 | 12 | 34 |
| RP11-100P18 | 12 | 34.3 |
| AC011324.22 | 12 | 35.6 |

TABLE 2-continued

| clone_id | chromosome | linear |
|---|---|---|
| RP11-56J24 | 12 | 36.6 |
| RP11-152M7 | 12 | 40.4 |
| RP11-91K15 | 12 | 42.3 |
| RP11-90I21 | 12 | 44.4 |
| RP11-624G19 | 12 | 45.6 |
| RP11-490D11 | 12 | 46.7 |
| RP11-139E19 | 12 | 46.9 |
| RP11-79K1 | 12 | 49.1 |
| RP11-89H19 | 12 | 49.5 |
| RP11-25K5 | 12 | 51.5 |
| RP11-91L17 | 12 | 53 |
| RP11-79O1 | 12 | 53.9 |
| RP11-97N16 | 12 | 55.1 |
| RP11-101H10 | 12 | 55.8 |
| RP11-972K6 | 12 | 56.5 |
| RP11-681G7 | 12 | 57.2 |
| RP11-548L8 | 12 | 57.9 |
| RP11-183H16 | 12 | 58.9 |
| RP11-91I15 | 12 | 59.3 |
| RP11-799O6 | 12 | 60.1 |
| RP11-39G24 | 12 | 60.8 |
| RP11-90P21 | 12 | 62.9 |
| RP11-35G5 | 12 | 63.4 |
| RP11-80D18 | 12 | 64.2 |
| RP11-88F24 | 12 | 64.2 |
| RP11-88F18 | 12 | 64.4 |
| RP11-91H3 | 12 | 64.5 |
| RP11-631N16 | 12 | 65.2 |
| RP11-196H14 | 12 | 66.2 |
| RP11-1022B3 | 12 | 66.4 |
| AC025603.1 | 12 | 68.8 |
| RP11-596J18 | 12 | 69.9 |
| RP11-91K23 | 12 | 71 |
| RP11-90G3 | 12 | 73.7 |
| RP11-89P15 | 12 | 75.3 |
| RP11-89M22 | 12 | 75.9 |
| RP11-92P22 | 12 | 77.2 |
| RP11-81H3 | 12 | 78.4 |
| RP11-96F19 | 12 | 81 |
| RP11-90C1 | 12 | 82.4 |
| RP11-530C5 | 12 | 83.8 |
| RP11-230I13 | 12 | 85.3 |
| RP11-362A1 | 12 | 86.1 |
| RP11-79B17 | 12 | 90.8 |
| RP11-88N10 | 12 | 91.4 |
| RP11-900F13 | 12 | 92.8 |
| AC083808.9 | 12 | 93.8 |
| RP11-89F16 | 12 | 94.9 |
| RP11-141N1 | 12 | 95.8 |
| AC073655.26 | 12 | 97.5 |
| RP11-282G15 | 12 | 98.4 |
| AC069263.8 | 12 | 99.5 |
| RP11-510I5 | 12 | 100.5 |
| RP11-79K8 | 12 | 102 |
| RP11-81D15 | 12 | 102.3 |
| RP11-90E9 | 12 | 102.8 |
| RP11-91M8 | 12 | 107.4 |
| RP11-443B14 | 12 | 109.4 |
| RP11-91M22 | 12 | 109.6 |
| RP11-110L13 | 12 | 111.2 |
| RP11-90N16 | 12 | 112 |
| RP11-81H23 | 12 | 112.4 |
| RP11-951I11 | 12 | 113.5 |
| RP11-91I24 | 12 | 114.3 |
| AC007570.23 | 12 | 115.3 |
| RP11-426H24 | 12 | 117.4 |
| RP11-90D13 | 12 | 118 |
| RP11-90F3 | 12 | 118.2 |
| RP11-100B17 | 12 | 119 |
| RP11-91M21 | 12 | 120.4 |
| RP11-119J23 | 12 | 121.2 |
| RP11-101P14 | 12 | 122.5 |
| RP11-110J12 | 12 | 124 |
| RP11-3L23 | 12 | 125.1 |
| RP11-665J20 | 12 | 127.3 |
| RP11-87C12 | 12 | 128.7 |
| RP11-512M8 | 12 | 129.1 |
| RP11-486O12 | 12 | 130.9 |
| RP11-526P6 | 12 | 135.5 |
| RP11-91B1 | 12 | 136.2 |
| RP11-81G12 | 12 | 137.7 |
| RP11-119J21 | 12 | 138.1 |
| RP11-89F23 | 12 | 138.5 |
| AC048343.14 | 12 | 146.5 |
| RP11-408E5 | 13 | 17.3 |
| RP11-110K18 | 13 | 18.1 |
| RP11-26D3 | 13 | 19 |
| RP11-347L8 | 13 | 20.2 |
| RP11-316G23 | 13 | 20.6 |
| RP11-300N13 | 13 | 22.9 |
| RP11-90M15 | 13 | 23.6 |
| RP11-111G7 | 13 | 24.2 |
| RP11-91C24 | 13 | 25.4 |
| RP11-89J10 | 13 | 25.9 |
| RP11-35M5 | 13 | 26.8 |
| RP11-90M5 | 13 | 28.6 |
| RP11-63C16 | 13 | 29.5 |
| RP11-367C11 | 13 | 30.3 |
| CTD-2037D17 | 13 | 31.4 |
| RP11-141M1 | 13 | 32.4 |
| RP11-87G1 | 13 | 32.5 |
| RP11-269G10 | 13 | 33.5 |
| RP11-90F5 | 13 | 33.9 |
| RP11-91K18 | 13 | 35.4 |
| RP11-495J3 | 13 | 36.4 |
| RP11-186J16 | 13 | 38.6 |
| RP11-83P2 | 13 | 40.1 |
| RP11-13I8 | 13 | 41.3 |
| RP11-117I13 | 13 | 42 |
| RP11-160G19 | 13 | 43.2 |
| RP11-71C5 | 13 | 43.7 |
| RP11-80H2 | 13 | 45.4 |
| RP11-457D13 | 13 | 46.2 |
| RP11-480G1 | 13 | 47.6 |
| RP11-189B4 | 13 | 48.2 |
| RP11-94N9 | 13 | 49 |
| RP11-90K7 | 13 | 50.5 |
| RP11-185C18 | 13 | 51.3 |
| RP11-91J7 | 13 | 52.3 |
| RP11-456B18 | 13 | 54.7 |
| RP11-100C24 | 13 | 56.8 |
| RP11-81D19 | 13 | 57.5 |
| RP11-142D16 | 13 | 59.1 |
| RP11-218B22 | 13 | 59.5 |
| RP11-282D7 | 13 | 63.2 |
| RP11-91F3 | 13 | 63.7 |
| RP11-37I8 | 13 | 64.6 |
| RP11-23B16 | 13 | 66.6 |
| AL138958.18 | 13 | 68.1 |
| RP11-1G3 | 13 | 69.2 |
| RP11-14B2 | 13 | 70.3 |
| RP11-81D9 | 13 | 71.4 |
| RP11-79I4 | 13 | 72 |
| RP11-132L12 | 13 | 73.3 |
| RP11-29G8 | 13 | 73.9 |
| RP11-138D23 | 13 | 74.9 |
| RP11-298H15 | 13 | 75.8 |
| AL359257.8 | 13 | 77.2 |
| RP11-318G21 | 13 | 78.2 |
| RP11-25J23 | 13 | 79.9 |
| RP11-80N10 | 13 | 81.2 |
| RP11-89A14 | 13 | 83.4 |
| RP11-118K20 | 13 | 84.7 |
| RP11-29C8 | 13 | 86.1 |
| RP11-30L8 | 13 | 86.6 |
| RP11-753M10 | 13 | 87.5 |
| RP11-29P20 | 13 | 88.1 |
| RP11-27D9 | 13 | 89.2 |
| RP11-114G1 | 13 | 89.9 |
| RP11-79H7 | 13 | 90.8 |
| RP11-51B13 | 13 | 91.6 |
| RP11-121J7 | 13 | 91.9 |
| RP11-165N12 | 13 | 92.9 |
| RP11-80B16 | 13 | 94.2 |

TABLE 2-continued

| clone_id | chromosome | linear |
|---|---|---|
| RP11-210E23 | 13 | 95 |
| RP11-74A12 | 13 | 95.6 |
| RP11-79A16 | 13 | 96.6 |
| RP11-83D23 | 13 | 97 |
| RP11-122A8 | 13 | 99.8 |
| RP11-366N24 | 13 | 100.4 |
| RP11-151A6 | 13 | 101.2 |
| RP11-90C11 | 13 | 101.8 |
| AL391122.9 | 13 | 102.5 |
| RP11-36L18 | 13 | 103.6 |
| RP11-202O6 | 13 | 104.5 |
| RP11-100K21 | 13 | 106.1 |
| RP11-25E13 | 13 | 107.2 |
| RP11-207D10 | 13 | 107.7 |
| AL445649.15 | 13 | 108.5 |
| RP11-330C15 | 13 | 109.4 |
| RP11-107H21 | 13 | 110 |
| RP11-90L1 | 13 | 111.5 |
| RP11-91C11 | 13 | 111.8 |
| RP11-474D23 | 13 | 112.4 |
| RP11-75F3 | 13 | 113 |
| RP11-98F14 | 13 | 114.5 |
| RP11-245B11 | 13 | 114.8 |
| RP11-391H12 | 13 | 117.7 |
| RP11-98N22 | 14 | 17 |
| RP11-89F2 | 14 | 17.4 |
| RP11-71E6 | 14 | 18.5 |
| RP11-566I2 | 14 | 18.6 |
| RP11-65O3 | 14 | 20 |
| RP11-81F9 | 14 | 20.3 |
| RP11-89K22 | 14 | 22.2 |
| RP11-529E4 | 14 | 25.5 |
| RP11-125A5 | 14 | 26.4 |
| RP11-369O9 | 14 | 27 |
| RP11-91K19 | 14 | 29 |
| RP11-91C17 | 14 | 29.4 |
| RP11-54H22 | 14 | 29.9 |
| RP11-557O15 | 14 | 30.5 |
| RP11-26M6 | 14 | 32.2 |
| RP11-465B6 | 14 | 33.4 |
| RP11-88D14 | 14 | 34.8 |
| RP11-91H1 | 14 | 35.3 |
| RP11-305B23 | 14 | 36.4 |
| RP11-88N14 | 14 | 37.8 |
| RP11-89D19 | 14 | 38.6 |
| RP11-89H24 | 14 | 40.5 |
| RP11-435L2 | 14 | 41.2 |
| RP11-453F20 | 14 | 43.1 |
| RP11-91J1 | 14 | 43.6 |
| RP11-52O23 | 14 | 45.8 |
| RP11-94K16 | 14 | 46.7 |
| RP11-90K14 | 14 | 47.7 |
| RP11-368A1 | 14 | 48.9 |
| RP11-262M8 | 14 | 50.4 |
| RP11-12P7 | 14 | 51.8 |
| RP11-172G1 | 14 | 53.2 |
| AL359234.4 | 14 | 54.6 |
| RP11-571J17 | 14 | 56.1 |
| RP11-2L22 | 14 | 57.3 |
| RP11-79M1 | 14 | 57.8 |
| RP11-471N20 | 14 | 58.9 |
| RP11-79I3 | 14 | 59.9 |
| RP11-445J13 | 14 | 61.6 |
| RP11-44K16 | 14 | 62.7 |
| RP11-63G22 | 14 | 63.1 |
| RP11-156E22 | 14 | 65.7 |
| RP11-79B13 | 14 | 66.6 |
| AL160191.3 | 14 | 68.4 |
| CTD-3014H8 | 14 | 69.1 |
| RP11-325N20 | 14 | 70.8 |
| RP11-89B22 | 14 | 71.5 |
| RP11-382O4 | 14 | 73.1 |
| CTD-2317F5 | 14 | 74.2 |
| RP11-81O20 | 14 | 74.9 |
| RP11-463C8 | 14 | 75.9 |
| RP11-63D17 | 14 | 76.7 |
| RP11-232C2 | 14 | 77.5 |

TABLE 2-continued

| clone_id | chromosome | linear |
|---|---|---|
| RP11-80L10 | 14 | 78.8 |
| RP11-114N19 | 14 | 79.7 |
| AL133279.7 | 14 | 87.1 |
| RP11-79J20 | 14 | 88.3 |
| RP11-99C24 | 14 | 89.4 |
| RP11-90H21 | 14 | 90.4 |
| RP11-90P19 | 14 | 90.4 |
| RP11-28G16 | 14 | 91.3 |
| RP11-374H13 | 14 | 92.1 |
| RP11-160P21 | 14 | 93.4 |
| RP11-80F23 | 14 | 95.1 |
| RP11-88L4 | 14 | 98.1 |
| RP11-431B1 | 14 | 98.4 |
| RP11-89J8 | 14 | 99.3 |
| RP11-90G22 | 14 | 100 |
| RP11-365N19 | 14 | 102.7 |
| RP11-454M12 | 14 | 102.8 |
| RP11-73M18 | 14 | 103.6 |
| RP11-894P9 | 14 | 103.6 |
| AL049840.8 | 14 | 104 |
| RP11-80H14 | 15 | 17.1 |
| AC090983.2 | 15 | 21.1 |
| RP11-339C21 | 15 | 21.8 |
| AC079090.3 | 15 | 23.9 |
| AC021360.4 | 15 | 24.9 |
| RP11-420B6 | 15 | 26 |
| RP11-303I17 | 15 | 26.7 |
| AC011938.4 | 15 | 28.4 |
| RP11-81N9 | 15 | 28.7 |
| RP11-194H7 | 15 | 29.4 |
| RP11-462A2 | 15 | 30.3 |
| RP11-79A5 | 15 | 33 |
| RP11-62L9 | 15 | 34.3 |
| RP11-521C20 | 15 | 35.1 |
| CTD-2339L15 | 15 | 35.7 |
| RP11-328J12 | 15 | 36.4 |
| RP11-79O13 | 15 | 38.4 |
| RP11-88J10 | 15 | 38.7 |
| RP11-329C22 | 15 | 40.3 |
| RP11-88D20 | 15 | 40.9 |
| RP11-81G13 | 15 | 42.2 |
| AC066615 | 15 | 42.8 |
| RP11-89O12 | 15 | 43.2 |
| RP11-154J22 | 15 | 44 |
| RP11-295H24 | 15 | 45 |
| RP11-416K5 | 15 | 45.9 |
| RP11-105D1 | 15 | 46.8 |
| RP11-313P18 | 15 | 47.5 |
| RP11-23N2 | 15 | 48.4 |
| RP11-316P21 | 15 | 48.8 |
| RP11-390M11 | 15 | 50.2 |
| RP11-548M13 | 15 | 51.2 |
| RP11-80N16 | 15 | 51.7 |
| RP11-139H15 | 15 | 52.7 |
| RP11-79C5 | 15 | 53.3 |
| CTD-2330J20 | 15 | 54.3 |
| CTD-2280O8 | 15 | 55 |
| RP11-79J15 | 15 | 55.4 |
| RP11-90A19 | 15 | 57.2 |
| RP11-89A6 | 15 | 59.2 |
| RP11-53H4 | 15 | 61.3 |
| RP11-70A7 | 15 | 62.6 |
| RP11-54P3 | 15 | 62.8 |
| RP11-85E15 | 15 | 63.8 |
| AC048383 | 15 | 66.2 |
| RP11-101C13 | 15 | 66.5 |
| RP11-64K10 | 15 | 68 |
| RP11-368G21 | 15 | 68.3 |
| RP11-500O23 | 15 | 69.3 |
| AC023300.6 | 15 | 71.1 |
| RP11-79J21 | 15 | 73.1 |
| RP11-338C8 | 15 | 74.2 |
| RP11-10K12 | 15 | 74.9 |
| AC015970.4 | 15 | 75.5 |
| RP11-81A1 | 15 | 76.3 |
| RP11-558F16 | 15 | 77.8 |
| AC011441.4 | 15 | 78.2 |

TABLE 2-continued

| clone_id | chromosome | linear |
|---|---|---|
| RP11-152F13 | 15 | 78.7 |
| RP11-81L17 | 15 | 80.2 |
| RP11-90B9 | 15 | 80.7 |
| RP11-91O13 | 15 | 80.9 |
| RP11-296P8 | 15 | 82.5 |
| RP11-80J8 | 15 | 84.1 |
| RP11-91E10 | 15 | 85.2 |
| RP11-533L13 | 15 | 85.7 |
| AC013787.9 | 15 | 86.9 |
| RP11-360F18 | 15 | 88.2 |
| RP11-79A7 | 15 | 89.4 |
| RP11-369O17 | 15 | 90.2 |
| RP11-79C10 | 15 | 93 |
| RP11-337N12 | 15 | 93.4 |
| RP11-120N1 | 15 | 94.7 |
| RP11-80F4 | 15 | 95.4 |
| RP11-397C10 | 15 | 96 |
| RP11-90E5 | 15 | 97.3 |
| RP11-14C10 | 15 | 98.5 |
| RP11-344L6 | 16 | 0.2 |
| RP11-334D3 | 16 | 1.3 |
| RP11-417B20 | 16 | 1.8 |
| RP11-433P17 | 16 | 3.1 |
| RP11-95P2 | 16 | 5.1 |
| RP11-89M4 | 16 | 5.6 |
| RP11-24M13 | 16 | 6.8 |
| RP11-349I11 | 16 | 7.5 |
| RP11-79M18 | 16 | 8.4 |
| RP11-475D10 | 16 | 9.7 |
| RP11-89D3 | 16 | 11.3 |
| RP11-49O6 | 16 | 12.2 |
| AC007216.2 | 16 | 12.6 |
| RP11-165M1 | 16 | 13 |
| RP11-81L19 | 16 | 15.5 |
| RP11-91M7 | 16 | 16.5 |
| RP11-396B14 | 16 | 18.1 |
| RP11-81F1 | 16 | 18.2 |
| RP11-79I15 | 16 | 19.2 |
| RP11-109D4 | 16 | 19.6 |
| RP11-141E3 | 16 | 22 |
| RP11-450G5 | 16 | 22.7 |
| RP11-146J7 | 16 | 24.3 |
| RP11-79F19 | 16 | 25.1 |
| RP11-167K14 | 16 | 26.5 |
| RP11-488I20 | 16 | 28.2 |
| CTA-670B5 | 16 | 28.4 |
| RP11-85E7 | 16 | 30.8 |
| RP11-499D5 | 16 | 32.8 |
| RP11-80F22 | 16 | 43.2 |
| RP11-79M6 | 16 | 44.8 |
| RP11-89O14 | 16 | 46.4 |
| RP11-474B12 | 16 | 47.4 |
| RP11-1103K14 | 16 | 48 |
| RP11-303G21 | 16 | 48.8 |
| RP11-98C8 | 16 | 49.3 |
| RP11-305A7 | 16 | 50 |
| RP11-147B17 | 16 | 51 |
| RP11-424K7 | 16 | 51.6 |
| RP11-142G1 | 16 | 52.7 |
| RP11-79E10 | 16 | 53.1 |
| RP11-466N18 | 16 | 54 |
| RP11-81D3 | 16 | 55 |
| RP11-212I21 | 16 | 55.9 |
| RP11-250E14 | 16 | 58.8 |
| RP11-79E15 | 16 | 59.9 |
| RP11-11E14 | 16 | 60.2 |
| RP11-246M14 | 16 | 62.4 |
| RP11-89G14 | 16 | 63 |
| RP11-3I14 | 16 | 64.2 |
| RP11-154N7 | 16 | 68.2 |
| RP11-5A19 | 16 | 69 |
| RP11-553M22 | 16 | 69.8 |
| RP11-89K4 | 16 | 73.1 |
| RP11-58M3 | 16 | 74.4 |
| RP11-90L19 | 16 | 75 |
| AC009054.6 | 16 | 78.1 |
| RP11-12H11 | 16 | 79.9 |
| RP11-91O9 | 16 | 80.8 |
| RP11-118F19 | 16 | 85.2 |
| RP11-90J5 | 16 | 86.4 |
| RP11-80H6 | 16 | 88.4 |
| RP11-309G16 | 16 | 89.3 |
| RP11-443M9 | 16 | 89.6 |
| RP11-7D23 | 16 | 92.1 |
| RP11-79A1 | 16 | 92.2 |
| RP4-597G12 | 16 | 93.2 |
| AC027455.12 | 17 | 0.4 |
| RP11-91C8 | 17 | 0.6 |
| RP11-356I18 | 17 | 0.7 |
| RP11-26N16 | 17 | 0.9 |
| RP5-1029F21 | 17 | 1.21 |
| RP11-4F24 | 17 | 1.8 |
| RP11-380H7 | 17 | 2.2 |
| RP11-545O6 | 17 | 4.3 |
| RP11-459C13 | 17 | 4.4 |
| RP11-457I18 | 17 | 5.6 |
| CTB-44J6 | 17 | 6.7 |
| RP11-89D11 | 17 | 8.9 |
| RP11-405P10 | 17 | 9.6 |
| CTB-41I6 | 17 | 11.1 |
| RP11-383G9 | 17 | 11.7 |
| RP11-385G5 | 17 | 14.2 |
| RP11-90G21 | 17 | 15.6 |
| RP11-89F21 | 17 | 16 |
| RP11-78J16 | 17 | 16.9 |
| RP11-89K6 | 17 | 17.9 |
| RP11-746E8 | 17 | 18.5 |
| RP11-404D6 | 17 | 19.3 |
| RP11-79O4 | 17 | 24.8 |
| RP11-363P3 | 17 | 25 |
| RP11-88B16 | 17 | 29.1 |
| RP11-73F15 | 17 | 30 |
| RP11-79O9 | 17 | 31.7 |
| RP11-79K15 | 17 | 32.9 |
| RP11-521P1 | 17 | 33.4 |
| RP11-58O8 | 17 | 34.9 |
| RP11-81D5 | 17 | 39 |
| RP11-19G24 | 17 | 39.4 |
| RP11-513C18 | 17 | 40.4 |
| RP11-89A22 | 17 | 40.8 |
| RP11-29C11 | 17 | 41.6 |
| AC016889.11 | 17 | 42.7 |
| RP11-266I24 | 17 | 43 |
| RP11-436J4 | 17 | 44.1 |
| RP11-510P20 | 17 | 46.5 |
| RP11-79O18 | 17 | 46.9 |
| RP11-110H20 | 17 | 49.4 |
| RP11-81D7 | 17 | 50.3 |
| CTB-43I4 | 17 | 53.2 |
| RP11-42M14 | 17 | 54.1 |
| RP11-524I12 | 17 | 57.2 |
| RP11-506H21 | 17 | 59.7 |
| RP11-481M4 | 17 | 61.1 |
| AC040904.2 | 17 | 61.9 |
| RP11-561K8 | 17 | 63.7 |
| RP11-89H15 | 17 | 65.8 |
| RP11-52B5 | 17 | 66.9 |
| RP11-89L7 | 17 | 68 |
| RP11-387O17 | 17 | 69.6 |
| RP11-79K13 | 17 | 70.1 |
| RP11-300G13 | 17 | 71.2 |
| RP11-90L11 | 17 | 71.7 |
| AC087301.3 | 17 | 73 |
| RP11-65C22 | 17 | 75.4 |
| RP11-91M1 | 17 | 75.7 |
| RP11-91O17 | 17 | 75.7 |
| RP11-76G4 | 17 | 76.7 |
| RP11-89B11 | 17 | 77.5 |
| RP11-61B11 | 17 | 77.9 |
| RP11-165J13 | 17 | 80.9 |
| RP11-46E14 | 17 | 81.4 |
| RP11-55N14 | 18 | 4.3 |
| RP11-80L18 | 18 | 5.7 |
| RP11-102E12 | 18 | 6.4 |

TABLE 2-continued

| clone_id | chromosome | linear |
|---|---|---|
| RP11-105C15 | 18 | 7.5 |
| RP11-91I8 | 18 | 8.1 |
| RP11-102O20 | 18 | 11.2 |
| AP001077.4 | 18 | 14.4 |
| RP11-151D11 | 18 | 15.6 |
| RP11-411B10 | 18 | 16.5 |
| RP11-79F3 | 18 | 21.6 |
| RP11-90G7 | 18 | 26.5 |
| RP11-676D16 | 18 | 27.9 |
| RP11-79G13 | 18 | 28.8 |
| AC021224.7 | 18 | 30.5 |
| RP11-63N12 | 18 | 33.2 |
| RP11-79G5 | 18 | 33.8 |
| RP11-90B5 | 18 | 35.2 |
| RP11-104N11 | 18 | 36.5 |
| RP11-89M10 | 18 | 40.5 |
| RP11-20A13 | 18 | 44.9 |
| RP11-91K12 | 18 | 45.6 |
| RP11-80P2 | 18 | 48 |
| RP11-160B24 | 18 | 55 |
| RP11-153B11 | 18 | 55.6 |
| RP11-79L5 | 18 | 58.7 |
| RP11-4G8 | 18 | 59.6 |
| AC067859.3 | 18 | 60.2 |
| RP11-91H13 | 18 | 61.7 |
| RP11-75O12 | 18 | 65.2 |
| RP11-90B3 | 18 | 65.8 |
| RP11-89I22 | 18 | 65.9 |
| RP11-88B2 | 18 | 67.4 |
| RP11-105L16 | 18 | 69 |
| RP11-79A24 | 18 | 69.2 |
| RP11-90A7 | 18 | 69.2 |
| RP11-49H23 | 18 | 69.4 |
| RP11-57F7 | 18 | 71.5 |
| RP11-90L15 | 18 | 73.4 |
| RP11-90L3 | 18 | 79 |
| RP11-91C19 | 18 | 80.5 |
| RP11-89N1 | 18 | 81.5 |
| AP001933.3 | 18 | 86.9 |
| RP11-54G9 | 19 | 4.2 |
| RP11-268O21 | 19 | 4.4 |
| AC027319.5 | 19 | 6.8 |
| CTD-3193O13 | 19 | 10.1 |
| RP11-79F15 | 19 | 11.1 |
| RP11-91O21 | 19 | 13.1 |
| RP11-19I2 | 19 | 14.6 |
| AC010422.7 | 19 | 15.3 |
| RP11-56K21 | 19 | 17.2 |
| CTD-2231E14 | 19 | 19.2 |
| AC004447.1 | 19 | 22.4 |
| RP11-152P7 | 19 | 42.7 |
| RP11-46I12 | 19 | 43.8 |
| RP11-110J19 | 19 | 43.9 |
| RP11-79M11 | 19 | 46.4 |
| RP11-91H20 | 19 | 46.8 |
| RP11-147D7 | 19 | 47.1 |
| AC008555.5 | 19 | 49.9 |
| RP11-92J4 | 19 | 51 |
| RP11-118P21 | 19 | 52.5 |
| RP11-46C6 | 19 | 52.9 |
| RP11-208I3 | 19 | 57.4 |
| RP11-210C7 | 19 | 59.6 |
| RP11-79A22 | 19 | 60.3 |
| RP11-21J15 | 19 | 60.9 |
| RP11-126L20 | 19 | 61.6 |
| RP11-17I20 | 19 | 63.8 |
| RP11-510I16 | 19 | 66.5 |
| RP11-79A3 | 19 | 68.7 |
| RP11-79I16 | 19 | 69.4 |
| RP11-35J17 | 19 | 70.5 |
| AC005261.1 | 19 | 74.3 |
| RP11-420P11 | 19 | 75.9 |
| RP5-1103G7 | 20 | 0.3 |
| RP5-863C7 | 20 | 0.5 |
| AL031665.19 | 20 | 1.2 |
| AL031665.19 | 20 | 1.3 |
| AL049634.8 | 20 | 1.4 |
| RP4-684O24 | 20 | 1.9 |
| RP4-816K17 | 20 | 2.3 |
| RP11-26F18 | 20 | 3.2 |
| RP4-599I11 | 20 | 4.7 |
| RP5-1054C24 | 20 | 5.7 |
| RP5-859D4 | 20 | 6.7 |
| RP5-836E8 | 20 | 7.7 |
| RP11-79E16 | 20 | 8.6 |
| RP5-873P14 | 20 | 9.5 |
| RP5-931K24 | 20 | 10.3 |
| RP11-90E23 | 20 | 11.2 |
| RP11-88P14 | 20 | 12.2 |
| RP11-89F13 | 20 | 14.5 |
| RP11-91O7 | 20 | 15.6 |
| RP11-80N12 | 20 | 16.8 |
| RP11-11M17 | 20 | 17.8 |
| RP11-91M17 | 20 | 19.4 |
| RP11-91G1 | 20 | 20.9 |
| RP4-788L20 | 20 | 22.5 |
| RP11-218C14 | 20 | 23.5 |
| RP11-79K14 | 20 | 25 |
| RP11-90H19 | 20 | 25.6 |
| RP3-410C9 | 20 | 26.2 |
| RP5-1018D12 | 20 | 29.8 |
| RP5-857M17 | 20 | 30.1 |
| RP5-836N17 | 20 | 30.6 |
| RP5-1125A11 | 20 | 32.3 |
| RP4-756N5 | 20 | 33.5 |
| RP5-901O8 | 20 | 34.3 |
| RP3-460J8 | 20 | 35.1 |
| RP11-138A15 | 20 | 35.9 |
| RP4-564F22 | 20 | 36.8 |
| RP4-616B8 | 20 | 37.4 |
| RP5-1123D4 | 20 | 38.9 |
| RP5-824J5 | 20 | 39 |
| RP4-661I20 | 20 | 40 |
| RP1-3E5 | 20 | 40.9 |
| RP5-970A17 | 20 | 41.1 |
| AL031676.3 | 20 | 41.5 |
| RP11-169A6 | 20 | 43.5 |
| RP3-337O18 | 20 | 44.3 |
| RP11-323C15 | 20 | 45.3 |
| RP3-453C12 | 20 | 45.8 |
| RP1-73E16 | 20 | 46.3 |
| RP5-1063B2 | 20 | 48.1 |
| RP5-963K23 | 20 | 48.3 |
| RP11-5P14 | 20 | 49.4 |
| RP5-1185N5 | 20 | 50.4 |
| RP4-715N11 | 20 | 51.1 |
| RP11-91L1 | 20 | 51.8 |
| RP5-885A10 | 20 | 54.4 |
| RP4-749H19 | 20 | 55.4 |
| RP5-907D15 | 20 | 57 |
| RP5-1043L13 | 20 | 58.6 |
| RP5-1040G13 | 20 | 59.5 |
| RP5-1107C24 | 20 | 60.4 |
| RP5-1005F21 | 20 | 60.5 |
| RP5-885L7 | 20 | 61.5 |
| AL158091.31 | 20 | 62.4 |
| RP4-583P15 | 20 | 62.4 |
| AL121581.41 | 20 | 62.7 |
| RP11-89M24 | 21 | 13.5 |
| AL163206 | 21 | 14.3 |
| RP11-15E10 | 21 | 16.5 |
| RP11-375O2 | 21 | 17 |
| RP11-49B5 | 21 | 18.1 |
| RP11-49J9 | 21 | 18.8 |
| RP11-64I12 | 21 | 19.7 |
| RP11-97F14 | 21 | 20.5 |
| RP11-80N20 | 21 | 21.4 |
| RP11-13J15 | 21 | 21.8 |
| RP11-88D18 | 21 | 23.1 |
| RP11-15H6 | 21 | 24.4 |
| RP11-90A17 | 21 | 25.4 |
| RP11-79G23 | 21 | 27 |
| RP11-30N6 | 21 | 27.5 |
| RP11-191I6 | 21 | 29.1 |

TABLE 2-continued

| clone_id | chromosome | linear |
|---|---|---|
| RP11-147H1 | 21 | 30 |
| RP11-79D9 | 21 | 30.9 |
| RP11-79A12 | 21 | 32.3 |
| RP11-17O20 | 21 | 33 |
| AL163281.2 | 21 | 37.9 |
| RP11-114H1 | 21 | 38.8 |
| RP11-120C17 | 21 | 39.4 |
| RP11-88N2 | 21 | 41.3 |
| RP11-91O6 | 22 | 15.2 |
| RP11-81B3 | 22 | 15.6 |
| RP11-186O8 | 22 | 16.8 |
| RP11-22M5 | 22 | 19.1 |
| RP11-76E8 | 22 | 21.4 |
| RP5-930L11 | 22 | 22 |
| RP11-89A2 | 22 | 22.9 |
| RP11-91K24 | 22 | 24.1 |
| RP11-79G21 | 22 | 25 |
| RP11-79G6 | 22 | 27.2 |
| RP11-247I13 | 22 | 28.7 |
| Z73979.1 | 22 | 30.1 |
| RP1-215F16 | 22 | 32.3 |
| RP11-89D12 | 22 | 33 |
| RP5-1119A7 | 22 | 33.6 |
| RP3-327J16 | 22 | 35.9 |
| RP3-370M22 | 22 | 37 |
| RP5-979N1 | 22 | 38.4 |
| RP5-821D11 | 22 | 38.9 |
| RP3-323M22 | 22 | 40.1 |
| RP1-185D5 | 22 | 40.6 |
| RP1-32I10 | 22 | 41.5 |
| RP4-695O20 | 22 | 42.3 |
| RP11-140I15 | 22 | 42.9 |
| RP5-1163J1 | 22 | 43.4 |
| RP1-111J24 | 22 | 44.4 |
| RP11-262A13 | 22 | 45.8 |
| RP3-355C18 | 22 | 47.1 |
| U62317.2 | 22 | 47.7 |
| U82668.1 | X | 0.04 |
| LLNOYCO3M"15D10 | X | 0.05 |
| RP4-617A9 | X | 0.9 |
| AC079264.23 | X | 2.6 |
| RP11-366M24 | X | 3.9 |
| CTB-9P2 | X | 5.7 |
| RP11-383I22 | X | 6.7 |
| RP11-451G24 | X | 7 |
| RP11-89B5 | X | 8.3 |
| AC005859.1 | X | 10.3 |
| RP11-90F9 | X | 11.4 |
| AC095352.5 | X | 12.6 |
| RP11-143E20 | X | 14.5 |
| RP11-79B3 | X | 15.8 |
| RP5-958B3 | X | 16.8 |
| RP1-245G19 | X | 17.1 |
| AC017058.4 | X | 18.2 |
| RP11-497C10 | X | 19.2 |
| RP11-507P24 | X | 20 |
| RP11-487M22 | X | 25.2 |
| RP6-27C10 | X | 25.8 |
| CTB-229E10 | X | 27.1 |
| RP11-89L23 | X | 27.3 |
| RP11-122N14 | X | 28.1 |
| RP11-124H12 | X | 28.4 |
| RP5-1147O16 | X | 29 |
| AL031643.1 | X | 29.9 |
| RP11-70D7 | X | 31 |
| RP13-46M24 | X | 33.2 |
| CTB-227D11 | X | 34 |
| RP11-91I16 | X | 34.3 |
| RP11-495K15 | X | 35.1 |
| RP11-506C6 | X | 35.8 |
| RP11-258I23 | X | 37.2 |
| RP11-524P6 | X | 38.3 |
| RP11-252K10 | X | 39.3 |
| RP11-561I16 | X | 40.1 |
| RP4-551E13 | X | 40.8 |
| AL020989.2 | X | 42.2 |
| RP1-30G7 | X | 43 |
| RP1-306D1 | X | 43.9 |
| RP1-212G6 | X | 44.7 |
| DJ230G1 | X | 44.9 |
| RP11-107C19 | X | 45.6 |
| RP11-58H17 | X | 46.6 |
| RP11-637B23 | X | 47.8 |
| RP11-363G10 | X | 48.7 |
| ICRFC100H0164 | X | 49.2 |
| RP3-501A4 | X | 49.9 |
| RP11-292J24 | X | 50.5 |
| RP11-266I3 | X | 51.2 |
| RP11-465E19 | X | 52.1 |
| RP3-323P24 | X | 53.2 |
| ICRFC100G11100 | X | 53.5 |
| ICRFC104A07135 | X | 53.8 |
| RP3-344I7 | X | 54.2 |
| RP11-90N17 | X | 57 |
| RP11-151A2 | X | 57.5 |
| RP11-90I7 | X | 58.7 |
| RP1-80C12 | X | 60.8 |
| RP11-523P2 | X | 61.6 |
| RP11-470E22 | X | 62.8 |
| ICRFC104E01154 | X | 63.6 |
| RP11-451A4 | X | 63.6 |
| RP11-177A4 | X | 64.6 |
| RP11-291O7 | X | 65.1 |
| RP11-136A22 | X | 66.2 |
| RP13-260P4 | X | 66.9 |
| RP13-36G14 | X | 67.6 |
| RP3-368A4 | X | 67.9 |
| ICRFC100H0130 | X | 68 |
| RP11-79C13 | X | 69.8 |
| RP11-236O12 | X | 70.7 |
| RP4-570L12 | X | 71.6 |
| RP11-346E8 | X | 73.5 |
| ICRFC104B1939 | X | 74.5 |
| RP11-217H19 | X | 74.7 |
| RP1-75N13 | X | 75.9 |
| RP11-405O21 | X | 76.6 |
| RP11-326A14 | X | 77.2 |
| RP1-223D17 | X | 78.9 |
| RP1-287L14 | X | 80 |
| RP11-192B18 | X | 80.8 |
| RP11-145I17 | X | 81 |
| RP3-473J6 | X | 82.7 |
| RP11-156J23 | X | 86.8 |
| RP11-88F12 | X | 87.3 |
| RP11-465C5 | X | 88.5 |
| RP11-483J19 | X | 88.9 |
| AL449189.1 | X | 89.9 |
| RP1-117P19 | X | 91.1 |
| RP13-75G22 | X | 92.2 |
| RP11-485F13 | X | 93.1 |
| RP3-377O6 | X | 94 |
| RP11-89G18 | X | 95.1 |
| Z70281 | X | 95.7 |
| RMCOXP001 | X | 96.4 |
| RP1-198P4 | X | 97.6 |
| RP11-572H24 | X | 99.6 |
| RP1-315B17 | X | 100.5 |
| RP1-75H8 | X | 101.9 |
| RP5-1070B1 | X | 102.6 |
| AL031177.1 | X | 103.4 |
| RP11-40K1 | X | 103.9 |
| RP1-302C5 | X | 105.3 |
| CTB-423D18 | X | 105.8 |
| RP11-14G9 | X | 105.9 |
| RP11-80F14 | X | 106.8 |
| RP11-485M23 | X | 107.5 |
| RP5-961O8 | X | 108.2 |
| RP5-964N17 | X | 109.1 |
| RP11-491C15 | X | 110.5 |
| RP3-525N14 | X | 113.4 |
| CTB-281O10 | X | 114.3 |
| RP1-93I3 | X | 114.3 |
| RP11-566B18 | X | 116.7 |
| RP6-64P14 | X | 118.2 |

TABLE 2-continued

| clone_id | chromosome | linear |
|---|---|---|
| RP3-370N13 | X | 118.4 |
| RP5-1052M9 | X | 119.6 |
| RP1-96A9 | X | 120.4 |
| RP1-256K24 | X | 121.2 |
| RP11-79C15 | X | 122 |
| RP1-293E14 | X | 123.5 |
| RP3-454M7 | X | 124.4 |
| RP5-875H3 | X | 125.7 |
| RP1-297J13 | X | 126.2 |
| RP1-197O17 | X | 126.9 |
| RP1-84F12 | X | 128.8 |
| CTB-45B24 | X | 129.5 |
| RP4-809E13 | X | 130.4 |
| RP11-112K13 | X | 132.4 |
| RP11-483M22 | X | 133.2 |
| RP5-833B2 | X | 134.2 |
| RP13-34G21 | X | 135.1 |
| CTB-138O16 | X | 136 |
| RP1-177G6 | X | 136.1 |
| RP6-232G24 | X | 137.3 |
| RP1-231L4 | X | 138.7 |
| RP11-514L15 | X | 139.3 |
| RP1-145B12 | X | 140.1 |
| RP1-73A14 | X | 142.4 |
| RP5-824H1 | X | 143 |
| RP11-489K19 | X | 143.5 |
| c31.4 | X | 143.6 |
| L31948.1 | X | 145.9 |
| RP11-414C23 | Y | 2.8 |
| RP11-71M14 | Y | 15.9 |
| RP11-91A13 | Y | 17.7 |
| AC009235.4 | Y | 20 |

Substrate Surfaces

The compilations, or sets, libraries or collections, of nucleic acids, can be immobilized (directly or indirectly, covalently or by other means) to any substrate surface. The arrays of the invention can incorporate any substrate surface, e.g., a substrate means. The substrate surfaces can be of a rigid, semi-rigid or flexible material. The substrate surfaces can be flat or planar, be shaped as wells, raised regions, etched trenches, pores, beads, filaments, or the like. Substrates can be of any material upon which a nucleic acid (e.g., a "capture probe") can be directly or indirectly bound. For example, suitable materials can include paper, glass (see, e.g., U.S. Pat. No. 5,843,767), ceramics, quartz or other crystalline substrates (e.g. gallium arsenide), metals, metalloids, polacryloylmorpholide, various plastics and plastic copolymers, Nylon™, Teflon™, polyethylene, polypropylene, poly(4-methylbutene), polystyrene, polystyrene/latex, polymethacrylate, poly(ethylene terephthalate), rayon, nylon, poly(vinyl butyrate), polyvinylidene difluoride (PVDF) (see, e.g., U.S. Pat. No. 6,024,872), silicones (see, e.g., U.S. Pat. No. 6,096,817), polyformaldehyde (see, e.g., U.S. Pat. Nos. 4,355,153; 4,652,613), cellulose (see, e.g., U.S. Pat. No. 5,068,269), cellulose acetate (see, e.g., U.S. Pat. No. 6,048,457), nitrocellulose, various membranes and gels (e.g., silica aerogels, see, e.g., U.S. Pat. No. 5,795,557), paramagnetic or superparamagnetic microparticles (see, e.g., U.S. Pat. No. 5,939,261) and the like. Reactive functional groups can be, e.g., hydroxyl, carboxyl, amino groups or the like. Silane (e.g., mono- and dihydroxyalkylsilanes, aminoalkyltrialkoxysilanes, 3-aminopropyl-triethoxysilane, 3-aminopropyltrimethoxysilane) can provide a hydroxyl functional group for reaction with an amine functional group.

Nucleic Acids and Detectable Moieties: Incorporating Labels and Scanning Arrays

In making and using the compilations, or sets, libraries or collections, of nucleic acids and arrays and practicing the methods of the invention, nucleic acids associated with a detectable label can be used. The detectable label can be incorporated into, associated with or conjugated to a nucleic acid. Any detectable moiety can be used. The association with the detectable moiety can be covalent or non-covalent. In another aspect, the array-immobilized nucleic acids and sample nucleic acids are differentially detectable, e.g., they have different labels and emit difference signals.

Useful labels include, e.g., $^{32}P$, $^{35}S$, $^{3}H$, $^{14}C$, $^{125}I$, $^{131}I$; fluorescent dyes (e.g., Cy5™, Cy3™, FITC, rhodamine, lanthamide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid to be detected, or it can be attached to a probe or antibody that hybridizes or binds to the target. A peptide can be made detectable by incorporating (e.g., into a nucleoside base) predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., Mansfield (1995) Mol Cell Probes 9:145-156. In array-based CGH, fluors can be paired together; for example, one fluor labeling the control (e.g., the "nucleic acid of "known, or normal, karyotype") and another fluor the test nucleic acid (e.g., from a chorionic villus sample or a cancer cell sample). Exemplary pairs are: rhodamine and fluorescein (see, e.g., DeRisi (1996) Nature Genetics 14:458-460); lissamine-conjugated nucleic acid analogs and fluorescein-conjugated nucleotide analogs (see, e.g., Shalon (1996) supra); Spectrum Red™ and Spectrum Green™ (Vysis, Downers Grove, Ill.); Cy3™ and Cy5™. Cy3™ and Cy5™ can be used together; both are fluorescent cyanine dyes produced by Amersham Life Sciences (Arlington Heights, Ill.). Cyanine and related dyes, such as merocyanine, styryl and oxonol dyes, are particularly strongly light-absorbing and highly luminescent, see, e.g., U.S. Pat. Nos. 4,337,063; 4,404,289; 6,048,982.

Other fluorescent nucleotide analogs can be used, see, e.g., Jameson (1997) Methods Enzymol. 278:363-390; Zhu (1994) Nucleic Acids Res. 22:3418-3422. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

Detectable moieties can be incorporated into sample genomic nucleic acid and, if desired, any member of the compilation of nucleic acids or array-immobilized nucleic acids, by covalent or non-covalent means, e.g., by transcription, such as by random-primer labeling using Klenow polymerase, or "nick translation," or, amplification, or equivalent. For example, in one aspect, a nucleoside base is conjugated to a detectable moiety, such as a fluorescent dye, e.g., Cy3™ or Cy5™, and then incorporated into a sample genomic nucleic acid. Samples of genomic DNA can be incorporated with Cy3™- or Cy5™-dCTP conjugates mixed with unlabeled dCTP. Cy5™ is typically excited by the 633 nm line of HeNe laser, and emission is collected at 680 nm. See also, e.g., Bartosiewicz (2000) Archives of Biochem. Biophysics 376:66-73; Schena (1996) Proc. Natl. Acad. Sci. USA 93:10614-10619; Pinkel (1998) Nature Genetics 20:207-211; Pollack (1999) Nature Genetics 23:41-46.

In another aspect, when using PCR or nick translation to label nucleic acids, modified nucleotides synthesized by coupling allylamine-dUTP to the succinimidyl-ester derivatives of the fluorescent dyes or haptens (such as biotin or digoxigenin) are used; this method allows custom preparation of most common fluorescent nucleotides, see, e.g., Henegariu (2000) Nat. Biotechnol. 18:345-348.

In the compilation of nucleic acids, arrays and methods of the invention, labeling with a detectable composition (labeling with a detectable moiety) also can include a nucleic acid attached to another biological molecule, such as a nucleic acid, e.g., a nucleic acid in the form of a stem-loop structure as a "molecular beacon" or an "aptamer beacon." Molecular beacons as detectable moieties are well known in the art; for example, Sokol (1998) Proc. Natl. Acad. Sci. USA 95:11538-11543, synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (2001) Biochemistry 40:9387-9395, describing a molecular beacon comprised of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi (2001) Anal. Biochem. 294:126-131; Poddar (2001) Mol. Cell. Probes 15:161-167; Kaboev (2000) Nucleic Acids Res. 28:E94. Aptamer beacons can adopt two or more conformations, one of which allows ligand binding. A fluorescence-quenching pair is used to report changes in conformation induced by ligand binding. See also, e.g., Yamamoto (2000) Genes Cells 5:389-396; Smirnov (2000) Biochemistry 39:1462-1468.

Detecting Dyes and Fluors

In addition to labeling nucleic acids with fluorescent dyes, the invention can be practiced using any apparatus or methods to detect "detectable labels" of a sample nucleic acid, a member of the compilation of nucleic acids, or an array-immobilized nucleic acid, or, any apparatus or methods to detect nucleic acids specifically hybridized to each other. In one aspect, devices and methods for the simultaneous detection of multiple fluorophores are used; they are well known in the art, see, e.g., U.S. Pat. Nos. 5,539,517; 6,049,380; 6,054,279; 6,055,325; 6,294,331. Any known device or method, or variation thereof, can be used or adapted to practice the methods of the invention, including array reading or "scanning" devices, such as scanning and analyzing multicolor fluorescence images; see, e.g., U.S. Pat. Nos. 6,294,331; 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also published U.S. patent applications Nos. 20010018514; 20010007747; published international patent applications Nos. WO0146467 A; WO9960163 A; WO0009650 A; WO0026412 A; WO0042222 A; WO0047600 A; WO0101144 A.

For example a spectrograph can image an emission spectrum onto a two-dimensional array of light detectors; a full spectrally resolved image of the array is thus obtained. Photophysics of the fluorophore, e.g., fluorescence quantum yield and photodestruction yield, and the sensitivity of the detector are read time parameters for an oligonucleotide array. With sufficient laser power and use of Cy5™ and/or Cy3™, which have lower photodestruction yields an array can be read in less than 5 seconds.

When using two or more fluors together (e.g., as in a CGH), such as Cy3™ and Cy5™, it is necessary to create a composite image of all the fluors. To acquire the two or more images, the array can be scanned either simultaneously or sequentially. Charge-coupled devices, or CCDs, are used in microarray scanning systems, including practicing the methods of the invention. Thus, CCDs used in the methods of the invention can scan and analyze multicolor fluorescence images. Color discrimination can also be based on 3-color CCD video images; these can be performed by measuring hue values. Hue values are introduced to specify colors numerically. Calculation is based on intensities of red, green and blue light (RGB) as recorded by the separate channels of the camera. The formulation used for transforming the RGB values into hue, however, simplifies the data and does not make reference to the true physical properties of light. Alternatively, spectral imaging can be used; it analyzes light as the intensity per wavelength, which is the only quantity by which to describe the color of light correctly. In addition, spectral imaging can provide spatial data, because it contains spectral information for every pixel in the image. Alternatively, a spectral image can be made using brightfield microscopy, see, e.g., U.S. Pat. No. 6,294,331.

Data Analysis

The methods of the invention further comprise data analysis, which can include the steps of determining, e.g., fluorescent intensity as a function of substrate position, removing "outliers" (data deviating from a predetermined statistical distribution), or calculating the relative binding affinity of the targets from the remaining data. The resulting data can be displayed as an image with color in each region varying according to the light emission or binding affinity between targets and probes. See, e.g., U.S. Pat. Nos. 5,324,633; 5,863,504; 6,045,996. The invention can also incorporate a device for detecting a labeled marker on a sample located on a support, see, e.g., U.S. Pat. No. 5,578,832.

Sources of Genomic Nucleic Acid

The invention provides methods of detecting a genetic mosaicism in any sample comprising nucleic acid, such as a cell population or tissue or fluid sample, by performing an array-based comparative genomic hybridization (CGH). The nucleic acid can be derived from (e.g., isolated from, amplified from, cloned from) genomic DNA. The genomic DNA can be from any source.

In one aspect, the cell, tissue or fluid sample from which the nucleic acid sample is prepared is taken from a patient suspected of having a pathology or a condition associated with genetic defects. The causality, diagnosis or prognosis of the pathology or condition may be associated with genetic defects, e.g., with genomic nucleic acid base substitutions, amplifications, deletions and/or translocations. The cell, tissue or fluid can be from, e.g., amniotic samples, chorionic villus samples (CVS), serum, blood, chord blood or urine samples, CSF or bone marrow aspirations, fecal samples, saliva, tears, tissue and surgical biopsies, needle or punch biopsies, and the like.

Methods of isolating cell, tissue or fluid samples are well known to those of skill in the art and include, but are not limited to, aspirations, tissue sections, drawing of blood or other fluids, surgical or needle biopsies, and the like. A "clinical sample" derived from a patient includes frozen sections or paraffin sections taken for histological purposes. The sample can also be derived from supernatants (of cell cultures), lysates of cells, cells from tissue culture in which it may be desirable to detect levels of mosaicisms, including chromosomal abnormalities and copy numbers.

EXAMPLES

The following example is offered to illustrate, but not to limit the claimed invention.

Example 1

Making Nucleic Acid Arrays

The following example demonstrates exemplary protocol for making an array of the invention.

Making BAC Microarrays:

BAC clones greater than fifty kilobases (50 kb), and up to about 300 kb, are grown up in Terrific Broth medium. Larger inserts, e.g., clones >300 kb, and smaller inserts, about 1 to 20 kb, are also be used. DNA is prepared by a modified alkaline lysis protocol (see, e.g., Sambrook). The DNA is labeled, as described below.

The DNA is then chemically modified as described by U.S. Pat. No. 6,048,695. The modified DNA is then dissolved in proper buffer and printed directly on clean glass surfaces as described by U.S. Pat. No. 6,048,695. Usually multiple spots are printed for each clone.

Example 2

Nucleic Acid Labeling and DNase Enzyme Fragmentation

A standard random priming method is used to label genomic DNA before its attachment to the array, see, e.g., Sambrook. Sample nucleic acid is also similarly labeled. Cy3™ or Cy5™ labeled nucleotides are supplemented together with corresponding unlabeled nucleotides at a molar ratio ranging from 0.0 to about 6 (unlabeled nucleotide to labeled nucleotides). Labeling is carried out at 37° C. for 2 to 10 hours. After labeling the reaction mix is heated up to 95° C. to 100° C. for 3 to 5 minutes to inactivate the polymerase and denature the newly generated, labeled "probe" nucleic acid from the template.

The heated sample is then chilled on ice for 5 minutes. "Calibrated" DNase (DNA endonuclease) enzyme is added to fragment the labeled template (generated by random priming). "Trace" amounts of DNase is added (final concentration was 0.2 to 2 ng/ml; incubation time 15 to 30 minutes) to digest/fragment the labeled nucleic acid to segments of about 30 to about 100 bases in size.

Example 3

Hybridization of Nucleic Acid Samples to Arrays

The following example sets forth exemplary methods for pretreating nucleic acid samples and hybridizing these samples to arrays. This exemplary hybridization protocol can be used to determine if a nucleic acid segment, such as a genomic clone, is within the scope of the invention (e.g., is a member of a compilation, library, clone set of the invention).

Step 1: Pretreat DNA Samples

Random prime labeling of large sized DNA samples, such as genomic DNA, can be more efficient if the DNA sample is first digested to produce smaller fragments. For every test sample to be analyzed, four genomic DNA digests were performed: two of the test sample and two of an appropriate reference or control sample.

1. Restriction enzyme digest of genomic DNA: on ice, pipet the following into an autoclaved microcentrifuge tube:

DNA X µl for 1 µg

React 3 10×Buffer 5 µl

Eco RI 2 µl (20 units)

Water (orange vial) µl to a final volume of 50 µl

2. After addition of the enzyme and DNA, mix briefly by vortexing and recollect samples by brief centrifugation.

3. Incubate samples overnight (16 hours) at 37° C.

4. Determine the completion of the reaction by removing a 5 µl aliquot from the reaction mix, and analyzing the aliquot by agarose gel electrophoresis (0.8% agarose). If the digestion is complete, stop the reaction by incubating in a heating block at 72° C. for 10 minutes. It is recommended to fill the wells of the heating block with water approximately 15 minutes before denaturing the samples so that the tubes are in contact with water at 72° C.

5. Re-purify the digested DNA sample (either by phenol/chloroform extraction/EtOH precipitation or a suitable commercially available 'post-enzyme digestion/PCR clean-up kit' such as Zymo Research's DNA Clean and Concentrator TM-5 Cat No. D4005). Note: It is recommended to requantifying the DNA samples at this juncture to ensure that equitable amounts of the test and reference samples will be labeled in the following step.

At least 500 ng of digested DNA of each sample were used for labeling.

Genomic DNA samples adequately digested with a four base pair (4-bp) cutter restriction enzyme, such as EcoRI, should produce a relatively homogenous smear extending from 20 kb to approximately 600 bp.

Step 2: Differentially Label DNA with Cy3-dCTP and Cy5-dCTP

The objective in this step is to label the test and reference samples with both Cy-3 and Cy-5 to facilitate the co-hybridization between the Cy-3 labeled test and Cy-5 labeled reference samples, and conversely the Cy-5 labeled test and Cy-3 labeled reference samples.

1. To the re-purified DNA samples, add sterile water to bring the total volume to 25 µl. Then add 20 µl of 2.5× random primer/reaction buffer mix (e.g., from Gibco/BRL's BIOPRIME™ labeling kit).

2. Mix the samples well and then boil for 5 minutes.

3. Immediately place the samples on ice and allow to sit for 5 minutes.

4. On ice, add 2.5 μl of SPECTRAL LABELING BUFFER, for use with SPECTRAL CHIP™ (Spectral Genomics, Houston Tex.) to each sample.
5. Add 1.5 μl Cy5-dCTP or Cy3-dCTP to the respective test and reference DNA samples (1 mM stocks).
6. Finally, add 1 μl Klenow Fragment (from the Gibco/BRL BIOPRIME™ labeling kit) to the samples, mix the sample well by tapping, and re-collect by brief centrifugation.
7. Incubate the sample at 37° C. for 1½-2 hours. Place the samples on ice and determine the probe size distribution by removing a 5 μl aliquot from the reaction mix, and analyzing the aliquot by agarose gel electrophoresis (0.8% agarose). Note: Optimally, the majority of the probe should range in size between 100-500 bp.
8. Stop the reaction by adding 5 μl 0.5 M EDTA pH8.0 and incubating in a heating block at 72° C. for 10 minutes. Place the samples on ice. The samples can now be used to proceed with hybridization or can be stored at −20° C. until required.

Optimally the majority of the probe should range in size between 100-500 bp.

Step 3: Hybridize Labeled DNA to the Array

At this juncture, there should be four tubes, which should correspond to the Cy-3 and Cy-5 labeled test samples and the Cy-3, and Cy-5 labeled reference samples.
1. Combine the Cy3-labeled test DNA sample with the Cy5-labeled reference sample and, conversely, the Cy5-labeled test DNA sample with the Cy3-labeled reference sample. Add 45 μl of SPECTRAL HYBRIDIZATION BUFFER I, for use with SPECTRAL CHIP™ (Spectral Genomics, Houston Tex.) to each of the two tubes.
2. Precipitate the two samples by adding 11.3 μl of 5MNaCl and 110 μl of room temperature isopropanol. Mix the samples well and incubate in the dark at room temperature for 10-15 minutes.
3. Centrifuge the samples at full speed (10,000 g) for 10 minutes.
4. Carefully aspirate the supernatant, avoiding the pellet. Note: The pellets should have a purplish hue, indicating that there are equitable amounts of Cy3 and Cy5 labeled DNA. Too pink or too blue a sample, suggests that the corresponding genomic DNA was not effectively labeled.
5. Rinse the pellets with 500 μl of 70% ethanol and allow the pellets to air-dry briefly in the dark at room temperature.
6. Add 10 μl of sterile water (orange vial) to the pellets. Let stand at room temperature for 5 minutes and then thoroughly resuspend. After ensuring that the pellets are completely resuspended, add 30 μl of SPECTRAL HYBRIDIZATION BUFFER II, for use with SPECTRAL CHIP™ (Spectral Genomics, Houston Tex.) and mix well by repeated pipetting.
7. Denature the samples by incubating in a water bath at 72° C. for 10 minutes. Note: Alternatively, the sample can be denatured in a heating block set at 72° C. We recommend filling the wells of the heating block with water approximately 15 minutes before denaturing the samples so that the tubes are in contact with water at 72° C.
8. After the denaturation of the samples, immediately place the tubes on ice for 5 minutes.
9. Incubate the samples at 37° C. for 30 minutes.
10. Pipette the sample onto the center of the array and cover with a 22×60 cover slip to spread it out. Note: It is imperative that the entire array is covered and that air bubbles are avoided.
11. Place the slide in a hybridization chamber. If a microarray hybridization chamber is used, then add 10 μl of 2×SSC, 50% formamide to either side of the chamber. (H₂O works just as well).
12. Close the chamber and wrap with aluminum foil. Put the chambers in a Kapak Pouch with wet paper and heat seal the bag. Put the bag in a 37° C. incubator for 16 hours. Note: We recommend using a shaking platform incubator to facilitate and maintain even distribution of the probe on the slide.

Step 4: Post Hybridization Washes

While Coplinjars can be used in the post-hybridization washes, it is recommended to wash each slide in individual Petri dishes in a shaking platform incubator.
1. Pre-warm the following solutions at 50° C. in individual Petri dishes:
2×SSC, 50% deionized Formamide
2×SSC, 0.1% NP-40
0.2×SSC
2. Soak the slide in 2×SSC, 0.5% SDS briefly at room temperature and gently slide off the cover slip using a pair of clean forceps. Avoid peeling off the cover slip by force. (Alternatively, 2×SSC can be used)
3. Using a pair of forceps, transfer the slide to pre-warmed 2×SSC, 50% Formamide. Wash the slides by incubating in the shaking incubator at 50° C. for 20 minutes.
4. Repeat step 3 using pre-warmed 2×SSC, 0.1% NP-40.
5. Repeat step 3 using pre-warmed 0.2×SSC for 10 minutes.
6. Briefly rinse the slides with distilled deionized water. This last wash greatly reduces background fluorescence but should not exceed 10 seconds.
7. Immediately dry the slides under forced air. Do not air dry the slides.

The slides are now ready for scanning.

A number of embodiments of the invention have been described. Nevertheless, it will be understood that various modifications may be made without departing from the spirit and scope of the invention. Accordingly, other embodiments are within the scope of the following claims.

What is claimed is:

1. An array comprising: a plurality of nucleic acid segments, wherein each nucleic acid segment is immobilized to a discrete and known spot on a substrate surface to form an array of nucleic acids, and each spot comprises a segment of genomic nucleic acid selected to detect a genetic syndrome, wherein the array-immobilized genomic nucleic acid segments are covalently bound to the substrate surface through a compound having the general formula: $R_1$—X—$R_2$, and wherein $R_1$ is a cyclic ether, an aldehyde, or a chloromethylphenyl moiety; X is a moiety chemically suitable for linking the $R_1$ moiety to the $R_2$ moiety, and the $R_2$ moiety has the general formula

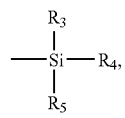

wherein $R_3$, $R_4$ and $R_5$ comprise identical or different alkoxy groups or chloro groups.

2. The away of claim 1, further comprising at least one spot comprising a nucleic acid segment acting as a positive control.

3. The array of claim 1, further comprising at least one spot comprising a nucleic acid segment acting as a negative control.

4. The array of claim 1, wherein the array-immobilized genomic nucleic acid segments in a first spot are non-overlapping in sequence compared to the array-immobilized genomic nucleic acid segments in a second spot.

5. The array of claim 4, wherein the array-immobilized genomic nucleic acid segments in the first spot are non-overlapping in sequence compared to the array-immobilized genomic nucleic acid segments in all other genomic nucleic acid-comprising spots on the array.

6. The array of claim 1, wherein at least one genomic nucleic acid segment is spotted in duplicate or triplicate on the array.

7. The array of claim 1, wherein the duplicate spot or triplicate spot has a different amount of nucleic acid segments immobilized.

8. The array of claim 6, wherein all the genomic nucleic acid segments are spotted in duplicate or triplicate on the array.

9. The array of claim 1, wherein about 95% of the array-immobilized genomic nucleic acid segments comprise a label.

10. The array of claim 1, wherein about 98% of the array-immobilized genomic nucleic acid segments comprise a label.

11. The array of claim 1, wherein 100% of the array-immobilized genomic nucleic acid segments comprise a label.

12. The array of claim 1, wherein at least one nucleic acid segment is cloned in a construct comprising an artificial chromosome.

13. The array of claim 12, wherein the artificial chromosome comprises a bacterial artificial chromosome (BAC).

14. The array of claim 12, wherein the artificial chromosome is selected from the group consisting of a human artificial chromosome (HAC) a yeast artificial chromosome (YAC), a transformation-competent artificial chromosome (TAC) and a bacteriophage P1-derived artificial chromosome (PAC).

15. The array of claim 1, wherein at least one nucleic acid segment is cloned in a construct comprising a vector selected from the group consisting of a cosmid vector, a plasmid vector and a viral vector.

16. The array of claim 1, wherein at least one of the nucleic acid segments is between about 50 kilobases to about 500 kilobases in length.

17. The array of claim 16, wherein the at least one nucleic acid segment is between about 100 kilobases to about 400 kilobases in length.

18. The array of claim 17, wherein the at least one nucleic acid segment is about 300 kilobases in length.

19. A compilation of nucleic acids for diagnosis of a genetic syndrome, the compilation comprising a plurality of nucleic acid segments, wherein each nucleic acid segment comprises a segment of genomic nucleic acid selected to detect a genetic syndrome, wherein the nucleic acid segments further comprise a compound having the general formula $$R_1\text{—}X\text{—}Si(OR_2)_m(Cl)_n(R)_k,$$

wherein m+k is the integer 3, and n can be 0 if m is greater than 0, or n+k is the integer 3 and m can be 0 if n is greater than 0; X is an inert linker; $R_1$ comprises a group reactive toward the biological molecule; R is an alkyl group; and $R_2$ is an alkyl group.

20. The compilation of nucleic acids of claim 19, wherein the nucleic acid segments further comprise a cloning vehicle.

21. The compilation of nucleic acids of claim 19, wherein the nucleic acid segments are immobilized onto a surface.

22. The compilation of nucleic acids of claim 21, wherein the nucleic acid segments are immobilized on a surface as an array.

23. The compilation of nucleic acids of claim 19, wherein about 95% of the nucleic acid segments comprise a label.

24. The compilation of nucleic acids of claim 19, wherein about 98% of the nucleic acid segments comprise a label.

25. The compilation of nucleic acids of claim 19, wherein 100% of the nucleic acid segments comprise a label.

26. The compilation of nucleic acids of claim 19, wherein at least one nucleic acid segment is cloned in a construct comprising an artificial chromosome.

27. The compilation of nucleic acids of claim 26, wherein the artificial chromosome comprises a bacterial artificial chromosome (BAC).

28. The compilation of nucleic acids of claim 26, wherein the artificial chromosome is selected from the group consisting of a human artificial chromosome (HAC), a yeast artificial chromosome (YAC), a transformation-competent artificial chromosome (TAC) and a bacteriophage P1-derived artificial chromosome (PAC).

29. The compilation of nucleic acids of claim 19, wherein at least one nucleic acid segment is cloned in a construct comprising a vector selected from the group consisting of a cosmid vector, a plasmid vector and a viral vector.

30. The compilation of nucleic acids of claim 19, wherein the nucleic acid segments are between about 50 kilobases to about 500 kilobases in length.

31. The compilation of nucleic acids of claim 30, wherein the nucleic acid segments are between about 100 kilobases to about 400 kilobases in length.

32. The compilation of nucleic acids of claim 31, wherein the cloned nucleic acid segments are between about 150 kilobases and about 300 kilobases in length.

33. An array comprising: a plurality of nucleic acid segments, wherein each nucleic acid segment is immobilized to a discrete and known spot on a substrate surface to form an array of nucleic acids, and each spot comprises a segment of genomic nucleic acid selected to detect a genetic syndrome, wherein the array-immobilized genomic nucleic acid segments are covalently bound to the substrate surface through a compound having the general formula: $R_1$—X—$R_2$, wherein $R_1$ is an amino group, $R_2$ is an alkoxysilane group or a chlorohalide group; and X is a moiety chemically suitable for linking the $R_1$ group and the $R_2$ group.

34. The array of claim 31, further comprising at least one spot comprising a nucleic acid segment acting as a positive control.

35. The array of claim 31, further comprising at least one spot comprising a nucleic acid segment acting as a negative control.

36. The array of claim 31, wherein the array-immobilized genomic nucleic acid segments in a first spot are non-overlapping in sequence compared to the array-immobilized genomic nucleic acid segments in a second spot.

37. The array of claim 36, wherein the array-immobilized genomic nucleic acid segments in the first spot are non-overlapping in sequence compared to the array-immobilized genomic nucleic acid segments in all other genomic nucleic acid-comprising spots on the array.

38. The array of claim 31, wherein at least one genomic nucleic acid segment is spotted in duplicate or triplicate on the array.

39. The array of claim 38, wherein the duplicate spot or triplicate spot has a different amount of nucleic acid segments immobilized.

40. The array of claim 38, wherein all the genomic nucleic acid segments are spotted in duplicate or triplicate on the array.

41. The array of claim 31, wherein about 95% of the array-immobilized genomic nucleic acid segments comprise a label.

42. The array of claim 31, wherein about 98% of the array-immobilized genomic nucleic acid segments comprise a label.

43. The array of claim 31, wherein 100% of the array-immobilized genomic nucleic acid segments comprise a label.

44. The array of claim 31, wherein at least one nucleic acid segment is cloned in a construct comprising an artificial chromosome.

45. The array of claim 44, wherein the artificial chromosome comprises a bacterial artificial chromosome (BAC).

46. The array of claim 44, wherein the artificial chromosome is selected from the group consisting of a human artificial chromosome (HAC) a yeast artificial chromosome (YAC), a transformation-competent artificial chromosome (TAC) and a bacteriophage P1-derived artificial chromosome (PAC).

47. The array of claim 31, wherein at least one nucleic acid segment is cloned in a construct comprising a vector selected from the group consisting of a cosmid vector, a plasmid vector and a viral vector.

48. The array of claim 31, wherein at least one of the nucleic acid segments is between about 50 kilobases to about 500 kilobases in length.

49. The array of claim 48, wherein the at least one nucleic acid segment is between about 100 kilobases to about 400 kilobases in length.

50. The array of claim 49, wherein the at least one nucleic acid segment is about 300 kilobases in length.

51. A method for selecting a genomic nucleic acid segment for use as a hybridization target in a comparative genomic hybridization (CGH) reaction for the detection of a chromosomal aneuploidy comprising (a) selecting a chromosomal segment that hybridizes to a single locus comprising a segment of the chromosome comprising the aneuploidy to be detected; (b) selecting a chromosomal segment having at least 15% to 25% unique sequence such that at least 75% to 85% of the sequence within the chromosomal segment is repetitive, except for chromosomal segments from the X chromosome or Y chromosome, which can have up to 90% to 95% repetitive sequences; and (c) selecting a segment selected in both step (a) and step (b), thereby selecting a genomic nucleic acid segment for use as a hybridization target in a comparative genomic hybridization (CGH) reaction for the detection of a chromosomal aneuploidy.

52. The method of claim 51 comprising selecting a chromosomal segment having at least 15% unique sequence.

53. A compilation of nucleic acids for diagnosis of a genetic syndrome, the compilation comprising a plurality of nucleic acid segments, wherein each nucleic acid segment comprises a segment of genomic nucleic acid selected to detect a genetic syndrome, wherein the nucleic acid segments further comprise a compound having the general formula: $R_1$—X—$R_2$, wherein $R_1$ is a cyclic ether, an aldehyde, or a chloromethylphenyl moiety; X is a moiety chemically suitable for linking the $R_1$ moiety to the $R_2$ moiety, and the $R_2$ moiety has the general formula

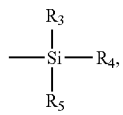

wherein $R_3$, $R_4$ and $R_5$ comprise identical or different alkoxy groups or chloro groups.

54. The compilation of nucleic acids of claim 53, wherein the nucleic acid segments further comprise a cloning vehicle.

55. The compilation of nucleic acids of claim 53, wherein the nucleic acid segments are immobilized onto a surface.

56. The compilation of nucleic acids of claim 55, wherein the nucleic acid segments are immobilized on a surface as an array.

57. The compilation of nucleic acids of claim 53, wherein about 95% of the nucleic acid segments comprise a label.

58. The compilation of nucleic acids of claim 53, wherein about 98% of the nucleic acid segments comprise a label.

59. The compilation of nucleic acids of claim 53, wherein 100% of the nucleic acid segments comprise a label.

60. The compilation of nucleic acids of claim 53, wherein at least one nucleic acid segment is cloned in a construct comprising an artificial chromosome.

61. The compilation of nucleic acids of claim 60, wherein the artificial chromosome comprises a bacterial artificial chromosome (BAC).

62. The compilation of nucleic acids of claim 60, wherein the artificial chromosome is selected from the group consisting of a human artificial chromosome (HAC), a yeast artificial chromosome (YAC), a transformation-competent artificial chromosome (TAC) and a bacteriophage P1-derived artificial chromosome (PAC).

63. The compilation of nucleic acids of claim 53, wherein at least one nucleic acid segment is cloned in a construct comprising a vector selected from the group consisting of a cosmid vector, a plasmid vector and a viral vector.

64. The compilation of nucleic acids of claim 53, wherein the nucleic acid segments are between about 50 kilobases to about 500 kilobases in length.

65. The compilation of nucleic acids of claim 64, wherein the nucleic acid segments are between about 100 kilobases to about 400 kilobases in length.

66. The compilation of nucleic acids of claim 65, wherein the cloned nucleic acid segments are between about 150 kilobases and about 300 kilobases in length.

67. A compilation of nucleic acids for diagnosis of a genetic syndrome, the compilation comprising a plurality of nucleic acid segments, wherein each nucleic acid segment comprises a segment of genomic nucleic acid selected to detect a genetic syndrome, wherein the nucleic acid segments further comprise a compound having the general formula: $R_1$—X—$R_2$, wherein $R_1$ is an amino group, $R_2$ is an alkoxysilane group or a chlorohalide group; and X is a moiety chemically suitable for linking the $R_1$ group and the $R_2$ group.

68. The compilation of nucleic acids of claim 67, wherein the nucleic acid segments further comprise a cloning vehicle.

69. The compilation of nucleic acids of claim 67, wherein the nucleic acid segments are immobilized onto a surface.

70. The compilation of nucleic acids of claim 69, wherein the nucleic acid segments are immobilized on a surface as an array.

71. The compilation of nucleic acids of claim 67, wherein about 95% of the nucleic acid segments comprise a label.

72. The compilation of nucleic acids of claim 67, wherein about 98% of the nucleic acid segments comprise a label.

73. The compilation of nucleic acids of claim 67, wherein 100% of the nucleic acid segments comprise a label.

74. The compilation of nucleic acids of claim 67, wherein at least one nucleic acid segment is cloned in a construct comprising an artificial chromosome.

75. The compilation of nucleic acids of claim 74, wherein the artificial chromosome comprises a bacterial artificial chromosome (BAC).

76. The compilation of nucleic acids of claim 74, wherein the artificial chromosome is selected from the group consisting of a human artificial chromosome (HAC), a yeast artificial chromosome (YAC), a transformation-competent artificial chromosome (TAC) and a bacteriophage P1-derived artificial chromosome (PAC).

77. The compilation of nucleic acids of claim 67, wherein at least one nucleic acid segment is cloned in a construct comprising a vector selected from the group consisting of a cosmid vector, a plasmid vector and a viral vector.

78. The compilation of nucleic acids of claim 67, wherein the nucleic acid segments are between about 50 kilobases to about 500 kilobases in length.

79. The compilation of nucleic acids of claim 78, wherein the nucleic acid segments are between about 100 kilobases to about 400 kilobases in length.

80. The compilation of nucleic acids of claim 79, wherein the cloned nucleic acid segments are between about 150 kilobases and about 300 kilobases in length.

81. An array comprising: a plurality of nucleic acid segments, wherein each nucleic acid segment is immobilized to a discrete and known spot on a substrate surface to form an array of nucleic acids, and each spot comprises a segment of genomic nucleic acid selected to detect a genetic syndrome, wherein the array-immobilized genomic nucleic acid segments are covalently bound to the substrate surface through a compound having the general formula

$$R_1\text{---}X\text{---}Si(OR_2)_m(Cl)_n(R)_k,$$

wherein m+k is the integer 3, and n can be 0 if m is greater than 0, or n+k is the integer 3 and m can be 0 if n is greater than 0; X is an inert linker; $R_1$ comprises a group reactive toward a biological molecule; R is an alkyl group; and, $R_2$ is an alkyl group.

82. The array of claim 81, further comprising at least one spot comprising a nucleic acid segment acting as a positive control.

83. The array of claim 81, further comprising at least one spot comprising a nucleic acid segment acting as a negative control.

84. The array of claim 81, wherein the array-immobilized genomic nucleic acid segments in a first spot are non-overlapping in sequence compared to the array-immobilized genomic nucleic acid segments in a second spot.

85. The array of claim 84, wherein the array-immobilized genomic nucleic acid segments in the first spot are non-overlapping in sequence compared to the array-immobilized genomic nucleic acid segments in all other genomic nucleic acid-comprising spots on the array.

86. The array of claim 81, wherein at least one genomic nucleic acid segment is spotted in duplicate or triplicate on the array.

87. The array of claim 86, wherein the duplicate spot or triplicate spot has a different amount of nucleic acid segments immobilized.

88. The array of claim 86, wherein all the genomic nucleic acid segments are spotted in duplicate or triplicate on the array.

89. The array of claim 81, wherein about 95% of the array-immobilized genomic nucleic acid segments comprise a label.

90. The array of claim 81, wherein about 98% of the array-immobilized genomic nucleic acid segments comprise a label.

91. The array of claim 81, wherein 100% of the array-immobilized genomic nucleic acid segments comprise a label.

92. The array of claim 81, wherein at least one nucleic acid segment is cloned in a construct comprising an artificial chromosome.

93. The array of claim 92, wherein the artificial chromosome comprises a bacterial artificial chromosome (BAC).

94. The array of claim 92, wherein the artificial chromosome is selected from the group consisting of a human artificial chromosome (HAC) a yeast artificial chromosome (YAC), a transformation-competent artificial chromosome (TAC) and a bacteriophage P1-derived artificial chromosome (PAC).

95. The array of claim 81, wherein at least one nucleic acid segment is cloned in a construct comprising a vector selected from the group consisting of a cosmid vector, a plasmid vector and a viral vector.

96. The array of claim 81, wherein at least one of the nucleic acid segments is between about 50 kilobases to about 500 kilobases in length.

97. The array of claim 96, wherein the at least one nucleic acid segment is between about 100 kilobases to about 400 kilobases in length.

98. The array of claim 97, wherein the at least one nucleic acid segment is about 300 kilobases in length.

* * * * *